United States Patent [19]
Lee et al.

[11] Patent Number: 5,994,367
[45] Date of Patent: Nov. 30, 1999

[54] METHOD FOR TREATING TUMORS USING 2-ARYL-NAPHTHYRIDIN-4-ONES

[75] Inventors: Kuo-Hsiung Lee; Ke Chen, both of Chapel Hill, N.C.; Sheng-Chu Kuo, Tai Chung, Taiwan

[73] Assignee: The University of North Carolina at Chapel Hill, Chapel Hill, N.C.

[21] Appl. No.: 08/812,516

[22] Filed: Mar. 7, 1997

[51] Int. Cl.⁶ .................. A61K 31/395; C07D 471/02
[52] U.S. Cl. .................. 514/300; 546/122; 435/7.2
[58] Field of Search ................ 546/122; 514/300; 435/7.2

[56] References Cited

U.S. PATENT DOCUMENTS

| | | | |
|---|---|---|---|
| 2,713,048 | 7/1955 | Weston | 260/294.8 |
| 3,681,368 | 8/1972 | Winn | 260/295 T |
| 3,929,787 | 12/1975 | Yale | 260/251 |
| 3,962,262 | 6/1976 | Williams et al. | 260/294.8 C |
| 4,042,765 | 8/1977 | Floyd et al. | 526/6 |
| 4,652,567 | 3/1987 | Martin et al. | 514/254 |
| 4,657,915 | 4/1987 | Lesher et al. | 514/300 |
| 4,697,021 | 9/1987 | Lesher et al. | 546/288 |
| 4,786,642 | 11/1988 | Teulon | 514/300 |

FOREIGN PATENT DOCUMENTS

| | | |
|---|---|---|
| 1 444 150 | 7/1976 | Belgium . |
| 406209 | 11/1924 | Germany . |
| WO92/07468 | 5/1992 | WIPO . |

OTHER PUBLICATIONS

Kelly et al.: Bisubstrate Reaction Templates. Examination of the Consequences of Identical versus different Binding Sites; *J. Am. Chem. Soc.*, 112: (1990), pp. 8024–8034.

N. Katagiri et al.: Studies on Ketene and Is Derivatives; *J. Heterocycl. Chem.*, 21 (2) (1984), pp. 407–412.

P.L. Ferrarini et al.: Synthesis of Some Substituted Pyrido {1,2-α}pyrimidin–4–Ones And1,8–Naphthyridines; *J. Heterocycl. Chem.*, 20 (4) (1983), pp. 1053–1057.

H.L. Yale, 9–Hydroxy–2–methyl–4H–pyrido [1,2–α]pyrimidin–4–One, 9–Methyl—2phenyl 4H–pyrido [1,2—α]pyrimidin n–4–One, Ethyl 9–Hydroxy–4H–pyrido[1,2—1]pyrimidin–4–One–3–carboxylate And Their Derivatives; *J. Heterocycl. Chem.*, 12(1975), pp. 427–431.

P.L. Ferrarini et al.: One Step Synthesis Of Pyrimido [1,2–α][1,8]Nnaphthyridinones, Pyrido [1,2–α] Pyrimidinones And 1,8–Naphthyridinones. Antihypertensive Agents. V; *J. Heterocycle. Chem.*, 27 (4) (1990), pp. 881–886.

A. Horvath, and I. Hermecz: Nitrogen Bridgehead Compounds; *J. Heterocycle. Chem.*, 23 (5) (1986) pp. 1295–1298.

M. Shur, and S. S. Israelstam: The Reaction Of Reaction Of Amino Heterocycles With Reactive Esters. I. 2–Aminopyridines; *J. Org. Chem.*, 33 (8) (1968), pp. 3015–3020.

R. Adams, and I. J. Pachter: Ultraviolet Spectra And Structures Of The Pyrido [1,2–α]Pyrimidones; *J. Amer. Chem. Soc.*, 74 (1952), pp. 5491–5497.

I. A. Kaye et al., N,N–Dimethyl–N'–Benzohydryl–N'–(2–Pyridyl)–Ethylenediamine And Related Compounds As Histamine Antagonists; *J. Amer. Chem. Soc.*, 74 (1952), pp. 403–407.

K. Feist, Uber einige Derivate des 2–amino–pyridins; *Arch. Pharm (Weinheim Ger.)*, 272 (1934), pp. 101–113.

P. Cherubim et al., synthesis And Biological Evaluation Of Phenanthrene–Derived Carboxamides As Cytotoxic Agents; *Anti—Cancer Drug Design*, 8 (1993), pp. 429–438.

K. Chen et al., Antitumor Agents. 178. Synthesis And Biological Evaluation Of Substituted 2–Aryl—1,8–Naphthyridin—4 (1H) —Ones As Antitumor Agents That Inhibit Tubulin Polymerization; *J. Med. Chem.*, 40 (19) (1997), pp. 3049–3056.

I. A. Savich et al., Synthesis Of a Series Of Schiff Bases Formed From Aromatic Hydroxy Aldehyes And Heterocyclic Amines; *Chemical Abstracts*, Abstract No. 1334b vol. 52 (12) (1959).

L. Li et al.; Antitumor Agents. 2',3',4',5',6,7–Substituted 2–Phenyl–4–quinolones and Related Compounds: Their Synthesis, Cytotoxicity, and Inhibition of Tubulin Polymerization, *J. Med. Chem.* 97, No. 8: 1126–1135 (1994).

L. Li et al.; Antitumor Agents 155. Synthesis and Biological Evaluation of 3', 6,7–Substituted 2–Phenyl–4–9uinolones as Antimicrotubule Agents, *J. Med. Chem.* 37, No. 20:3400–3407 (1994).

S. Kuo et al.; Synthesis and Cytotoxicity of 1,6,7,8–Substituted 2–(4'–Substituted phenyl)–4–quinolones and Related Compounds: Identidication as Antimitotic Agents Interacting with Tubulin, *J. Med. Chem.* 36, No. 9:1146–1156 (1993).

E. Rowinski et al.; The Clinical Pharmacology and Use of Antimicrotubule Agents in Cancer Chemotherapeutics, *Pharmac. Ther.* 52:35–84 (1991).

S. Hastie; Interactions of Colchicine with Tubulin, *Pharmac. Ther.* 51:377–401 (1991).

(List continued on next page.)

*Primary Examiner*—Alan L. Rotman
*Assistant Examiner*—Charanjit S. Aulakh
*Attorney, Agent, or Firm*—Myers Bigel Sibley & Sajovec

[57] ABSTRACT

The present invention provides compounds of Formula I:

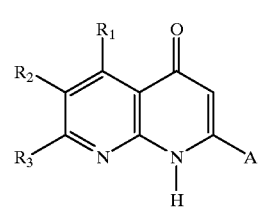

wherein A and $R_1$–$R_8$ are defined herein. The compounds of Formula I inhibit the polymerization of tubulin and possess antimitotic activity. The compounds of Formula I may be useful for the treatment of psoriasis, gout, papiloma, warts, and a variety of tumors.

28 Claims, No Drawings

OTHER PUBLICATIONS

C. Lin et al.; Antimitotic Natural Products Combretastatin A–4 and Combretastatin A–2: Studies on the mechanism of Their Inhibition of the Binding of Colchicine to Tubulin, *Biochemistry* 28:6984–6991 (1989).

C. Lin et al.; Interactions of Tubulin with Potent Natural and Synthetic Analogs of the Antimitotic Agent Combrestastatin: a Structure–Activity Study, *Molecular Pharm.* 34:200–208 (1988).

N. Katagiri et al.;. Reactions of Haloketenes with 2–Arylideneaminopyridines, *Studies on Ketene and Its Derivatives*, Part 119[1] 21:407–412 (1984).

C. Chandler et al.; The Synthesis of Macrocyclic Polyether–Diesters Incorporating 1,10–Phenanthrolino and 1,8–Naphthyridino Subunits, *J. Heterocyclic Chem.* 19:1017–1019 (1982).

R. Wang et al.; Antimitotic and Antiubulin Activity of the Tumor Inhibitor Steganacin, *Cancer Res.* 37:3071–3079 (1977).

M. Kelly et al.; The Biological Effects and the Chemical Composition of Polophyllin. A Review, *J. of Natl. Cancer Inst.* 14, No. 4:967–1010 (1954).

METHOD FOR TREATING TUMORS USING 2-ARYL-NAPHTHYRIDIN-4-ONES

The present invention was made under grant number CA-17625 from the National Cancer Institute and grant number CHE-9412095 from the National Science Counsel. The United States government has rights in the instant invention.

FIELD OF THE INVENTION

The present invention relates to new compounds within the general class of 2-aryl-1,8-naphthyridin-4-ones. The present invention also relates to methods of inhibiting cellular mitosis and/or tumor growth.

BACKGROUND OF THE INVENTION

The microtubule system of eukaryotic cells is an attractive target for the development of compounds useful in anticancer chemotherapeutics. Microtubules show highly dynamic instability and play an important role in cellular mitosis. Chemicals that attack microtubules through their major structural component, tubulin, disrupt or suppress both microtubule structure and normal functions by inhibition or promotion of microtubule assembly. Inihibition or arrest of cellular mitosis is the result.

One example of conventional antimitotic agents includes the vinca alkaloids, which inhibit microtubule polymerization. Another example of conventional antimitotic agents includes the taxoids, which promote microtubule assembly.

Colchicine is another conventional antimitotic agent. Although colchicine has limited medicinal application due to its high toxicity, it has played a findamental role in elucidation of the properties and functions of tubulin and microtubules.

Many natural products, such as cornigerine, podophyllotoxin, steganacin, and combretastatins, bind to the colchicine site of tubulin. Structurally, the compounds binding to this site are much simpler than those binding to vinca alkaloid or taxol domains. These compounds generally possess a "biaryl" system connected by a hydrocarbon bridge of variable length.

In the course of this group's search for novel plant-derived potent cytotoxic agents that are active against slow-growing solid tumors, we have isolated several flavonols as antitumor principles from a phytochemically and biologically heretofore uninvestigated plant, *Polanisia dodecandra*. Among these flavonols, 5,3'-dihydroxy-3,6,7,8,4'-pentamethoxyflavone showed remarkable cytotoxicity in vitro against panels of central nervous system, lung, ovarian, colon, and renal cancers and against melanoma and leukemia cell lines with $GI_{50}$ values in the low micromolar to nanomolar concentration range. Flavonoids also possess the biaryl structural pattern of compounds binding to the colchicine site. We found that this compound is a strong inhibitor of tubulin polymerization with an $IC_{50}$ value of $0.83\pm0.2\,\mu M$ and to be a potent inhibitor of radiolabeled colchicine binding to tubulin, showing 59% inhibition when present in an equimolar concentration with colchicine.

Paralleled with our studies of plant antitumor agents, we synthesized a large series of 2-aryl-1,8-naphthyridiones, which are the amino analogs of cytotoxic antimitotic flavonoids, and found that many of these compounds were cytotoxic and possess activitity against tubulin polymerization and colchicine binding.

There remains a need in the art for cytotoxic agents for use in cancer therapy. There remains a need in the art for agents capable of inhibiting cellular mitosis for use in cancer therapy. Further there remains a need in the art for methods of treating cancer and methods of providing cancer therapy.

SUMMARY OF THE INVENTION

As a first aspect, the present invention provides a compound of Formula the general Formula I:

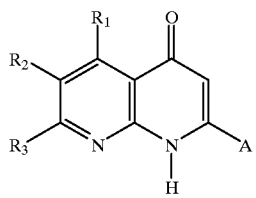

wherein A is an aromatic moeity selected from the the group consisting of:

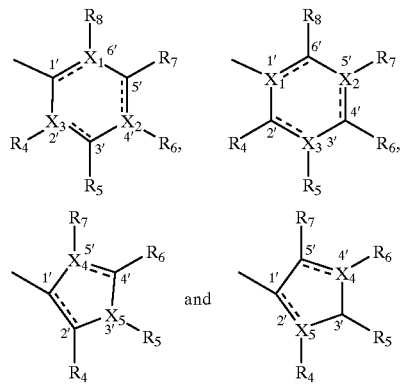

wherein $X_1$, $X_2$, and $X_3$ are each individually selected from the group consisting of C, or N; $X_4$ and $X_5$ are each individually selected from the group consisting of C, N, O, and S wherein at least one of $X_4$ and $X_5$ is N, O, or S; $R_1$, $R_2$, $R_3$, $R_4$, $R_5$, $R_6$, $R_7$, and $R_8$ are each independently selected from the group consisting of H, alkyl, hydroxyl, alkoxyl, aryloxyl, halo, amino, alkylamino, dialkylamino, or nitro, or alterantively, two adjacent R groups together may form a bridging group selected from the group consisting of alkydienyl, alkyleneoxy, alkylenedioxy, alkyleneimine, and alkylenediimine; and the dashed line indicates that the bond may be a double bond or a single bond, with the provisos that when any of $X_1$, $X_2$, $X_3$, $X_4$ or $X_5$ is C, the dashed lines connected thereto are double bonds; when any of $X_1$, $X_2$, or $X_3$ is N, the dashed lines connected thereto are double bonds and the R group attached at that position is absent; when either $X_4$ or $X_5$ is N, the dashed lines connected thereto may be single bonds or double bonds, and when the dashed line is a double bond, the R group attached at that position is absent; and when either $X_4$ or $X_5$ is O or S, the dashed lines connected thereto are single bonds and the R group attached at that position is absent.

As a second aspect, the present invention provides a process for making compounds of Formula I. The process comprises (a) reacting a compound of Formula II:

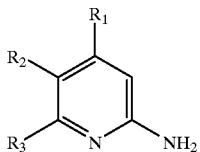

II with a compound of Formula IV:

A—CHO    IV to produce a Schiff base intermediate of Formula VI:

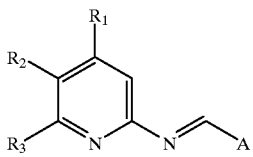

VI (b) cyclizing the Schiff base intermediate to give a pyridopyrimidinone intermediate of Formula V:

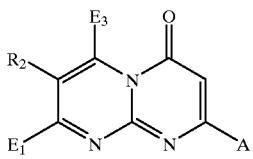

V and (c) thermally converting the pyridopyrimidinone intermediate to a compound of Formula I.

As a third aspect, the present invention provides another process for making compounds of Formula I wherein A is a six-member aromatic hydrocarbon ring. The process comprises the steps of (a) condensing a compound of Formula II with a compound of Formula III:

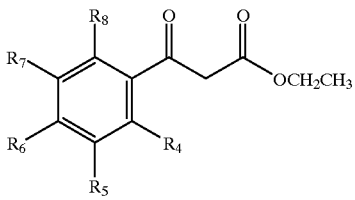

III in the presence of polyphosphoric acid to produce a pyridopyrimidinone intermediate of Formula V-A:

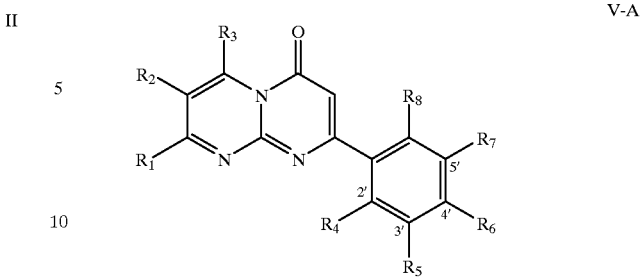

V-A and (b) thermally converting the pyridopyrimidinone intermediate of Formula V-A to a compound of Formula I wherein A is a six-member aromatic hydrocarbon ring.

As a fourth aspect, the present invention provides a compound of Formula V.

As a fifth aspect, the present invention provides a compound of Formula VI.

As a sixth aspect, the present invention provides a method for treating a tumor. The method comprises administering to a subject in need of treatment, a compound of Formula I in an amount effective to treat a tumor.

As a seventh aspect, the present invention provides a method of inhibiting cellular mitosis. The method comprises contacting a cell with a compound of Formula I in an amount effective to inhibit cellular mitosis.

The foregoing and other aspects of the present invention are explained in detail in the detailed description and examples set forth hereinbelow.

DETAILED DESCRIPTION OF THE INVENTION

As used herein the term "alkyl" refers to $C_{1-20}$ inclusive, linear, branched, or cyclic, saturated or unsaturated hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, and allenyl groups. Thus, the term "alkyl" refers to $C_{1-20}$ inclusive alkyls unless otherwise specified. The term "alkoxy" as used herein refers to $C_{1-20}$ inclusive, linear, branched, or cyclic, saturated or unsaturated oxohydrocarbon chains, including for example methoxy, ethoxy, propoxy, isopropoxy, butoxy, t-butoxy, and pentoxy. The term "aryloxyl" as used herein refers to phenyloxyl and alkyl, halo, or alkoxyl substituted phenyloxyl. The terms "halo," "halide," or "halogen" as used herein refer to fluorine, chlorine, bromine, and iodine. The term "alkylamino" refers to a group of the general formula —NHR', wherein R' is alkyl. The term "dialkylamino" refers to a group of the general formula —NR'R", wherein R' and R" are each the same of different alkyl groups. The term "heteroatom" as used herein refers to N, O, or S. The term "alkydienyl" refers to a group of the general formula —R'— where R' is alkyl. The term "alkyleneoxy" refers to a group having the general formula —OR'— or —R'OR'— where each R' is independently alkyl. The term "alkylenedioxy" refers to a group of the general formula —OR'O—, —OR'OR'—, or —R'OR'OR'— where each R' is independently alkyl. The term "alkyleneimine" refers to a group having the general formula —NR'— or —R'NR'— where each R' is independently alkyl. The term "alkylenediimine" refers to a group of the general formula —NR'N—, —NR'NR'—, or —R'NR'NR'— where each R' is independently alkyl.

The present invention provides 2-aryl-1,8-naphthyridine-4-ones of the general Formula I:

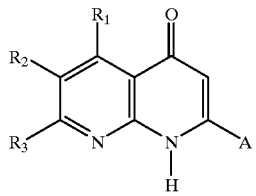

I wherein A is an aromatic moeity selected from the group consisting of:

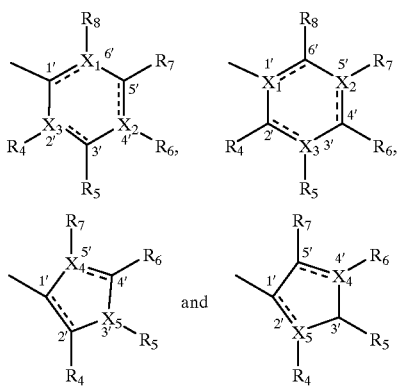

wherein:

$X_1$, $X_2$, and $X_3$ are each individually selected from the group consisting of C, or N;

$X_4$ and $X_5$ are each individually selected from the group consisting of C, N, O, and S wherein at least one of $X_4$ and $X_5$ is N, O, or S;

$R_1$, $R_2$, $R_3$, $R_4$, $R_5$, $R_6$, $R_7$, and $R_8$ are each independently selected from the group consisting of H, alkyl, hydroxyl, alkoxyl, aryloxyl, halo, amino, alkylamino, dialkylamino, or nitro, or alterantively, two adjacent R groups together may form a bridging group selected from the group consisting of alkydienyl, alkyleneoxy, alkylenedioxy, alkyleneimine, and alkylenediimine; and the dashed line indicates that the bond may be a double bond or a single bond, with the provisos that:

when any of $X_1$, $X_2$, $X_3$, $X_4$ or $X_5$ is C, the dashed lines connected thereto are double bonds;

when any of $X_1$, $X_2$, or $X_3$ is N, the dashed lines connected thereto are double bonds and the R group attached at that position is absent;

when either $X_4$ or $X_5$ is N, the dashed lines connected thereto may be single bonds or double bonds, and when the dashed line is a double bond, the R group attached at that position is absent; and when either $X_4$ or $X_5$ is O or S, the dashed lines connected thereto are single bonds and the R group attached at that position is absent.

More specifically, A is an aromatic moeity selected from the group consisting of six-member aromatic hydrocarbon rings, five-member aromatic heterocyclic rings containing 1 or 2 heteroatoms, and six-member aromatic heterocyclic rings containing 1, 2, or 3 heteroatoms, where any of these rings may include from 0 to 4 substiuents for five-member rings, or 0–5 substituents for six-member rings, which substituents are defined by variables $R_4$–$R_8$. Specific examples of suitable aromatic moeities within the scope of the definition of A of the Formula I of the present invention include, but are not limited to phenyl, pyridinyl, pyrazinyl, pyrimidinyl, pyrrole, imidazole, furan, thiophene, oxazole, thiazole, where any of those aromatic moeities may be substituted as represented by $R_4$–$R_8$ defined hereinabove.

The substituents $R_1$, $R_2$, $R_3$, $R_4$, $R_5$, $R_6$, $R_7$, and $R_8$ may be any of the species identified above, or two adjacent R groups (i.e., two R groups which are next to each other) may form a bridging group. More specifically, $R_1$ and $R_2$ may be a bridging group such that $R_1$ and $R_2$ together with the atoms to which they are attached may form a five- or six-member aromatic ring; $R_2$ and $R_3$ may be a bridging group such that $R_2$ and $R_3$ together with the atoms to which they are attached may form a five- or six-member aromatic ring; $R_4$ and $R_5$ may be a bridging group such that $R_4$ and $R_5$ together with the atoms to which they are attached may form a five- or six-member aromatic ring; $R_5$ and $R_6$ may be a bridging group such that $R_5$ and $R_6$ together with the atoms to which they are attached may form a five- or six-member aromatic ring; $R_6$ and $R_7$ may be a bridging group such that $R_6$ and $R_7$ together with the atoms to which they are attached may form a five- or six-member aromatic ring; $R_7$ and $R_8$ may be a bridging group such that $R_7$ and $R_8$ together with the atoms to which they are attached may form a five- or six-member aromatic ring. For example, the five or six-member rings which may be formed when adjacent R groups are defined as a bridging group include six-member aromatic hydrocarbon rings; which are defined when adjacent R groups are alkydienyl; five-member aromatic heterocyclic rings, which are defined when adjacent R groups are alkyleneoxy, alkylenedioxy, alkyleneimine, and alkylenediimine; and six-member aromatic heterocyclic rings, which are defined when adjacent R groups are alkyleneoxy, alkylenedioxy, alkyleneimine, and alkylenediimine.

As is evident from the general Formula I and the definition of the aromatic moeity A, the compounds of Formula I may be substituted from 1 to 8 times. More specifically, the compounds of Formula I may be substituted from 1 to 3 times in the "A" ring (i.e., the first ring of the structure) and from 1 to 5 times in the "C" ring (i.e., the aromatic moeity defined by the variable A). The compounds of Formula I include compounds having substitutions in only the "A" or only the "C" ring or in both rings. As will be apparent to those skilled in the art, when the C ring is a six-member heterocyclic moeity, the R group substituent attached at the position of the heteroatom on the ring is absent in order to accomodate the valence requirements of the heteroatoms. Similarly, when the C ring is a five-member heterocyclic moeity containing an O or S, the R group substiuent attached at the position of the O or S is absent in order to accomodate the valence requirements of that heteroatom. Thus, if A is a five-member heterocycle of the formula:

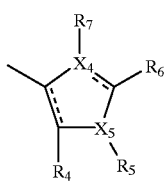

wherein $X_4$ is O or S, the dashed line connected to $X_4$ (i.e., between positions 4' and 5') is a single bond, the dashed line between positions 1' and 2' is a double bond, and R$_7$ is absent. In the embodiment wherein X$_4$ is N, the dashed line connected to X$_4$(i.e., between positions 4' and 5') may be either a single bond or a double bond, the dashed line between positions 1' and 2' is a double bond, and if the dashed line connected to X$_4$ is a double bond, R$_7$ is absent. In the embodiment wherein X$_5$ is O or S, all dashed lines are double bonds and R$_5$ is absent. Similarly, when A is a heterocycle of the formula:

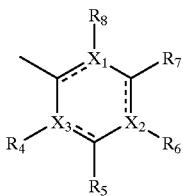

wherein X$_3$ is N and all dashed lines are double bonds, R$_4$ is absent. The other heterocyclic rings encompassed by the instant invention are similarly determined. One skilled in the art will readily appreciate the valence requirements of the different heteroatoms and will interpret the definitions of the variables in the present invention in a manner consistent with those requirements.

The compounds of Formula I wherein A is any of a six-member aromatic hydrocarbon ring, a five-member aromatic heterocycle, or a six-member aromatic heterocycle may be produced according to the following Scheme I.

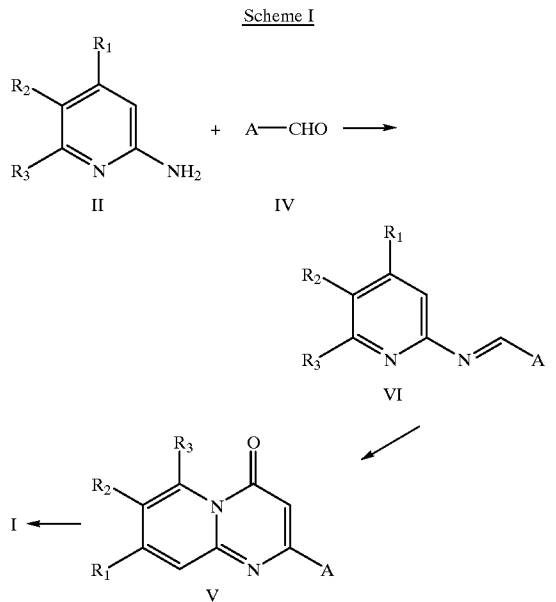

wherein A and R$_1$–R$_8$ are as defined hereinabove.

The compounds of Formula IV above are commercially available and may be produced according to techniques known in the art. According to this method, the compounds of Formula II are reacted with the compounds of Formula IV in an organic solvent to yield the Schiff base intermediate of Formula VI. Typically, the reaction is carried out under heat, and preferably at the reflux temperature of the solvent. Suitable solvents will be known to those skilled in the art, and include, for example, benzene, toluene, and m-xylene. The reaction is carried out until about 90–95% of the theoretical amount of water is recovered. The intermediates of Formula VI can be recovered by evaporating the organic solvent and distilling the residue. The compounds of Formula VI are then cyclized to the intermediate compounds of Formula V by reaction with a triethylamine and anhydrous chloroacetyl chloride. Typically the cyclization of the compounds of Formula VI to produce the compounds of Formula V is carried out in an appropriate organic solvent. Examples of suitable organic solvents include but are not limited to ethylether, methylene chloride, and tetrahydrofuran. Ethylether is currently the preferred organic solvent for the cyclization reaction.

The compound of Formula V (i.e., the pyridopyrimidinone intermediate) can be recovered using conventional recovery techniques including extraction with an organic solvent. Preferably, the compounds of Formula V are recovered by allowing the condensation reaction mixture, including the compounds of Formula V, to cool to room temperature, neutralizing the mixture with a base such as sodium hydroxide, extracting the compounds of Formula V with an appropriate organic solvent, such as methylene chloride, and passing the extract through a silica gel column.

The compounds of Formula V may then be thermally converted to the compounds of Formula I. The thermal conversion of the compounds of Formula V involves a rearrangment which forms the compounds of Formula I. The thermal conversion of the compounds of Formula V may be accomplished by adding the compound of Formula V to mineral oil, such as liquid paraffin, at a temperature of between about 300° C. and about 400° C., preferably about 350° C. After the reaction is complete, the compounds of Formula I may be recovered using silica gel chromatography and eluting with a mixture of methylene chloride and ethylacetate.

Alternatively, the compounds of Formula I wherein A is a six-member hydrocarbon ring can also be produced according to the following Scheme

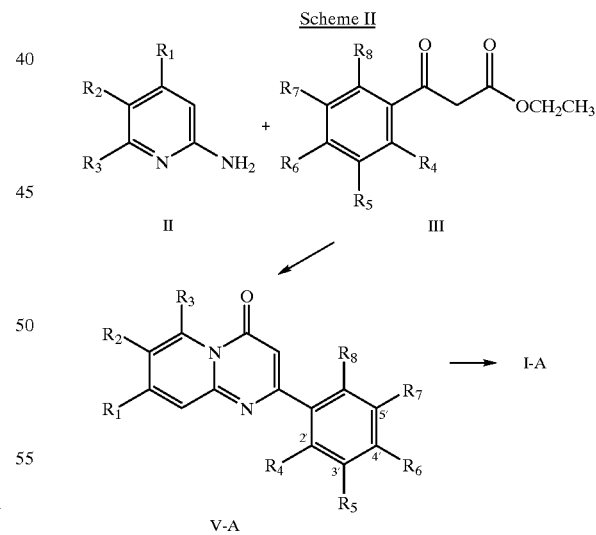

wherein R$_1$–R$_8$ are as defined above.

The starting substituted ethyl benzoylacetates of Formula III can be prepared according to techniques described in A. Krapcho, et al., *Organic Synthesis* 5:198 (1973), the disclosure of which is hereby incorporated by reference in its entirety. The substituted 2-aminopyridine of Formula II are commercially available. A compound of Formula II is combined with a compound of Formula III and polyphosphoric acid and heated to a temperature above about 100° C., preferably above about 110° C., and most preferably about 125° C. at atmospheric pressure. Preferably, the condensation reaction is carried out while stirring the mixture. If desired, the progression of the condensation reaction can be monitered by thin layer chromatography using techniques known to those skilled in the art. The product of the condensation reaction is the pyridopyrimidine intermediate compound of Formula V-A.

The compound of Formula V-A may be recovered and subsequently thermally converted to the compounds of Formula I wherein A is a six-member aromatic hydrocarbon ring (i.e., compounds of Formula I-A), according to the techniques described hereinabove for converting compounds of Formula V to compounds of Formula I.

The compounds of Formula V and VI are useful intermediates for the preparation of compounds of Formula I.

In one embodiment, preferred compounds of Formula I which are produced according to the methods of the present invention include compounds of Formula I wherein A is

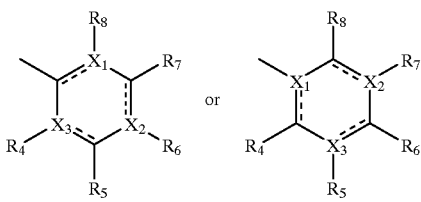

$X_1$, $X_2$, and $X_3$ are each C (i.e., A is a a six-member aromatic hydrocarbon), all dashed lines are double bonds, and $R_1$ is alkyl. In another preferred embodiment of the compounds of Formula I wherein A is

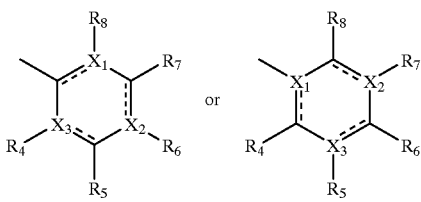

$X_1$, $X_2$, and $X_3$ are each C (i.e., A is a a six-member aromatic hydrocarbon), all dashed lines are double bonds, and $R_2$ is alkyl. In another preferred embodiment, A is

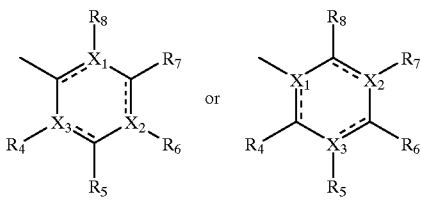

$X_1$, $X_2$, and $X_3$ are each C (i.e., A is a a six-member aromatic hydrocarbon), all dashed lines are double bonds, and $R_2$ is halo. In another preferred embodiment A is

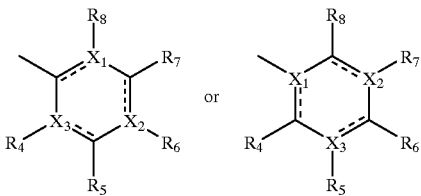

$X_1$, $X_2$, and $X_3$ are each C (i.e., A is a a six-member aromatic hydrocarbon), all dashed lines are double bonds, and $R_3$ is alkyl. In another preferred embodiment A is

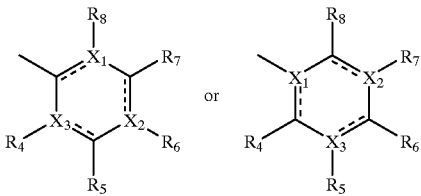

$X_1$, $X_2$, and $X_3$ are each C (i.e., A is a a six-member aromatic hydrocarbon), all dashed lines are double bonds, and $R_5$ is alkoxyl. In another preferred embodiment, A is is

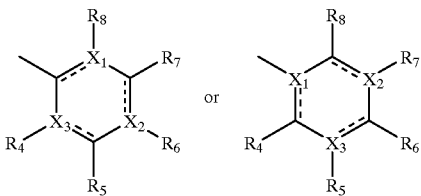

$X_1$, $X_2$, and $X_3$ are each C (i.e., A is a a six-member aromatic hydrocarbon), all dashed lines are double bonds, and $R_5$ is halo. In yet another preferred embodiment, A is

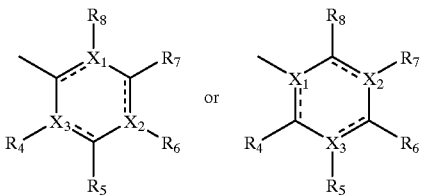

$X_1$, $X_2$, and $X_3$ are each C (i.e., A is a a six-member aromatic hydrocarbon), all dashed lines are double bonds and $R_5$ is alkyl. In another preferred embodiment, A is

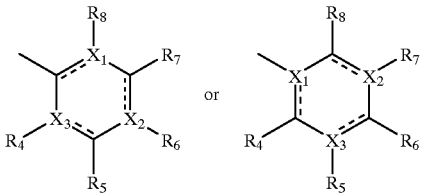

$X_1$, $X_2$, and $X_3$ are each C (i.e., A is a a six-member aromatic hydrocarbon), all dashed lines are double bonds, and $R_4$ and $R_5$ together form a $C_3$-alkydienyl bridging group, and together with the atoms to which they are attached form a 6-member aromatic ring. In another preferred embodiment, A is

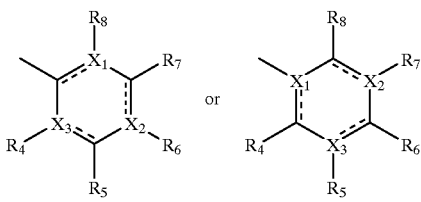

$X_1$, $X_2$, and $X_3$ are each C (i.e., A is a a six-member aromatic hydrocarbon), all dashed lines are double bonds, and $R_6$ is alkoxyl. In another embodiment, A is

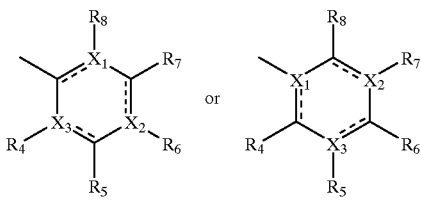

$X_1$, $X_2$, and $X_3$ are each C (i.e., A is a a six-member aromatic hydrocarbon), all dashed lines are double bonds, and $R_6$ is halo. In another embodiment A is

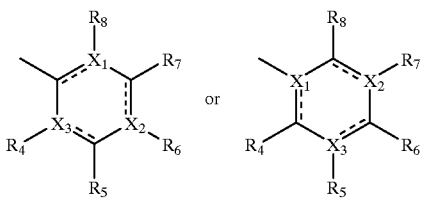

$X_1$, $X_2$, and $X_3$ are each C (i.e., A is a a six-member aromatic hydrocarbon), all dashed lines are double bonds, and $R_6$ is alkyl. In another preferred embodiment A is:

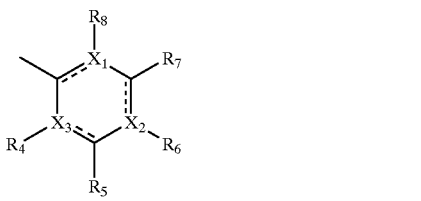

$X_1$ and $X_2$ are each C and $X_3$ is N (i.e., A is a a six-member aromatic heterocycle), all dashed lines are double bonds, $R_2$ and $R_5$ are each alkyl, and $R_4$ is absent. In another preferred embodiment A is

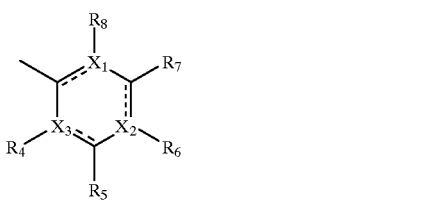

$X_1$ and $X_3$ are each C and $X_2$ is N (i.e., A is a a six-member aromatic heterocycle), all dashed lines are double bonds, $R_3$ is alkyl, and $R_6$ is absent. In another preferred embodiment, A is

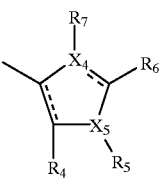

$X_4$ is C, $X_5$ is O (i.e., A is a a five-member aromatic heterocycle), all dashed lines are double bonds, $R_2$ is alkyl, and $R_5$ is absent. In another preferred embodiment, A is

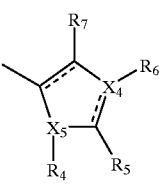

$X_4$ is C, $X_5$ is O (i.e., A is a a five-member aromatic heterocycle), all dashed lines are double bonds, $R_2$ is alkyl, and $R_4$ is absent. In another preferred embodiment, A is

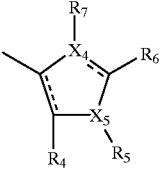

$X_4$ is C, $X_5$ is N (i.e., A is a a five-member aromatic heterocycle), all dashed lines are double bonds, $R_2$ is alkyl, and $R_5$ is absent. In another preferred embodiment, A is

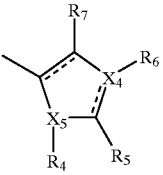

$X_4$ is C, $X_5$ is N (i.e., A is a a five-member aromatic heterocycle), all dashed lines are double bonds, $R_2$ is alkyl, and $R_4$ is absent. In another preferred embodiment, A is

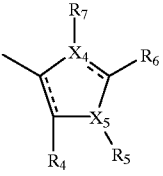

$X_4$ is C, $X_5$ is S (i.e., A is a a five-member aromatic heterocycle), all dashed lines are double bonds, $R_2$ is alkyl, and $R_5$ is absent. In another preferred embodiment, A is

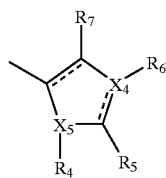

$X_4$ is C, $X_5$ is S (i.e., A is a a five-member aromatic heterocycle), all dashed lines are double bonds, $R_2$ is alkyl, and $R_4$ is absent.

Specific examples of preferred compounds of Formula I include compounds defined as follows:

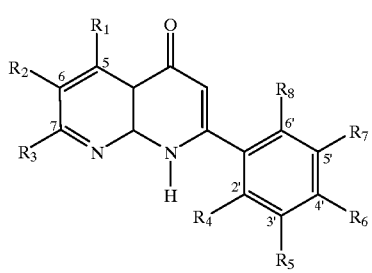

I-A wherein:

| $R_1$ | $R_2$ | $R_3$ | $R_4$ | $R_5$ | $R_6$ | $R_7$ | $R_8$ |
|---|---|---|---|---|---|---|---|
| H | H | H | H | alkoxyl | H | H | H |
| alkyl | H | H | H | alkoxyl | H | H | H |
| H | alkyl | H | H | alkaxyl | H | H | H |
| H | H | alkyl | H | alkoxyl | H | H | H |
| alkyl | H | alkyl | H | alkoxyl | H | H | H |
| H | halo | H | H | alkoxyl | H | H | H |
| alkyl | H | H | H | H | alkoxyl | H | H |
| H | alkyl | H | H | H | alkoxyl | H | H |
| alkyl | H | H | H | H | halo | H | H |
| H | alkyl | H | H | H | halo | H | H |
| alkyl | H | H | H | H | alkyl | H | H |
| H | alkyl | H | H | H | alkyl | H | H |
| H | H | alkyl | H | H | alkyl | H | H |
| alkyl | H | alkyl | H | H | alkyl | H | H |
| H | alkyl | H | H | halo | H | H | H |
| H | H | alkyl | H | halo | H | H | H |
| alkyl | H | alkyl | H | halo | H | H | H |
| H | H | H | H | halo | H | H | H |
| alkyl | H | H | H | halo | H | H | H |
| H | alkyl | H | H | halo | H | H | H |
| H | H | alkyl | H | halo | H | H | H |
| alkyl | H | H | H | alkyl | H | H | H |
| H | H | H | $C_3$ alkydienyl | H | H | H | H |
| alkyl | H | H | $C_3$ alkydienyl | H | H | H | H |
| H | alkyl | H | $C_3$ alkydienyl | H | H | H | H |
| H | H | alkyl | $C_3$ alkydienyl | H | H | H | H |
| alkyl | H | alkyl | $C_3$ alkydienyl | H | H | H | H |

Another specific example of compounds of Formula I are defined as follows:

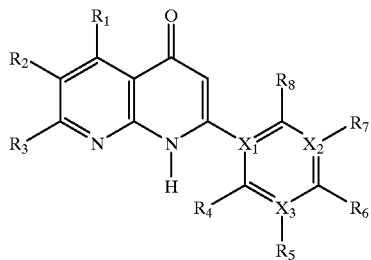

I-B wherein $X_1$ and $X_2$ are C, $X_3$ is N, $R_1$, $R_3$, $R_4$, $R_6$, and $R_8$ are each H, $R_2$ and $R_7$ are each alkyl and $R_5$ is absent.

Another specific example of compounds of Formula I are defined as follows:

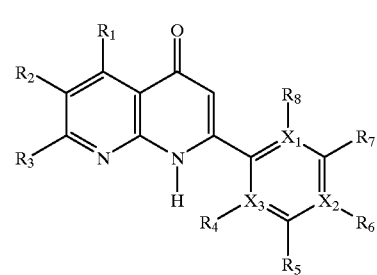

I-C wherein $X_1$ and $X_3$ are C, $X_2$ is N, $R_1$, $R_2$, $R_4$, $R_5$, $R_7$, and $R_8$ are each H, $R_3$ is alkyl, and $R_6$ is absent.

Other specific examples of compounds of Formula I are defined as follows:

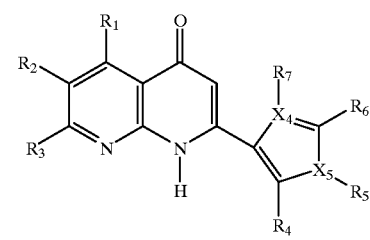

I-D wherein

| $X_4$ | $X_5$ | $R_1$ | $R_2$ | $R_3$ | $R_4$ | $R_5$ | $R_6$ | $R_7$ |
|---|---|---|---|---|---|---|---|---|
| C | O | H | alkyl | H | H | absent | H | H |
| C | N | H | alkyl | H | H | absent | H | H |
| C | S | H | alkyl | H | H | absent | H | H |
| C | O | H | alkyoxl | H | H | absent | H | H |
| C | N | H | alkaxyl | H | H | absent | H | H |
| C | S | H | alkoxyl | H | H | absent | H | H |

Other specific examples of compounds of Formula I are defined as follows:

I-E (structure with R1, R2, R3, R7, R6, X4, X5, R5, R4 substituents on naphthyridinone fused with five-membered ring)

wherein

| $X_4$ | $X_5$ | $R_1$ | $R_2$ | $R_3$ | $R_4$ | $R_5$ | $R_6$ | $R_7$ |
|---|---|---|---|---|---|---|---|---|
| C | O | H | alkyl | H | absent | H | H | H |
| C | N | H | alkyl | H | absent | H | H | H |
| C | S | H | alkyl | H | absent | H | H | H |
| C | O | H | alkyoxl | H | absent | H | H | H |
| C | N | H | alkoxyl | H | absent | H | H | H |
| C | S | H | alkoxyl | H | absent | H | H | H |

The compounds of Formulas I-A, I-B, I-C, I-D, and I-E set forth hereinabove are encompassed by the scope of general Formula I hereinabove and are set forth herein for additional clarity.

Examples of specific compounds according to Formula I include but are not limited to:
2-(2'-Methoxyphenyl)-1,8-naphthyridin-4-one,
2-(2'-Methoxyphenyl)-5-methyl-1,8-naphthyridin-4-one,
2-(2'-Methoxyphenyl)-6-methyl-1,8-naphthyridin-4-one,
2-(2'-Methoxyphenyl)-7-methyl-1,8-naphthyridin-4-one,
2-(2'-Methoxyphenyl)-5,7-dimethyl-1,8-naphthyridin-4-one,
2-(3'-Methoxyphenyl)-1,8-naphthyridin-4-one,
2-(3'-Methoxyphenyl)-5-methyl-1,8-naphthyridin-4-one,
2-(3'-Methoxyphenyl)-6-methyl-1,8-naphthyridin-4-one,
2-(3'-Methoxyphenyl)-7-methyl-1,8-naphthyridin-4-one,
2-(3'-Methoxyphenyl)-5,7-dimethyl-1,8-naphthyridin-4-one,
2-(3'-Methoxyphenyl)-6-chloro-1,8-naphthyridin-4-one,
2-(3'-Methoxyphenyl)-6-bromo-1,8-naphthyridin-4-one,
2-(4'-Methoxyphenyl)-1,8-naphthyridin-4-one,
2-(4'-Methoxyphenyl)-5-methyl-1,8-naphthyridin-4-one,
2-(4'-Methoxyphenyl)-6-methyl-1,8-naphthyridin-4-one,
2-(4'-Methoxyphenyl)-7-methyl-1,8-naphthyridin-4-one,
2-(4'-Methoxyphenyl)-5,7-dimethyl-1,8-naphthyridin-4-one,
2-(4'-Fluorophenyl)-1,8-naphthyridin-4-one,
2-(4'-Fluorophenyl)-5-methyl-1,8-naphthyridin-4-one,
2-(4'-Fluorophenyl)-6-methyl-1,8-naphthyridin-4-one,
2-(4'-Fluorophenyl)-7-methyl-1,8-naphthyridin-4-one,
2-(4'-Fluorophenyl)-5,7-dimethyl-1,8-naphthyridin-4-one,
2-(4'-Fluorophenyl)-6-chloro-1,8-naphthyridin-4-one,
2-(4'-Chlorophenyl)-1,8-naphthyridin-4-one,
2-(4'-Chlorophenyl)-5-methyl-1,8-naphthyridin-4-one,
2-(4'-Chlorophenyl)-6-methyl-1,8-naphthyridin-4-one,
2-(4'-Chlorophenyl)-7-methyl-1,8-naphthyridin-4-one,
2-(4'-Chlorophenyl)-5,7-dimethyl-1,8-naphthyridin-4-one,
2-(4'-Methylphenyl)-5-methyl-1,8-naphthyridin-4-one,
2-(4'-Methylphenyl)-6-methyl-1,8-naphthyridin-4-one,
2-(4'-Methylphenyl)-7-methyl-1,8-naphthyridin-4-one,
2-(4'-Methylphenyl)-5,7-dimethyl-1,8-naphthyridin-4-one,
2-(3'-Fluorophenyl)-6-methyl-1,8-naphthyridin-4-one,
2-(3'-Fluorophenyl)-7-methyl-1,8-naphthyridin-4-one,
2-(3'-Fluorophenyl)-5,7-dimethyl-1,8-naphthyridin-4-one,
2-(3'-Chlorophenyl)-1,8-naphthyridin-4-one,
2-(3'-Chlorophenyl)-5-methyl-1,8-naphthyridin-4-one,
2-(3'-Chlorophenyl)-6-methyl-1,8-naphthyridin-4-one,
2-(3'-Chlorophenyl)-7-methyl-1,8-naphthyridin-4-one,
2-(3'-Chlorophenyl)-5,7-dimethyl-1,8-naphthyridin-4-one,
2-(3'-Methylphenyl)-1,8-naphthyridin-4-one,
2-(3'-Methylphenyl)-5-methyl-1,8-naphthyridin-4-one,
2-(3'-Methylphenyl)-6-methyl-1,8-naphthyridin-4-one,
2-(3'-Methylphenyl)-7-methyl-1,8-naphthyridin-4-one,
2-(3'-Methylphenyl)-5,7-dimethyl-1,8-naphthyridin-4-one,
2-(α-Naphthyl)-1,8-naphthyridin-4-one,
2-(α-Naphthyl)-5-methyl-1,8-naphthyridin-4-one,
2-(α-Naphthyl)-6-methyl-1,8-naphthyridin-4-one,
2-(α-Naphthyl)-7-methyl-1,8-naphthyridin-4-one,
2-(α-Naphthyl)-5,7-dimethyl-1,8-naphthyridin-4-one,
2-(β-Naphthyl)-1,8-naphthyridin-4-one,
2-(β-Naphthyl)-5-methyl-1,8-naphthyridin-4-one,
2-(β-Naphthyl)-6-methyl-1,8-naphthyridin-4-one,
2-(β-Naphthyl)-7-methyl-1,8-naphthyridin-4-one,
2-(β-Naphthyl)-5,7-dimethyl-1,8-naphthyridin-4-one,
2-(β-Naphthyl)-6-chloro-1,8-naphthyridin-4-one,
2-(5-Methylpyrid-3-yl)-6-methyl-1,8-naphthyridin-4-one,
2-(Pyrid-4-yl)-7-methyl -1,8-naphthyridin-4-one,
2-Fur-2-yl-6-methyl-1,8-naphthyridin-4-one,
2-Fur-3-yl-6-methyl-1,8-naphthyridin-4-one,
2-Pyrrol-2-yl-6-methyl-1,8-naphthyridin-4-one,
2-Pyrrol-3-yl-6-methyl-1,8-naphthyridin-4-one,
2-Thien-2-yl-6-methyl-1,8-naphthyridin-4-one, and
2-Thien-3-yl-6-methyl-1,8-naphthyridin-4-one.

The compounds of Formula I are useful as pharmaceutically active agents. The compounds of Formula I may be formulated for administration for the treatment of a variety of conditions. In the manufacture of a pharmacuetical formulation according to the invention, the compounds of Formula I and the physiologically acceptable salts thereof, or the acid derivatives of either thereof (hereinafter referred to as the "active compound") are typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.5% to 95% by weight of the active compound. One or more active compounds may be incorporated in the formulations of the invention, which may be prepared by any of the well known techniques of pharmacy consisting essentially of admixing the components, optionally including one or more accessory ingredients.

The formulations of the invention include those suitable for oral, rectal, topical, buccal (e.g., sub-lingual), parenteral (e.g., subcutaneous, intramuscular, intradermal, or intravenous) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above).

In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration conveniently comprise sterile aqueous preparations of the active compound, which preparations are preferably isotonic with the blood of the intended recipient. These preparations may be administered by means of subcutaneous, intravenous, intramuscular, or intradermal injection. Such preparations may conveniently be prepared by admixing the compound with water or a glycine buffer and rendering the resulting solution sterile and isotonic with the blood.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include vaseline, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bistris buffer (pH 6) or ethanol/water and contain from 0.1 to 0.2M active ingredient.

The compounds of Formula I inhibit tubulin polymerization and have antimitotic activity. Such compounds are useful for the treatment of conditions including psoriasis, gout, papiloma, warts, and various tumors including but not limited to non-small cell lung cancer, colon cancer, central nervous system cancers, melanoma, overian cancer, prostate cancer and breast cancer. Data regarding the activity of compounds of Formula I is provided in the Examples which follow.

Subjects to be treated by the methods of the present invention are typically human subjects although the methods of the present invention may be useful with any suitable subjects known to those skilled in the art, and particularly mammalian subjects including, in addition to humans, horses, cows, dogs, rabbits, fowl, sheep, and the like. As noted above, the present invention provides pharmaceutical formulations comprising the compounds of Formula I, or pharmaceutically acceptable salts thereof, in pharmaceutically acceptable carriers for oral, rectal, topical, buccal, parenteral, intramuscular, intradermal, or intravenous, and transdermal administration.

Obviously, the therapeutically effective dosage of any specific compound, the use of which is in the scope of present invention, will vary somewhat from compound to compound, patient to patient, and will depend upon the condition of the patient and the route of delivery. As a general proposition, a dosage from about 0.1 to about 50 mg/kg will have therapeutic efficacy, with still higher dosages potentially being employed for oral and/or aerosol administration. Toxicity concerns at the higher level may restrict intravenous dosages to a lower level such as up to about 10 mg/kg, all weights being calculated based upon the weight of the active base, including the cases where a salt is employed. Typically a dosage from about 0.5 mg/kg to about 5 mg/kg will be employed for intravenous or intramuscular administration. A dosage from about 10 mg/kg to about 50 mg/kg may be employed for oral administration.

The following Examples are provided to further illustrate the present invention, and should not be construed as limiting thereof. The present invention is defined by the claims which follow. Melting points were determined on a Fisher-John melting point apparatus and are uncorrected. Elemental analyses were performed on a Carlo Erba EA 1108 elemental analyzer. Proton Nulear Magnetic Resonance ($^1$H NMR) spectra were measured on a Bruker AC-300 spectrometer with tetramethylsilane (TMS) as the internal standard. Chemical shifts are reported in $\delta$ (ppm). Mass spectra (MS) were obtained on a TRIO 1000 mass spectrometer. Flash column chromatography was performed on silica gel (mesh 25–150 $\mu$m) using a mixture of $CH_2Cl_2$ amd EtOAc as eluant. Precoated silica gel plates (Kieselgel 60 $F_{254}$ 0.25 mm, Merck) was used for thin layer chromatography (TLC) analysis. In these examples, "g" means grams, "mg" means milligrams, "mL" means milliliters, "min." means minute (s), "° C." means degress Centigrade.

EXAMPLE 1

Preparation of Substituted Ethyl Benzoylacetates

The substituted ethyl benzolylacetates were prepared according to procedures described in Krapcho et al., *Organic Synthesis* 5:198 (1973). To a vigorously stirring suspension of NaH and CO(OEt)$_2$ in toluene was added dropwise a solution of substituted acetophenone in toluene under reflux. The mixture was allowed to reflux and was stirred for 20 min after the addition was complete. When cooled to room temperature, the mixture was acidified with glacial AcOH. After ice-cold water was added, the mixture wasa extracted with toluene. The extract was then dried over MgSO$_4$. After the toluene was evaporated at atmospheric pressure, the residue was distilled in vacuo to give the corresponding substituted ethyl benzoylacetates.

EXAMPLE 2

General Procedures for the Preparation of 2-Aryl-pyrido[1,2-a]pyrimidin-4-ones and 2-Aryl-1,8-naphthyridin-4-ones Method 1. A mixture of substituted 2-aminopyridine (1), substituted ethyl benzoylacetate (2), and PPA was heated at 125° C. with stirring. The reaction was monitored by TLC. After the reaction was completed, the mixture was cooled to room temperature and neutralized with 4M NaOH. After extraction with Ch$_2$Cl$_2$, the extract was passed through a silica gel column to give 2-phenyl-pyrido[1,2-a]pyrimidin-4-ones. The 2-phenyl-pyrido[1-2, a]pyrimidin-4-one was then added to liquid paraffin at 350° C. for 2 hr after the addition was complete. The cooled mixture was subjected to silica gel column chromatography. Elution with CH$_2$Cl$_2$-EtOAc gave the corresponding 2-phenyl-1,8-naphthyridin-4-ones.

Method 2. The substituted 2-aminopyridine and substituted aldehyde in equimolar concentration were heated in refluxing m-xylene until 90–95% of the theoretical amount of H$_2$O was collected in a Dean-Stark trap. After the m-xylene was evaporated at atmospheric pressure, the residue was distilled in vacuo to afford 2-arylideneaminopyridine. The 2-arylideneaminopyridine and Et$^3$N were dissolved in anhydrous Et$_2$OP; a solution of chloroacetyl chloride in anhydrous Et$_2$O was then added dropwise with stirring at −15 to −10° C. After the addition was complete, the mixture wa stirred for 1 hour. The precipitated triethylamine chloride was filtered, and the filtrate was concentrated in vacuo. The residue was chromatographed on silica gel with CH$_2$Cl$_2$-EtOAc as eluant to give 2-phenyl-pyrido[1,2-a]pyrimidin-4-one, which was converted to the corresponding 2-phenyl-1,8-naphthyridin-4-one according to the procedures described in Method

EXAMPLE 3

Data Regarding Specific 2-Phenyl-pyrido[1,2, a] pyrimidin-4-ones (Compounds 7–38)

2-(2'-Methoxyphenyl)-pyrido[1,2-a]pyrimidin-4-one (7) is obtained from ethyl 2'-methoxybenzoylacetate and 2-aminopyridine.
Characteristics: needles;, mp 148–149° C.; $^1$H NMR (CDCl$_3$) δ 9.08 (d, J=7.0 Hz, 1 H, H-6), 7.98 (dd, J=7.5, 1.5 Hz, 1 H, H-6'), 7.78 (d, J=7.0 Hz, 1 H, H-9), 7.74 (t, J=7.0 Hz, 1 H, H-8), 7.44 (td, J=7.5, 1.5 Hz, 1 H, H-4'), 7.15 (s, 1 H, H-3), 7.14 (t, J=7.5 Hz, 1 H, H-5'), 7.12 (t, J=7.0 Hz, 1 H-7), 7.04 (br. d, J=8.5 Hz, 1 H, H-3'), 3.92 (s, 3 H, OCH$_3$-2'). MS m/z 252 (M$^+$).

2-(2'-Methoxyphenyl)-8-methyl-pyrido[1,2-a]pyrimidin-4-one (8) is obtained from ethyl 2'-methoxybenzoylacetate and 2-amino-4-picoline.
Characteristics: prisms; mp 154–155° C.; $^1$H NMR (CDCl$_3$) δ 8.96 (d, J=7.0 Hz, 1 H, H-6), 7.95 (dd, J=7.5, 1.5 Hz, 1 H, H-6'), 7.57 (br. s, 1 H, H-9), 7.44 (td, J=7.5, 1.5 Hz, 1 H, H-4'), 7.09 (t, J=7.5 Hz, 1 H, H-5'), 7.05 (s, 1 H, H-3), 7.02 (br. d, J=8.0 Hz, 1 H, H-7), 6.97 (dd, J=7.5, 1.5 Hz, 1 H, H-3'), 3.90 (s, 3 H, OCH$_3$-2'), 2.49 (s, 3 H, CH$_3$-8). MS m/z 266 (M$^+$).

2-(2'-Methoxyphenyl)-7-methyl-pyrido[1,2-a]pyrirmidin-4-one (9) is obtained from ethyl 2'-methoxybenzoylacetate and 2-amino-5-picoline.
Characteristics: prisms; mp 148–149° C.; $^1$H NMR (CDCl$_3$) δ 8.89 (s, 1 H, H-6), 7.96 (dd, J=7.9, 1.9 Hz, 1 H, H-6'), 7.74 (d, J=9.0 Hz, 1 H, H-9), 7.60 (dd, J=9.0, 2.0 Hz, 1 H, H-8), 7.44 (td, J=7.9, 1.9 Hz, 1 H, H-4'), 7.12 (s, 1 H, H-3), 7.10 (dt, J=7.9 1.9 Hz, 1 H, H-5'), 7.03 (d, J=7.9, Hz, 1 H, H-3'), 3.91 (s, 3 H, OCH$_3$-2'), 2.45 (s, 3 H, CH$_3$-7). MS m/z 266 (M$^+$).

2-(2'-Methoxyphenyl)-6-methyl-pyrido[1,2-a]pyrimidin-4-one (10) is obtained from ethyl 2'-methoxybenzoylacetate and 2-amino-6-picoline.
Characteristics: prisms; mp 153–154° C.; $^1$H NMR (CDCl$_3$) δ 7.99 (dd, J=7.5, 1.7 Hz, 1 H, H-6'), 7.52 (d, J=9.0 Hz, 1 H, H-9), 7.42 (t, J=9.0, Hz, 1 H, H-8), 7.42 (td, J=7.5, 1.7 Hz, 1 H, H-4'), 7.09 (t, J=7.5 Hz, 1 H, H-5'), 7.01 (d, J=7.5, Hz, 1 H, H-3'), 6.97 (s, 1 H, H-3), 6.64 (d, J=9.0 Hz, 1 H, H-7), 3.91 (s, 3 H, OCH$_3$-2'), 3.09 (s, 3 H, CH$_3$-6). MS m/z 266 (M$^+$).

2-(2'-Methoxyphenyl)-6,8-dimethyl-pyrido[1,2-a]pyrimidin-4-one (11) is obtained from ethyl 2'-methoxybenzoylacetate and 2-amino-4,6-dimethylpyridine. Characteristics: prisms; mp 170–171° C.; $^1$H NMR (CDCl$_3$) δ 7.96 (dd, J=7.5, 1.7 Hz, 1 H, H-6'), 7.41 (td, J=7.5, 1.7 Hz, 1 H, H-4'), 7.33 (br. s, 1 H, H-9), 7.08 (t, J=7.5 Hz, 1 H, H-5'), 7.01 (d, J=7.5, Hz, 1 H, H-3'), 6.88 (s, 1 H, H-3), 6.49 (br. s, 1 H, H-7), 3.90 (s, 3 H, OCH$_3$-2'), 3.06 (s, 3 H, CH$_3$-6), 2.34 (s, 3 H, CH$_3$-8). MS m/z 280 (M$^+$).

2-(3'-Methoxyphenyl)-pyrido[1,2-a]pyrimidin-4-one (12) is obtained from ethyl 3'-methoxybenzoylacetate and 2-aminopyridine.
Characteristics: prisms; mp 156–157° C.; $^1$H NMR (CDCl$_3$) δ 9.08 (d, J=7.0 Hz, 1 H, H-6), 7.76 (d, J=7.0 Hz, 1 H, H-9), 7.75 (t, J=7.0 Hz, 1 H, H-8), 7.67 (s, 1 H, H-2'), 7.66 (d, J=7.5, Hz, 1 H, H-6'), 7.42 (t, J=7.5 Hz, 1 H, H-5'), 7.15 (ddd, J=7.0, 7.0, 2.0 Hz, 1 H, H-7), 7.05 (td, J=7.5 Hz, 1 H, H-4'), 6.92 (s, 1 H, H-3), 3.92 (s, 3 H, OCH$_3$-3'). MS m/z 252 (M$^+$).

2-(3'-Methoxyphenyl)-8-methyl-pyrido[1,2-a]pyrimidin-4-one (13) is obtained from ethyl 3'-methoxybenzoylacetate and 2-amino-4-picoline.
Characteristics: plates; mp 136–137° C.; $^1$H NMR (CDCl$_3$) δ 8.97 (d, J=7.0 Hz, 1 H, H-6), 7.66 (br. s, 1 H, H-2'), 7.64 (d, J=7.5, 1 H, H-6'), 7.54 (s, 1 H, H-9), 7.41 (t, J=7.5 Hz, 1 H, H-5'), 7.04 (dd, J=7.5, 2.0 Hz, 1 H, H-4'), 6.98 (d, J=7.0 Hz, 1 H, H-7), 6.85 (s, 1 H, H-3), 3.91 (s, 3 H, OCH$_3$-3'), 2.51 (s, 3 H, CH$_3$-8) 266 (M$^+$).

2-(3'-Methoxyphenyl)-7-methyl-pyrido[1,2-a]pyrimidin-4-one (14) is obtained from ethyl 3'-methoxybenzoylacetate and 2-amino-5-picoline.
Characteristics: prisms; mp 163–164° C.; $^1$H NMR (CDCl$_3$) δ 8.90 (s, 1 H, H-6), 7.70 (d, J=9.0 Hz, 1 H, H-9), 7.66 (d, J=2.0 Hz, 1 H, H-2'), 7.65 (d, J=7.8 Hz, 1 H, H-6'), 7.62 (dd, J=9.0, 1.8 Hz, 1 H, H-8), 7.42 (t, J=7.8, Hz, 1 H, H-5'), 7.04 (td, J=7.8, 2.0 Hz, 1 H, H-4'), 6.90 (s, 1 H, H-3), 3.91 (s, 3 H, OCH$_3$-3'), 2.46 (s, 3 H, CH$_3$-7). MS m/z 266 (M$^+$).

2-(3'-Methoxyphenyl)-6-methyl-pyrido[1,2-a]pyrimidin-4-one (15) is obtained from ethyl 3'-methoxybenzoylacetate and 2-amino-6-picoline.
Characteristics: prisms; mp 115–116° C.; $^1$H NMR (CDCl$_3$) δ 7.63 (s, 1 H, H-2'), 7.61 (d, J=7.5 Hz, 1 H, H-6'), 7.49 (d, J=8.5, Hz, 1 H, H-9), 7.45 (dd, J=8.5, 6.3 Hz, 1 H, H-8), 7.39 (t,J=7.5 Hz, 1 H, H-5'), 7.02 (td, J=7.5, 2.0 Hz, 1 H, H-4'), 6.72 (s, 1 H, H-3), 6.64 (d, J=6.3 Hz, 1 H, H-7), 3.90 (s, 3 H, OCH$_3$-3') (s, 3 H, CH$_3$-6). MS m/z 266 (M$^+$).

2-(3'-Methoxyphenyl)-6,8-dimethyl-pyrido[1,2-a]pyrimidin-4-one (16) is obtained from ethyl 3'-methoxybenzoylacetate and 2-amino-4,6-dimethylpyridine. Characteristics: prisms; mp 139–140° C.; $^1$H NMR (CDCl$_3$) δ 7.61 (br. s, 1 H, H-2'), 7.60 (d, J=7.5, Hz, 1 H, H-6'), 7.38 (t, J=7.5 Hz, 1 H, H-5'), 7.28 (br. s, 1 H, H-9), 7.01 (dd, J=7.5, 2.0 Hz, 1 H, H-4'), 6.64 (s, 1 H, H-3) 6.49 (br. s, 1 H, H-7), 3.89(s, 3 H, OCH$_3$-3'), 3.05 (s, 3 H, CH$_3$-6), 2.34 (s, CH$_3$-8). MS m/z 280 (M$^+$).

2-(3'-Methoxyphenyl)-7-chloro-pyrido[1,2-a]pyrimidin-4-one (17) is obtained from ethyl 3'-methoxybenzoylacetate and 2-amino-5-chloropyridine.
Characteristics: needles; mp 172–173° C.; $^1$H NMR (CDCl$_3$) δ 9.08 (d, J=1.5 Hz, 1 H, H-6), 7.67 (br. d, 1 H, H-2'), 7.66 (d, J=10.0 Hz, 1 H, H-8), 7.65 (d, J=10.0 Hz, 1 H, H-9), 7.63 (d, J=7.7 Hz, 1 H, H-4'), 7.41 (t, J=7.7, Hz, 1 H, H-5'), 7.05 (dd, J=7.7, 2.0 Hz, 1 H, H-6'), 6.92 (s, 1 H, H-3), 3.91 (s, 3 H, OCH$_3$-3'). MS m/z 286 (M$^+$).

2-(3'-Methoxyphenyl)-7-bromo-pyrido[1,2-a]pyrimidin-4-one (18) is obtained from ethyl 3'-methoxybenzoylacetate and 2-amino-5-bromopyridine.
Characteristics: needles; mp 197–198° C.; $^1$H NMR (CDCl$_3$) δ 8.19 (d, J=2.0 Hz, 1 H, H-6), 7.77 (dd, J=9.5, 2.0

Hz, 1 H, H-8), 7.64 (br. s, 1 H, H-2'), 7.63 (d, J=7.7 Hz, 1 H, H-4'), 7.62 (dd, J=9.0, 2.0 Hz, 1 H, H-9), 7.42 (t, J=7.7, Hz, 1 H, H-5'), 7.05 (dd, J=7.7, 2.0 Hz, 1 H, H-6'), 6.93 (s, 1 H, H-3), 3.91 (s, 3 H, $OCH_3$-3'). MS m/z 330 ($M^+$, 97%), 332 ($M^+$+2, 92%).

2-(4'-Methoxyphenyl)-pyrido[1,2-a]pyrimidin-4-one (19) is obtained from ethyl 4'-methoxybenzoylacetate and 2-aminopyridine.

Characteristics: needles; mp 153–154° C.; $^1$H NMR ($CDCl_3$) δ 9.07(d, J=7.2 Hz, 1 H, H-6), 8.09 (d, J=9.0 Hz, 2 H, $H_2$-2',6'), 7.76 (d, J=4.0 Hz, 2 H, $H_2$-8,9), 7.12 (dd, J=7.2, 4.0 Hz, 1 H, H-7), 7.04 (d, J=9.0 Hz, 2 H, $H_2$-3'5'), 6.88 (s, 1 H, H-3), 3.90(s, 3H, $OCH_3$-4'). MS m/z 252 ($M^+$).

2-(4'-Methoxyphenyl)-8-methyl-pyrido[1,2-a]pyrimidin-4-one (20) is obtained from ethyl 4'-methoxybenzoylacetate and 2-amino-4-picoline.

Characteristics: needles; mp 167–168° C.; $^1$H NMR ($CDCl_3$) δ 8.96 (d, J=7.2 Hz, 1 H, H-6), 8.08 (d, J=8.8 Hz, 2 H, $H_2$-2',6'), 7.55(br. s, 1 H, H-9), 7.02 (d, J=8.8 Hz, 2 H, $H_2$-3', 5'), 6.96 (dd, J=7.2, 1.7 Hz, 1 H, H-7), 6.79 (s, 1 H, H-3), 3.89 (s, 3 H, $OCH_3$-4'), 2.51 (s, 3 H, $CH_3$-8). MS m/z 266 ($M^+$).

2-(4'-Methoxyphenyl)-7-methyl-pyrido[1,2-a]pyrimidin-4-one (21) is obtained from ethyl 4'-methoxybenzoylacetate and 2-amino-5-picoline.

Characteristics: prisms; mp 197–198° C.; $^1$H NMR ($CDCl_3$) δ 8.87 (s, 1 H, H-6), 8.07 (d, J=8.8 Hz, 2 H, $H_2$-2', 6'), 7.67 (d, J=9.0 Hz, 1 H, H-9), 7.60(dd, J=9.0, 2.0 Hz, 1 H, H-8), 7.02 (d, J=8.8 Hz, 2 H, $H_2$-3',5'), 6.85 (s, 1 H, H-3), 3.89 (s, 3 H, $OCH_3$-4'), 2.44 (s, 3 H, $CH_3$-7). MS m/z 266 ($M^+$).

2-(4'-Methoxyphenyl)-6-methyl-pyrido[1,2-a]pyrirnidin-4-one (22) is obtained from ethyl 4'-methoxybenzoylacetate and 2-amino-6-picoline.

Characteristics: prisms; mp 143–144° C.; $^1$H NMR ($CDCl_3$) δ 8.05 (d, J=9.0 Hz, 2 H, $H_2$-2', 6'), 7.48 (dd, J=8.7, 1.4 Hz, 1 H, H-9), 7.42 (dd, J=6.8, 8.7 Hz, 1 H, H-8), 7.00 (d, J=9.0 Hz, 2 H, $H_2$-3', 5'), 6.67 (s, 1 H, H-3), 6.62 (d, J=6.8 H-7), 3.88 (s, 3 H, $OCH_3$-4'), 3.08 (s, 3 H, $CH_3$-6). MS m/z 266 ($M^+$).

2-(4'-Methoxyphenyl)-6,8-dimethyl-pyrido[1,2-a]pyrimidin-4-one (23) is obtained from ethyl 3'-methoxybenzoylacetate and 2-amino-4,6-dimethylpyridine. Characteristics: amorphous; mp 187–188° C.; $^1$H NMR ($CDCl_3$) δ 8.03 (d, J=9.0 Hz, 2 H, $H_2$-2', 6'), 7.28 (br. s, 1 H, H-9), 7.00 (d, J=9.0 Hz, 2 H, $H_2$-3', 5'), 6.60 (s, 1 H, H-3), 6.48 (br. s, 1 H, H-7), 3.88 (s, 3 H, $OCH_3$-4'), 3.06 (s, 3 H, $CH_3$-6), 2.35 (s, 3H, $CH_3$-8). MS m/z 280 ($M^+$).

2-(4'-Fluorophenyl)-pyrido[1,2-a]pyrimidin-4-one (24) is obtained from ethyl 4'-fluorobenzoylacetate and 2-aminopyridine. Characteristics: needles; mp 193–195° C.; $^1$H NMR ($CDCl_3$) δ 9.08 (d, J=7.2 Hz, 1 H, H-6), 8.12 (dd, J=8.8, 5.2 Hz, 2 H, $H_2$-2', 6'), 7.79 (dd, J=9.0, 1.5 Hz, 1 H, H-9), 7.75 (dd, J=9.0 6.5 Hz, 1 H, H-8), 7.20 (t, J=8.8 Hz, 2 H, $H_2$-3', 5'), 6.88 (s, 1 H, H-3). MS m/z 240 ($M^+$).

2-(4'-Fluorophenyl)-8-methyl-pyrido[1,2-a]pyrimidin-4-one (25) is obtained from ethyl 4'-fluorobenzoylacetate and 2-amino-4-picoline.

Characteristics: amorphous; mp 191–193° C.; $^1$H NMR ($CDCl_3$) δ 8.97 (d, J=7.3Hz, 1 H, H-6), 8.10 (dd, J=8.8, 5.7 Hz, 2 H, $H_2$-2', 6'), 7.53 (br. s, 1 H, H-9), 7.19 (t, J=8.8 Hz, 2 H, $H_2$-3', 5'), 6.99 (dd, J=7.3, 2.0 Hz, 1 H, H-7), 6.80 (s, 1 H, H-3), 2.52 (s, 3 H, $CH_3$-8). MS m/z 254 ($M^+$).

2-(4'-Fluorophenyl)-7-methyl-pyrido[1,2-a]pyrimidin-4-one (26) is obtained from ethyl 4'-fluorobenzoylacetate and 2-amino-5-picoline.

Characteristics: amorphous; mp 174–175° C.; $^1$H NMR ($CDCl_3$) δ 8.89 (s, 1 H, H-6), 8.10 (dd, J=8.8, 5.7 Hz, 2 H, $H_2$-2', 6'), 7.67 (d, J=9.0 Hz, 1 H, H-9), 7.63 (dd, J=9.0, 2.0 Hz, 1 H, H-8), 7.19 (t, J=8.8 Hz, 2 H, $H_2$-3', 5'), 6.85 (s, 1 H, H-3), 2.46 (s, 3 H, $CH_3$-7). MS m/z 254 ($M^+$).

2-(4'-Fluorophenyl)-6-methyl-pyrido[1,2-a]pyrimidin-4-one (27) is obtained from ethyl 4'-fluorobenzoylacetate and 2-amino-6-picoline.

Characteristics: prisms, mp 179–181° C.; $^1$H NMR ($CDCl_3$) δ 8.07 (dd, J=8.8, 5.2 Hz, 2 H, $H_2$-2', 6'), 7.48 (dd, J=8.5, 2.0 Hz, 1 H, H-9), 7.44 (dd, J=8.5, 6.5 Hz, 1 H, H-8), 7.17 (t, J=8.8 Hz, 2 H, $H_2$-3', 5'), 6.67 (s, 1 H, H-3), 6.64 (dd, J=6.5, 2.0 Hz, 1 H, H-7), 3.09 (s, 3 H, $CH_3$-6). MS m/z 254 ($M^+$).

2-(4'-Fluorophenyl)-6,8-dimethyl-pyrido[1,2-a]pyrimidin-4-one (28) is obtained from ethyl 3'-fluorobenzoylacetate and 2-amino-4,6-dimethylpyridine. Characteristics: prisms; mp 199–201° C.; $^1$H NMR ($CDCl_3$) δ 8.05 (dd, J=8.7, 5.3 Hz, 2 H, $H_2$-2', 6'), 7.27 (br. s, 1 H, H-9), 7.16 (t, J=8.7 Hz, 2 H, $H_2$-3', 5'), 6.61(s, 1 H, H-3), 6.51 (br. s, 1 H, H-7), 3.06 (s, 3 H, $CH_3$-6), 2.36 (s, 3 H, $CH_3$-8). MS m/z 268 ($M^+$).

2-(4'-Fluorophenyl)-7-chloro-pyrido[1,2-a]pyrmidin-4-one (29) is obtained from ethyl 4'-fluorobenzoylacetate and 2-amino-5-chloropyridine.

Characteristics: prisms; mp 187–189° C.; $^1$H NMR ($CDCl_3$) δ 9.09 (s, 1 H, H-6), 8.10 (dd, J=8.7, 5.6 Hz, 2 H, $H_2$-2', 6'), 7.70 (dd, J=9.0, 2.0 Hz, 1 H, H-8), 7.67 (d, J=9.0 Hz, 1 H, H-9), 7.20 (t, J=8.7 Hz, 2 H, $H_2$-3', 5'), 6.89 (s, 1 H, H-3). MS m/z 274 ($M^+$).

2-(4'-Chlorophenyl)-pyrido[1,2-a]pyrimidin-4-one (30) is obtained from ethyl 4'-chlorobenzoylacetate and 2-aminopyridine. Characteristics: amorphous; mp 202–203° C.; $^1$H NMR ($CDCl_3$) δ 9.10 (d, J=7.0 Hz, 1 H, H-6), 8.07 (d, J=8.5 Hz, 2 H, $H_2$-2', 6'), 7.90 (d, J=9.0 Hz, 1 H, H-9), 7.83 (dd, J=9.0, 6.5 Hz, 1 H, H-8), 7.50 (d, J=8.5 Hz, 2 H, $H_2$-3'5'), 7.21 (dd, J=7.0, 6.5 Hz, 1 H, H-7), 6.88 (s, 1 H, H-3). MS m/z 256 ($M^+$).

2-(4'-Chlorophenyl)-8-methyl-pyrido[1,2-a]pyrimidin-4-one (31) is obtained from ethyl 4'-chlorobenzoylacetate and 2-amino-4-picoline.

Characteristics: needles; mp 211–213° C.; $^1$H NMR ($CDCl_3$) δ 8.98 (d, J=7.3 Hz, 1 H, H-6), 8.04 (d, J=8.5 Hz, 2 H, $H_2$-2', 6'), 7.56 (br. s, 1 H, H-9), 7.48 (d, J=8.5 Hz, 2H, $H_2$-3', 5'), 7.00 (dd, J=7.3, 1.0 Hz, 1 H, H-7), 6.81 (s, 1 H, H-3), 2.53 (s, 3 H, $CH_3$-8). MS m/z 270 ($M^+$).

2-(4'-Chlorophenyl)-7-methyl-pyrido[1,2-a]pyrimidin-4-one (32) is obtained from ethyl 4'-chlorobenzoylacetate and 2-amino-5-picoline.

Characteristics: needles; mp 195–196° C.; $^1$H NMR ($CDCl_3$) δ 8.90 (s, 1 H, H-6), 8.05 (d, J=8.6 Hz, 1 H, $H_2$-2', 6'), 7.77 (d, J=8.9 Hz, 1 H, H-9), 7.67 (dd, J=8.9, 1.5 Hz, 1 H, H-8), 7.48 (d, J=8.6 Hz, 2 H, $H_2$-3', 5'), 6.86 (s, 1 H, H-3), 2.47 (s, 3 H, $CH_3$-7). MS m/z 270 ($M^+$).

2-(4'-Chlorophenyl)-6-methyl-pyrido[1,2-a]pyrimidin-4-one (33) is obtained from ethyl 4'-chlorobenzoylacetate and 2-amino-6-picoline.

Characteristics: needles; mp 154–156° C.; $^1$H NMR ($CDCl_3$) δ 8.02 (d, J=8.5 Hz, 2 H, $H_2$-2', 6'), 7.51 (d, J=8.5 Hz, 1 H, H-9), 7.47 (d, J=8.5 Hz, 2 H, $H_2$-3', 5'), 7.46 (dd, J=8.5, 6.3 Hz, 1 H, H-8), 6.69 (s, 1 H, H-3), 6.67 (d, J=6.3 Hz, 1 H, H-7), 3.09 (s, 3 H, $CH_3$-6). MS m/z 266 ($M^+$).

2-(4'-Chlorophenyl)-6,8-dimethyl-pyrido[1,2-a]pyrimidin-4-one (34) is obtained from ethyl 3'-chlorobenzoylacetate and 2-amino-4,6-dimethylpyridine. Characteristics: needles; mp 210–212° C. (decomposed); $^1$H NMR ($CDCl_3$) δ 8.01 (d, J=8.5 Hz, 2 H, $H_2$-2', 6'), 7.46 (d, J=8.5 Hz, 2 H, $H_2$-3', 5'), 7.27 (s, 1 H, H-9), 6.61 (s, 1 H, H-3), 6.57 (s, 1 H, H-7), 3.07 (s, 3 H, $CH_3$-6), 2.39 (s, 3 H, $CH_3$-8). MS m/z 284 ($M^+$).

2-(4'-Methylphenyl)-8-methyl-pyrido[1,2-a]pyrimidin-4-one (35) is obtained from ethyl 4'-methylbenzoylacetate and 2-amino-4-picoline.

Characteristics: prisms; mp 176–177° C.; $^1$H NMR (CDCl$_3$) δ 8.96 (d, J=7.3 Hz, 1 H, H-6), 7.99 (d, J=8.2 Hz, 2 H, H$_2$-2', 6'), 7.54 (br. s, 1 H, H-9), 7.31 (d, J=8.2 Hz, 2 H, H$_2$-3', 5'), 6.96 (dd, J=7.3, 1.5 Hz, 1 H, H-7), 6.83 (s, 1 H, H-3), 2.50 (s, 3 H, CH$_3$-8), 2.43 (s, 3 H, CH$_3$-4'). MS m/z 250 (M$^+$).

2-(4'-Methylphenyl)-7-methyl-pyrido[1,2-a]pyrimidin-4-one (36) is obtained from ethyl 4'-methylbenzoylacetate and 2-amino-5-picoline.

Characteristics: prisms; mp 171–172° C.; $^1$H NMR (CDCl$_3$) δ 8.88 (s, 1 H, H-6), 7.99 (d, J=8.2 Hz, 2 H, H$_2$-2', 6'), 7.68 (d, J=9.0 Hz, 1 H, H-9), 7.60 (dd, J=9.0, 2.0 Hz, 1 H, H-8), 7.31 (d, J=8.2 Hz, 2 H, H$_2$-3', 5'), 6.88 (s, 1 H, H-3), 2.44 (s, 3 H, CH$_3$-7), 2.43 (s, 3 H, CH$_3$-4'). MS m/z 250 (M$^+$).

2-(4'-Methylphenyl)-6-methyl-pyrido[1,2-a]pyrimidin-4-one (37) is obtained from ethyl 4'-methylbenzoylacetate and 2-amino-6-picoline.

Characteristics: prisms; mp 140–141° C.; $^1$H NMR (CDCl$_3$) δ 7.97 (d, J=8.2 Hz, 2 H, H$_2$-2', 6'), 7.50 (d, J=8.3 Hz, 1 H, H-9), 7.42 (dd, J=8.3, 6.5 Hz, 1 H, H-8), 7.30 (d, J=8.2 Hz, 2 H, H$_2$-3', 5'), 6.71 (s, 1 H, H-3), 6.64 (d, J=6.5 Hz, 1 H, H-7), 3.08 (s, 3 H, CH$_3$-6), 2.42 (s, 3 H, CH$_3$-4'). MS m/z 250 (M$^+$).

2-(4'-Methylphenyl)-6,8-dimethyl-pyrido[1,2-a]pyrimidin-4-one (38) is obtained from ethyl 3'-methylbenzoylacetate and 2-amino-4,6-dimethylpyridine. Characteristics: amorphous; mp 196–198° C.; $^1$H NMR (CDCl$_3$) δ 7.95 (d, J=8.2 Hz, 2 H, H$_2$-2', 6'), 7.30 (s, 1 H, H-9), 7.29 (d, J=9.0 Hz, 2 H, H$_2$-3', 5'), 6.64 (s, 1 H, H-3), 6.49 (s, 1 H, H-7), 3.06 (s, 3 H, CH$_3$-6), 2.42 (s, 3 H, CH$_3$-4'), 2.35 (s, 3 H, CH$_3$-8). MS m/z 264 (M$^+$).

EXAMPLE 4

Data Regarding Specific 2-phenyl-1,8-naphthyridin-4-ones (Compounds 39–70)

2-(2'-Methoxyphenyl)-1,8-naphthyridin-4-one (39) is obtained from compound (7). Characteristics: plates; $^1$H NMR (CDCl$_3$) δ 8.65 (d, J=8.0 Hz, 1 H, H-5), 8.62 (d, J=4.5 Hz, 1 H, H-7), 7.64 (dd, J=8.0, 1.7 Hz, 1 H, H-6'), 7.49 (td, J=8.0, 1.7 Hz, 1 H, H-4'), 7.34 (dd, J=8.0, 4.5 Hz, 1 H, H-6), 7.10 (t, J=8.0 Hz, 1 H, H-5'), 7.06 (d, J=8.0 Hz, 1 H, H-3'), 6.62 (s, 1 H, H-3), 3.94 (s, 3 H, OCH$_3$-2'). MS m/z 252 (M$^+$). Elemental Analysis: calculated C 7.42, H 4.79, N 11.10; found C 71.27, H 4.86, N 11.02.

2-(2'-Methoxyphenyl)-5-methyl-1,8-naphthyridin-4-one (40) is obtained from compound (8). Characteristics: needles; $^1$H NMR (CDCl$_3$) δ 10.45, (br. s, 1 H, NH-1), 8.19 (d, J=5.0 Hz, 1 H, H-7), 7.65 (dd, J=7.5, 1.0 Hz, 1 H, H-6'), 7.50 (td, J=7.5, 1.0 Hz, 1 H, H-4'), 7.13 (t, J=7.5 Hz, 1 H, H-5'), 7.04 (d, J=7.5 Hz, 1 H, H-3'), 6.98 (d, J=5.0 Hz, 1 H, H-6), 6.56 (s, 1 H, H-3), 3.89 (s, 3 H, OCH$_3$-2'), 2.99 (s, 3 H, CH$_3$-5). MS m/z 266 (M$^+$). Elemental Analysis: calculated C 72.17, H 5.30, N 10.52; found C 72.21, H 5.33, N 10.38.

2-(2'-Methoxyphenyl)-6-methyl-1,8-naphthyridin-4-one (41) is obtained from compound (9). Characteristics: needles; $^1$H NMR (CDCl$_3$) δ 11.19, (br. s, 1 H, NH-1), 8.48 (d, J=1.8 Hz, 1 H, H-5), 8.01 (d, J=1.8 Hz, 1 H, H-7), 7.62 (dd, J=8.0, 1.7 Hz, 1 H, H-6'), 7.52 (td, J=8.0, 1.7 Hz, 1 H, H-4'), 7.13 (t, J=8.0 Hz, 1 H, H-5'), 7.01 (d, J=8.0 Hz, 1 H, H-3'), 6.59 (s, 1 H, H-3), 3.78 (s, 3 H, OCH$_3$-2'), 2.40 (s, 3 H, CH$_3$-6). MS m/z 266 (M$^+$). Elemental Analysis: calculated C 72.17, H 5.30, N 10.52; found C 72.03, H 5.42, N 10.59.

2-(2'-Methoxyphenyl)-7-methyl-1,8-naphthyridin-4-one (42) is obtained from compound (10). Characteristics: needles; $^1$H NMR (CDCl$_3$) δ 10.66, (br. s, 1 H, NH-1), 8.57 (d, J=8.0 Hz, 1 H, H-5), 7.63 (dd, J=7.5, 1.5 Hz, 1 H, H-6'), 7.49 (td, J=7.5, 1.5 Hz, 1 H, H-4'), 7.15 (d, J=8.0 Hz, 1 H, H-6), 7.12 (t, J=7.5 Hz, 1 H, H-5'), 6.95 (d, J=7.5 Hz, 1 H, H-3'), 6.59 (s, 1 H, H-3) 3.73 (s, 3 H, OCH$_3$-2'), 2.42 (s, 3 H, CH$_3$-7). MS m/z 266(M$^+$). Elemental Analysis: calculated C 72.17, H 5.30, N 10.52; found C 72.10, H 5.51, N 10.29.

2-(2'-Methoxyphenyl)-5,7-dimethyl-1,8-naphthyridin-4-one (43) is obtained from compound (11). Characteristics: prisms; $^1$H NMR (CDCl$_3$) δ 7.62 (dd, J=7.5, 1.5 Hz, 1 H, H-6'), 7.47 (td, J=7.5, 1.5 Hz, 1 H, H-4'), 7.10 (t, J=7.5 Hz, 1 H, H-5'), 6.95 (d, J=7.5 Hz, 1 H, H-3'), 6.84 (s, 1 H, H-6), 6.50 (s, 1 H, H-3), 3.77 (s, 3 H, OCH$_3$-2'), 2.95 (s, 3 H, CH$_3$-5), 2.35 (s, 3 H, CH$_3$-7). MS m/z 280 (M$^+$). Elemental Analysis: calculated C 71.69, H 5.84, N 9.84; found C 71.81, H 5.98, N 9.92.

2-(3'-Methoxyphenyl)-1,8-naphthyridin-4-one (44) is obtained from compound (12). Characteristics: amorphous; $^1$H NMR (CDCl$_3$) δ 11.10, (br. s, 1 H, NH-1), 8.70 (dd, J=8.0, 1.5 Hz, 1 H, H-5), 8.10 (dd, J=4.5, 1.5 Hz, 1 H, H-7), 7.45 (t, J=8.0 Hz, 1 H, H-5'), 7.31 (d, J=8.0 Hz, 1 H, H-6'), 7.26 (br. s, 1 H, H-2'), 7.24 (dd, J=8.0, 4.5 Hz, 1 H, H-6), 7.10 (dd, J=8.0, 2.0 Hz, 1 H, H-4'), 6.60 (s, 1 H, H-3), 3.85 (s, 3 H, OCH$_3$-3'). MS m/z 252 (M$^+$). Elemental Analysis: calculated C 71.42, H 4.79, N 11.10; found C 71.31, H 4.84, N 11.07.

2-(3'-Methoxyphenyl)-5-methyl-1,8-naphthyridin-4-one (45) is obtained from compound (13). Characteristics: plates; $^1$H NMR (CDCl$_3$) δ 10.74, (br. s, 1 H, NH-1), 7.84 (d, J=5.0 Hz, 1 H, H-7), 7.43 (t, J=8.0 Hz, 1 H, H-5'), 7.29 (d, J=8.0 Hz, 1 H, H-6'), 7.22 (t, J=2.5 Hz, 1 H, H-2'), 7.09 (dd, J=8.0, 2.5 Hz, 1 H, H-4'), 6.93 (d, J=5.0 Hz, 1 H, H-6), 6.52 (s, 1 H, H-3), 3.85 (s, 3 H, OCH$_3$-3'), 2.97 (s, 3 H, CH$_3$-5). MS m/z 266 (M$^+$). Elemental Analysis: calculated: C 72.17, H 5.30, N 10.52; found C 72.01, H 5.43, N 10.39.

(3'-Methoxyphenyl)-6-methyl-1,8-naphthyridin-4-one (46) is obtained from compound (14). Characteristics: amorphous; $^1$H NMR (CDCl$_3$) δ 10.75, (s, 1 H, NH-1), 8.49 (d, J=2.0 Hz, 1 H, H-5), 8.00 (d, J=2.0 Hz, 1 H, H-7), 7.46 (t, J=8.0 Hz, 1 H, H-5'), 7.29 (d, J=8.0 Hz, 1 H, H-6'), 7.23 (t, J=1.8 Hz, 1 H, H-2'), 7.11 (dd, J=8.0, 1.8 Hz, 1 H, H-4'), 6.58(s, 1 H, H-3), 3.85 (s, 3 H, OCH$_3$-3'), 2.39 (s, 3 H, CH$_3$-6). MS m/z 266 (M$^+$). Elemental Analysis: calculated C 72.17, H 5.30, N 10.52; found C 72.32, H 5.51, N 10.41.

2-(3'-Methoxyphenyl)-7-methyl-1,8-naphthyridin-4-one (47) is obtained from compound (15). Characteristics: amorphous; $^1$H NMR (CDCl$_3$) δ 9.13, (br. s, 1 H, NH-1), 8.57 (d, J=8.0 Hz, 1 H, H-5), 7.45 (t, J=8.0 Hz, 1 H, H-5'), 7.26 (d, J=8.0 Hz, 1 H, H-6'), 7.21 (d, J=8.0 Hz, 1 H, H-6), 7.20 (s, 1 H, H-2'), 7.08 (d, J=8.0 Hz, 1 H, H-4'), 6.60 (s, 1 H, H-3), 3.88 (s, 3 H, OCH$_3$-3'), 2.60 (s, 3 H, CH$_3$-7). MS m/z 266 (M$^+$). Elemental Analysis: calculated C 72.17, H 5.30, N 10.52; found C 72.28, H 5.49, N 10.36.

2-(3'-Methoxyphenyl)-5,7-dimethyl-1,8-naphthyridin-4-one (48) is obtained from compound (16). Characteristics: prisms; $^1$H NMR (CDCl$_3$) δ 9.42, (br. s, 1 H, NH-1), 7.40 (t, J=8.0 Hz, 1 H, H-5'), 7.22 (d, J=8.0 Hz, 1 H, H-6'), 7.15 (t, J=2.0 Hz, 1 H, H-2'), 7.05 (dd, J=8.0, 2.0 Hz, 1 H, H-4'), 6.88 (s, 1 H, H-6), 6.50 (s, 1 H, H-3), 3.83 (s, 3 H, OCH$_3$-3'), 2.94 (s, 3 H, CH$_3$-5), 2.40 (s, 3 H, CH$_3$-7). MS m/z 280 (M$^+$). Elemental Analysis: calculated C 72.84, H 5.75, N 9.99; found C 72.62, H 5.91, N 9.87.

2-(3'-Methoxyphenyl)-6-chloro-1,8-naphthyridin-4-one (49) is obtained from compound (17); Characteristics: needles; $^1$H NMR (DMSO-d) δ 12.57, (s, 1 H, NH-1), 8.85 (d, J=2.7 Hz, 1 H, H-5), 8.44 (d, J=2.0 Hz, 1 H, H-7), 7.47 (t, J=8.0 Hz, 1 H, H-5'), 7.41 (d, J=8.0 Hz, 1 H, H-6'), 7.41 (br. s, 1 H, H-2'), 7.13 (br. d, J=8.0, Hz, 1 H, H-4'), 6.49 (s, 1 H, H-3), 3.87 (s, 3 H, OCH$_3$-3'). MS m/z 286 (N$^+$). Elemental Analysis: calculated C 58.93, H 4.62, N 9.16; found C 59.11, H 4.90, N 9.27.

2-(3'-Methoxyphenyl)-6-bromo-1,8-naphthyridin-4-one (50) is obtained from compound (18). Characteristics: amorphous; $^1$H NMR (DMSO-d$_6$) δ 12.54, (s, 1 H, NH-1), 8.90 (d, J=2.3 Hz, 1 H, H-5), 8.55 (d, J=2.3 Hz, 1 H, H-7), 7.46 (t, J=7.8 Hz, 1 H, H-5'), 7.42 (d, J=7.8 Hz, 1 H, H-6'), 7.41 (s, 1 H, 2'), 7.12 (br. d, J=7.8 Hz, 1 H, H-4'), 6.49 (s, 1 H, H-3), 3.87s, 3 H, OCH$_3$-3'). MS m/z 330 (M+, 100%), 332 (M$^+$+2, 94%). Elemental Analysis: calculated C 52.81, H 3.84, N 8.21; found C 52.97, H 4.08, N 8.02.

2-(4'-Methoxyphenyl)-1,8-naphthyridin-4-one (51) is obtained from compound (19). Characteristics: plates; $^1$H NMR (CDCl$_3$) δ 8.69 (dd, J=8.0, 2.0 Hz, 1 H, H-5), 8.35 (dd, J=5.2, 2.0 Hz, 1 H, H-7), 7.70 (d, J=8.8 Hz, 2 H, H$_2$-2', 6'), 7.30 (dd, J=8.0, 5.2 Hz, 1 H, H-6), 7.06 (d, J=8.8 Hz, 2 H, H$_2$-3', 5'), 6.61(s, 1 H, H-3), 3.91 (s, 3 H, OCH$_3$-4'). MS m/z 252 (M$^+$). Elemental Analysis: calculated C 71.42, H 4.79, N 11.10; found C 71.18, H 4.93, N 11.01.

2-(4'-Methoxyphenyl)-5-methyl-1,8-naphthyridin-4-one (52) is obtained from compound (20). Characteristics: plates; $^1$H NMR (CDCl$_3$) δ 8.09 (d, J=4.8 Hz, 1 H, H-7), 7.67 (d, J=8.8 Hz, 2 H, H$_2$-2', 6'), 7.05 (d, J=8.8 Hz, 2 H, H$_2$-3', 5'), 6.98 (d, J=4.8 Hz, 1 H, H-6), 6.51 (s, 1 H, H-3), 3.90 (s, 3 H 4'), 2.98 (s, 3 H, CH$_3$-5). MS m/z 266 (M$^+$). Elemental Analysis: calculated C 72.17, H 5.30, N 10.52; found C 72.35, H 5.62, N 10.73.

2-(4'-Methoxyphenyl)-6-methyl-1,8-naphthyridin-4-one (53) is obtained from compound (21). Characteristics: amorphous; $^1$H NMR (CDCl$_3$) δ 8.50 (s, 1 H, H-5), 8.30 (s, 1 H, H-7), 7.69 (d, J=8.7 Hz, 2 H, H$_2$-2', 6'), 7.07 (d, J=8.7 Hz, 2 H, H$_2$-3', 5'), 6.63 (s, 1 H, H-3), 3.90 (s, 3 H, OCH$_3$-4'), 2.45 (s, 3 H, CH$_3$-6). MS m/z 266 (M$^+$). Elemental Analysis: calculated C 72.17, H 5.30, N 10.52; found C 71.98, H 5.26, N 10.39.

2-(4'-Methoxyphenyl)-7-methyl-1,8-naphthyridin-4-one (54) is obtained from compound (22). Characteristics: amorphous; $^1$H NMR (CDCl$_3$) δ 8.60 (d, J=8.0 Hz, 1 H, H-5), 7.68(d, J=8.8 Hz, 2 H, H$_2$-2', 6'), 7.23 (d, J=8.0 Hz, 1 H, H-6), 7.07 (d, J=8.8 Hz, 2 H, H$_2$-3', 5'), 6.61 (s, 1 H, H-3), 3.90 (s, 3 H, OCH$_3$-4'), 2.67 (s, 3 H, CH$_3$-7). MS m/z 266 (M$^+$). Elemental Analysis: calculated C 72.17, H 5.30, N 10.52; found C 72.09, H 5.36, N 10.46.

2-(4'-Methoxyphenyl)-5,7-dimethyl-1,8-naphthyridin-4-one (55) is obtained from compound (23). Characteristics: amorphous; $^1$H NMR (CDCl$_3$) δ 7.62 (d, J=8.8 Hz, 2 H, H$_2$-2', 6'), 7.02 (d, J=8.8 Hz, 2 H, H$_2$-3', 5'), 6.89 (s, 1 H, H-6), 6.48 (s, 1 H, H-3), 3.88 (s, 3 H, OCH$_3$-4'), 2.94 (s, 3 H, CH$_3$-5), 2.47 (s, 3 H, CH$_3$-7). MS m/z 280 (M$^+$). Elemental Analysis: calculated C 70.57, H 5.92, N 9.68; found C 70.48, H 5.89, N 9.45.

2-(4'-Fluorophenyl)-1,8-naphthyridin-4-one (56) is obtained from compound (24). Characteristics: prisms; $^1$H NMR (CDCl$_3$) δ 8.66 (dd, J=7.9, 1.5Hz, 1 H, H-5), 8.62 (dd, J=4.5, 1.5 Hz, 1 H, H-7), 7.74 (dd, J=8.5, 5.0 Hz, 2H, H$_2$-2', 6'), 7.36 (dd, J=8.0, 4.5 Hz, 1 H, H-6), 7.23 (d, J=8.5 Hz, 2 H, H$_2$-3', 5'), 6.56 (s, 1 H, H-3). MS m/z 240 (M$^+$). Elemental Analysis: calculated C 68.71, H 3.91, N 11.45; found C 68.49, H 4.16, N 11.23.

2-(4'-Fluorophenyl)-5-methyl-1,8-naphthyridin-4-one (57) is obtained from compound (25). Characteristics: needles; $^1$H NMR (CDCl$_3$) δ 8.35 (d, J=4.7 Hz, 1 H, H-7), 7.71 (dd, J=8.5, 5.0 Hz, 2 H, H$_2$-2', 6'), 7.21 (t, J=8.5 Hz, 2 H, H$_2$-3', 5'), 7.04 (d, J=4.7 Hz, 1 H, H-6), 6.47 (s, 1 H, H-3), 2.93 (s, 3 H, CH$_3$-5). MS m/z 254 (M$^+$). Elemental Analysis: calculated C 70.86, H 4.36, N 11.02; found C 70.94, H 4.51, N 11.16.

2-(4'-Fluorophenyl)-6-methyl-1,8-naphthyridin-4-one (58) is obtained from compound (26). Characteristics: needles; $^1$H NMR (CDCl$_3$) δ 8.47 (d, J=2.0 Hz, 1 H, H-5), 8.45 (br. s, 1 H, H-7), 7.73 (dd, J=8.8, 5.2 Hz, 2 H, H$_2$-2', 6'), 7.22 (t, J=8.8 Hz, 2 H, H$_2$-3', 5'), 6.55 (s, 1 H, H-3), 2.46 (s, 3 H, CH$_3$-6). MS m/z 254 (M$^+$). Elemental Analysis: calculated C 70.86, H 4.36, N 11.02; found C 70.71, H 4.45, N 10.87.

2-(4'-Fluorophenyl)-7-methyl-1,8-naphthyridin-4-one (59) is obtained from compound (27). Characteristics: prisms; $^1$H NMR (CDCl$_3$) δ 9.04 (br. s, 1 H, NH-1), 8.58 (d, J=8.0 Hz, 1 H, H-5), 7.71 (dd, J=8.5, 5.0 Hz, 2 H, H$_2$-2', 6'), 7.26 (t, J=8.5 Hz, 2H, H$_2$-3', 5'), 7.23 (d, J=8.0 Hz, 1 H, H-6), 6.55 (s, 1 H, H-3), 2.64 (s, 3 H, CH$_3$-7). MS m/z 254(M$^+$). Elemental Analysis: calculated C 70.86, H 4.36, N 11.02; found C 70.59, H 4.54, N 11.11.

2-(4'-Fluorophenyl)-5,7-dimethyl-1,8-naphthyridin-4-one (60) is obtained from compound (28). Characteristics: prisms; $^1$H NMR (CDCl$_3$) δ 8.88 (br. s, 1 H, NH-1), 7.68 (dd, J=8.7, 5.1 Hz, 2 H, H$_2$-2', 6'), 7.24 (t, J=8.7 Hz, 2 H, H$_2$-3', 5'), 6.92 (s, 1 H, H-6), 6.45 (s, 1 H, H-3), 2.94 (s, 3 H, CH$_3$-5), 2.53 (s, 3 H, CH$_3$-7). MS m/z 268 (M$^+$). Elemental Analysis: 67,12, H 5.28, N 9.78; found C 67.33, H 5.45, N 9.91.

2-(4'-Fluorophenyl)-6-chloro-1,8-naphthyridin-4-one (61) is obtained from compound (29). Characteristics: prisms; $^1$H NMR (DMSO-d$_6$) δ 12.58 (br. s, 1 H, NH-1), 8.85 (d, J=2.4 Hz, 1 H, H-5), 8.44 (d, J=2.4 Hz, 1 H, H-7), 7.92 (dd, J=8.5, 5.5 Hz, 2 H, H$_2$-2', 6'), 7.40 (t, J=8.5 Hz, 2 H, H$_2$-3', 5'), 6.45 (s, 1 H, H-3). MS m/z 274 (M$^+$). Elemental Analysis: calculated C 61.22, H 2.94, N 10.20; found C 61.09, H 3.13, N 10.03.

2-(4'-Chlorophenyl)-1,8-naphthyridin-4-one (62) is obtained from compound (30). Characteristics: plates; $^1$H NMR (CDCl$_3$) δ 8.67 (dd, J=4.5, 1.5 Hz, 1 H, H-7), 8.63 (dd, J=8.0, 1.5 Hz, 1 H, H-5), 7.68 (d, J=8.7 Hz, 2 H, H$_2$-2', 6'), 7.49 (d, J=8.8 Hz, 2 H, H$_2$-3', 5'), 7.37 (dd, J=8.0, 4.5 Hz, 1 H, H-6), 6.64 (s, 1 H, H-3). MS m/z 256 (M$^+$). Elemental Analysis: calculated C 65.51, H 3.53, N 10.91; found C 65.62, H 3.73, N 10.79.

2-(4'-Chlorophenyl)-5-methyl-1,8-naphthyridin-4-one (63) is obtained from compound (31). Characteristics: amorphous; $^1$H NMR (CDCl$_3$) δ 8.36 (d, J=5.0 Hz, 1 H, H-7), 7.68 (d, J=8.5 Hz, 2 H, H$_2$-2', 6'), 7.49 (d, J=8.5 Hz, 2 H, H$_2$-3', 5'), 7.06(d, J=5.0 Hz, 1 H, H-6), 6.57 (s, 1 H, H-3), 2.95 CH$_3$-5). MS m/z 270 (M$^+$). Elemental Analysis: calculated C 66.55, H 4.10, N 10.35; found C 66.78, H 4.41, N 10.53.

2-(4'-Chlorophenyl)-6-methyl-1,8-naphthyridin-4-one (64) is obtained from compound (32). Characteristics: needles; $^1$H NMR (CDCl$_3$) δ 8.49 (s, 1 H, H-5), 8.41 (s, 1 H, H-7), 7.66 (d, J=8.5 Hz, 2 H, H$_2$-2', 6'), 7.47 (d, J=8.5 Hz, 2 H, H$_2$-3', 5'), 6.60 (s, 1 H, H-3), 2.44 (s, 3 H, CH$_3$-6). MS m/z 270 (M$^+$). Elemental Analysis: calculated C 66.55, H 4.10, N 10.35; found C 66.46, H 4.36, N 10.25.

2-(4'-Chlorophenyl)-7-methyl-1,8-naphthyridin-4-one (65) is obtained from compound (33). Characteristics: needles; $^1$H NMR (CDCl$_3$) δ 8.52 (d, J=8.0 Hz, 1 H, H-5), 7.67 (d, J=8.5 Hz, 2 H, H$_2$-2', 6'), 7.49 (d, J=8.5 Hz, 2 H, H$_2$-3', 5'), 7.22 (d, J=8.0 Hz, 1 H, H-6), 6.60 (s, 1 H, H-3), 2.64 (s, 3 H 7). MS m/z 266 (M$^+$). Elemental Analysis: calculated C 66.55, H 4.10, N 10.35; found C 66.49, H 4.31, N 10.08.

2-(4'-Chlorophenyl)-5,7-dimethyl-1,8-naphthyridin-4-one (66) is obtained from compound (34). Characteristics: prisms; $^1$H NMR (CDCl$_3$) δ 7.66 (d, J=8.5 Hz, 2 H, H$_2$-2', 6'), 7.52 (d, J=8.5 Hz, 2 H, H$_2$-3', 5'), 6.95 (s, 1 H, H-6), 6.51 (s, 1 H, H-3), 2.96 (s, 3 H, CH$_3$-5), 2.56 (s, 3 H, CH$_3$-7). MS m/z 284 (M$^+$). Elemental Analysis: calculated C 67.49, H 4.60, N 9.84; found C 67.61, H 4.69, N 9.62.

2-(4'-Methylphenyl)-5-methyl-1,8-naphthyridin-4-one (67) is obtained from compound (35). Characteristics: needles; $^1$H NMR (CDCl$_3$) δ 7.97 (d, J=4.9 Hz, 1 H, H-7), 7.61 (d, J=8.2 Hz, 2 H, H$_2$-2', 6'), 7.34 (d, J=8.2 H, 2 H, H$_2$-3', 5'), 6.95 (d, J=4.9 Hz, 1 H, H-6), 6.52 (s, 1 H, H-3), 2.98 (s, 3 H, CH$_3$-5), 2.46 (s, 3 H, CH$_3$-4'). MS m/z 250 (M$^+$). Elemental Analysis: calculated C 76.78, H 5.64, N 11.19; found C 76.56, H 5.91, N 11.02.

2-(4'-Methylphenyl)-6-methyl-1,8-naphthyridin-4-one (68) is obtained from compound (36). Characteristics: needles; $^1$H NMR (CDCl$_3$) δ 10.61 (br. s, 1 H, NH-1), 8.49 (d, J=1.5 Hz, 1 H, H-5), 8.00 (d, J=1.5 Hz, 1 H, H-7), 7.62 (d, J=8.1 Hz, 2 H, H$_2$-2', 6'), 7.36 (d, J=8.1 Hz, 2 H, H$_2$-3', 5'), 6.59 (s, 1 H, H-3), 2.47 (s, 3 H, CH$_3$-6), 2.39 (s, 3 H, CH$_3$-4'). MS m/z 250 (M$^+$). Elemental Analysis: calculated C 76.78, H 5.64, N 11.19; found C 76.73, H 5.69, N 11.03.

2-(4'-Methylphenyl)-7-methyl-1,8-naphthyridin-4-one (69) is obtained from compound (37). Characteristics: needles; $^1$H NMR (CDCl$_3$) δ 8.57 (d, J=8.0 Hz, 1 H, H-5), 7.59 (d, J=8.2 Hz, 2 H, H$_2$-2', 6'), 7.33 (d, J=8.8 H, 2 H, H$_2$-3', 5'), 7.19 (d, J=8.0 Hz, 1 H, H-6), 6.59 (s, 1 H, H-3), 2.57 (s, 3 H, CH$_3$-7), 2.44 (s, 3 H, CH$_3$-4'). MS m/z 250 (M$^+$). Elemental Analysis: calculated C 76.78, H 5.64, N 11.19; found C 76.51, H 5.53, N 11.01.

2-(4'-Methylphenyl)-5,7-dimethyl-1,8-naphthyridin-4-one (70) is obtained from compound (38). Characteristics: prisms; $^1$H NMR (CDCl$_3$) δ 7.57 (d, J=8.1 Hz, 2 H, H$_2$-2', 6'), 7.31 (d, J=8.1 Hz, 2 H, H$_2$-3', 5'), 6.89 (s, 1 H, H-6), 6.50 (s, 1 H, H-3), 2.93 (s, 3 H, CH$_3$-5), 2.48 (s, 3 H, CH$_3$-7), 2.44 (s, 3 H, CH$_3$-4'). MS m/z 264 (M$^+$). Elemental Analysis: calculated C 77.25, H 6.10, N 10.60; found C 77.43, H 6.214, N 10.52.

EXAMPLE 5

Cytotoxicity Assays of Compounds 39–70

Compounds 8–40 were assayed for in vitro cytotoxicity with a panel of human and murine tumor cell lines at the School of Medicine, University of North Carolina at Chapel Hill according to procedures described in K. H. Lee, *Planta Medica* 54:308 (1988). The cell lines include human epidermoid carcinoma of the nasopharynx (KB), lung carcinoma (A-549), ileocecal carcinoma (HCT-8), melanoma (PRMI-7951), and medulloblastoma (TE-671), as well as one murine leukemia cell line (P-388).

Compounds 41–51 and 53–68 were submitted to NCI and assayed in the NCI's in vitro disease-oriented antitumor screen, which involves determination of a test compound's effects on the growth of approximately 60 human tumor cell lines. See, M. R. Boyd, et al. In *Cancer: Principles and Practice of Oncology Updates*; De Vita, V. T., Hellman, S., Rosenberg, S. A., Eds; J. B. Lippincoft: Philadelphia, pp 1–12 (1989); and A. Monks, et al. *J. Natl. Cancer Inst.* 83:757 (1991). These lines include leukemia, non-small cell lung, colon, central nervous system (CNS), melanoma, ovarian, renal, prostate, and breast cancers. The cytotoxic effects of each compound were obtained as GI$_{50}$ or TGI values, which represent the molar drug concentrations required to cause 50% inhibition or total growth inhibition, respectively.

The results of the cytotoxicity studies of Compounds 8–40 indicated that essentially all 2-phenyl-pyrido[1,2-a]pyrimidin-4-ones were inactive (EC$_{50}$>4 μg/ml); only a few compounds showed marginal activity.

The results of the cytotoxicity studies of the 2-aryl-1,8-naphthyridin-4-ones (Compounds 41–51 and 53–68) are expressed in in Table 1 as average log GI$_{50}$ values for the entire panel of cell lines and in Table 2 as log GI$_{50}$ values for selected cell lines.

TABLE 1

| Compound | ITP[1] HC$_{50}$ (μM) ± SD | ICB[2] (% Inhibition) | average[3] log GI$_{50}$ | mp (° C.) | Yield (%)[4] |
| --- | --- | --- | --- | --- | --- |
| 39 | >40 | | −4.39 | 196–197 | 27 |
| 40 | 20 ± 1 | | −5.55 | 199–200 | 23 |
| 41 | 18 ± 1 | | −4.50 | 202–203 | 38 |
| 42 | >40 | | −4.10 | 198–199 | 48 |
| 43 | >40 | | −4.24 | 203–204 | 38 |
| 44 | 0.96 ± 0.1 | 27 ± 1 | −6.87 | 183–184 | 42 |
| 45 | 0.62 ± 0.1 | 28 ± 3 | −7.23 | 208–209 | 40 |
| 46 | 0.08 ± 0.2 | 31 ± 4 | −7.02 | 215–216 | 39 |
| 47 | 0.75 ± 0.2 | 29 ± 4 | −7.24 | 213–214 | 63 |
| 48 | 0.88 ± 0.08 | 22 ± 2 | −6.19 | 206–207 | 60 |
| 49 | 0.73 ± 0.2 | 35 ± 6 | −7.01 | 264–265 | 30 |
| 50 | 1.5 ± 0.07 | | NT[5] | 245–247 | 0.8 |
| 51 | >40 | | −4.42 | 217–218 | 33 |
| 52 | 8.8 ± 3 | | −4.89 | 196–197 | 35 |
| 53 | 7.7 ± 0.7 | | −5.21 | 261–262 | 36 |
| 54 | >40 | | −4.04 | 255–256 | 59 |
| 55 | >40 | | −4.48 | 213–214 | 56 |
| 56 | >40 | | −4.34 | 200–202 | 33 |
| 57 | 18 ± 2 | | −4.42 | 245–247 | 48 |
| 58 | 20 ± 0.2 | | −4.58 | 286–288 | 29 |
| 59 | >40 | | −4.49 | 250–251 | 77 |
| 60 | >40 | | −4.39 | 228–230 | 21 |
| 61 | 16 ± 3 | | −4.66 | >300 | 31 |
| 62 | 22 ± 0.1 | | −4.41 | >300 | 32 |
| 63 | 4.8 ± 1.4 | | −5.29 | 261–262 | 44 |
| 64 | 2.0 ± 0.01 | | −5.43 | 290–292 | 64 |
| 65 | 11 ± .07 | | −5.31 | 263–265 | 72 |

TABLE 1-continued

| Compound | ITP[1] HC$_{50}$ (μM) ± SD | ICB[2] (% Inhibition) | average[3] log GI$_{50}$ | mp (° C.) | Yield (%)[4] |
|---|---|---|---|---|---|
| 66 | 32 ± 8 | | −4.71 | 262–263 | 35 |
| 67 | 2.9 ± 0.7 | | NT[5] | 218–220 | 35 |
| 68 | 2.4 ± 0.8 | | NT[5] | 254–256 | 31 |
| 69 | 4.9 ± 0.2 | | NT[5] | 255–257 | 61 |
| 70 | 9.8 ± 2 | | NT[5] | 236–237 | 63 |
| colchicine | 0.80 ± 0.07 | | | | |
| podophyllotoxin | 0.46 ± 0.02 | 76 ± 5 | | | |
| combrtastatin A-4 | 0.53 ± 0.05 | 91 ± 2 | | | |

[1]Inhibition of Tubulin Polymerization,
[2]Inhibition of colchicine binding (evaluated only when polymerization IC50 ≦ 1 μM),
[3]Data obtained from NCI's 60 human tumor cell line in vitro screen and calculated from all cell lines tested,
[4]All yields were calculated form aminopyridines,
[5]Not tested.

TABLE 2

| | Cytotoxicity log GI$_{50}$ (M)[1] | | | | | | | | | | |
|---|---|---|---|---|---|---|---|---|---|---|---|
| Compound | HL-60(TB)[2] | NCI-H460 | HCT-1.16 | SF-295 | U-251 | SK-MEL-5 | OVCAR-3 | 786-0 | PC-3 | MDA-MB-435 | MDA-N |
| 39 | −4.41 | −4.41 | −4.56 | −4.63 | −4.17 | −4.50 | −4.32 | −4.44 | −4.53 | −4.40 | −4.70 |
| 40 | −4.68 | −4.62 | −5.12 | −4.63 | −4.45 | −4.65 | −4.89 | −4.22 | −4.68 | −5.19 | −5.08 |
| 41 | −5.02 | −4.49 | −4.37 | −4.51 | −4.56 | −4.69 | −4.71 | −4.38 | −4.57 | −5.52 | −5.35 |
| 42 | −4.13 | −4.01 | −4.42 | >−4 | >−4 | −4.29 | >−4 | >−4 | >−4 | −4.66 | −4.70 |
| 43 | −4.52 | −4.15 | −4.13 | −4.27 | >−4 | −4.47 | −4.19 | >−4 | −4.32 | −4.49 | −4.48 |
| 44 | −7.79 | −7.04 | −7.44 | −7.28 | −7.26 | −7.27 | −7.26 | 7.21 | −7.03 | <−8.00 | <−8.00 |
| 45 | −7.89 | −7.32 | −7.35 | −7.54 | −7.23 | −7.65 | −7.59 | −7.29 | −7.58 | <−8.00 | <−8.00 |
| 46 | −7.72 | −7.36 | −7.65 | −7.43 | −7.35 | −7.59 | −7.38 | −7.43 | −7.37 | <−8.00 | <−8.00 |
| 47 | −7.74 | −7.36 | −7.33 | −7.52 | −7.27 | −7.47 | −7.65 | −7.27 | −7.48 | <−8.00 | −7.96 |
| 48 | −6.76 | −6.35 | −6.39 | −6.38 | −6.77 | −6.54 | −6.60 | −6.36 | −6.51 | <−8.00 | <−8.00 |
| 49 | −7.57 | −7.20 | −6.92 | −7.22 | −6.70 | −6.90 | −6.31 | −6.37 | −6.86 | −7.49 | −7.50 |
| 51 | −4.89 | −4.58 | −4.75 | −4.19 | −4.27 | −4.46 | −4.52 | −4.25 | −4.50 | −4.70 | −4.68 |
| 52 | −5.36 | −5.21 | −5.19 | −4.71 | −5.20 | −5.41 | −4.86 | −4.60 | −4.74 | −5.62 | −5.68 |
| 53 | −5.64 | −5.39 | −5.38 | −5.28 | −5.38 | −5.43 | −5.53 | −5.29 | −5.27 | −5.74 | −5.77 |
| 54 | >−4 | >−4 | >−4 | −4.05 | >−4 | −4.32 | >−4 | >−4 | >−4 | −4.37 | −4.26 |
| 55 | −4.80 | −4.39 | −4.44 | −4.37 | −4.04 | −4.75 | −4.49 | −4.23 | −4.62 | −4.54 | −4.48 |
| 56 | −4.89 | −4.46 | −4.37 | −4.30 | −4.32 | −4.52 | −4.34 | −4.35 | −4.34 | −4.92 | −4.85 |
| 57 | −5.32 | −4.49 | −4.79 | −4.10 | −4.44 | −4.79 | −4.25 | −4.47 | −4.29 | −5.54 | −5.45 |
| 58 | −5.62 | −4.47 | −4.62 | −4.53 | −4.60 | −4.66 | −4.65 | −4.49 | −4.59 | −5.58 | −5.52 |
| 59 | −4.85 | −4.47 | −4.47 | −4.43 | −4.43 | −4.50 | −4.49 | −4.38 | −4.68 | −5.23 | −4.93 |
| 60 | −4.81 | −4.29 | −4.30 | −4.30 | −4.02 | −4.58 | −4.36 | −4.10 | −4.52 | −4.73 | −4.60 |
| 61 | −5.41 | −4.52 | −4.77 | −4.67 | −4.53 | −5.18 | −4.76 | −4.49 | −4.66 | −5.59 | −5.53 |
| 62 | −4.78 | −4.42 | −4.49 | −4.39 | −4.40 | −4.54 | −4.63 | −4.47 | −4.32 | −5.23 | −5.08 |
| 63 | −5.75 | −5.43 | −5.43 | −5.27 | −5.34 | −5.46 | −5.50 | −5.40 | −5.54 | −6.12 | −5.88 |
| 64 | −5.65 | −5.41 | −5.55 | −5.62 | −5.52 | −5.66 | −5.65 | −5.20 | −5.94 | −6.22 | −6.25 |
| 65 | −5.53 | −5.35 | −5.48 | −5.34 | −5.32 | −5.36 | −5.59 | −5.20 | −5.78 | −6.04 | −6.00 |
| 66 | −4.60 | −4.65 | −4.83 | −4.79 | −4.52 | −4.85 | −4.74 | −4.67 | −5.20 | −5.39 | −5.44 |

[1]Log concentrations which reduced cell growth to 50% of level at start of experiment.
[2]HL-60(TB); leukemia cell line; NC-H460: non-small cell lung cancer cell line; HCT-116: colon cancer cell line; SF-295 & U251: CNS cancer cell lines; SK-MEL-5: melanoma cell line; OVCAR-3: ovarian cancer cell line; 786-0: renal cancer cell line; PC-3: prostate cancer cell line; MDA-MB-435 & MDA-N: breast cancer cell lines.
[3]Not tested.

Among the compounds tested, 44–49 showed the strongest inhibitory effects against a variety of tumor cell lines, including leukemia, colon, CNS, melanoma, ovarian, renal, prostate, breast, and small cell lung cancer cell lines, with values in the low micromolar to nanomolar concentration range. It is notable that compounds 44, 46, 47, and 49 show highly selective effects on several cell lines from the leukemia, breast, and non-small lung cancer panels at the TGI level. The log TGI values for these four compounds are −7.19 to −7.40 in the HL-60 cell line, −6.16 to −7.12 in the NCI-H226 cell line, and −7.40 to −7.67 in MDA-MB-435 and MDA-N cell lines. Growth of cells from more sensitive cell lines was arrested at a concentration approximately log 2.5–3.7 concentration lower than less sensitive cell lines.

In terms of average cytotoxicity, compounds substituted at the 4'-position were substantially less active than those substituted at the 3'-position, while compounds with a methoxy group at the 2'-position were the least active. Among the tested compounds with a 4'-substituent, only minor differences in cytotoxicity were obtained, suggestive of a potency order of chloro>methoxy>fluoro. The effects of substitutions at the 5, 6, and/or 7 positions in ring A depend on the substitution in ring C. All 3'-substituted compounds with different substituents in ring A showed potent cytotoxicity, indicating that the substitution(s) can be present at different position(s) in ring A without substantially affecting cytotoxicity. For 2'- and 4'-substituted compounds, substitution at the 5 or 6 position generated slightly greater activity than no substitution or substitution at the 7 or the 5 and 7 positions in ring A. Even the "less" active compounds showed moderate cytotoxicity on two breast cancer cell lines, MDA-MB-435 and MDA-N.

EXAMPLE 6

Materials for Tubulin Bioassays of Compounds 39–70

Electrophoretically homogeneous bovine brain tubulin was purified as described in E. Hamel, et al. *Biochemistry* 23:4173 (1984). Combretastatin A-4 was a generous gift of Dr. G. R. Pettit, Arizona State University. [$^3$H]Colchicine was obtained from Dupont, nonradiolabeled colchicine from Sigma, podophyllotoxin from Aldrich, and monosodium glutamate from USB.

Tubulin Polymerization Assay

The tubulin polymerization assay was performed as described in S. Kuo, et al. *J. Med. Chem.* 36:1146 (1993); L. Li, et al. *J Med. Chem.* 37:1126 (1994); and L. Li, *J. Med. Chem.* 37:3400 (1994). In brief, tubulin at 1.2 mg/ml (12 $\mu$M) was preincubated for 15 min at 26° C. in a 0.24-ml volume of 0.8 M monosodium glutamate (pH 6.6 with NaOH in a 2 M stock solution) with varying drug concentrations. The drug stock solutions were in DMSO, and the final solvent concentration was 4% (v/v). All concentrations are in terms of the final reaction volume (0.25 ml). The reaction mixtures were chilled on ice, and 10 $\mu$l of 10 mM GTP was added to each reaction mixture. Samples were transferred to cuvettes held at 0° C. by an electronic temperature controller in Gilford spectrophotometers. Baselines were established at 350 nm, and polymerization initiated by a temperature jump to 26° C. The jump took about 50 sec to complete. After 20 min, turbidity readings were recorded, and the temperature controller was set to 0° C. When depolymerization was complete, turbidity readings were again recorded. Generally, turbidity readings were about 90% cold-reversible, and the cold-reversible turbidity was taken to represent the extent of assembly for each reaction mixture. IC$_{50}$ values were obtained graphically from inhibition of polymerization by different drug concentrations. Four spectrophotometers were used for each experimental sequence, with two control reactions (no drug) in each set. Generally, the control reactions were within 5% of their average, and IC$_{50}$ values obtained with this polymerization assay are usually highly reproducible. Generally, standard deviations were within 20% of the mean values, but in some cases, the standard deviations were 30–35% of the mean. Therefore, we can conservatively estimate that a 50% difference in IC$_{50}$ values represents a difference in the relative activity of two agents.

The results are summarized in Table 1, with a comparison to previously obtained data with the potent antimitotic natural products colchicine, podophyllotoxin, and combretastatin A-4. With the most active compounds (44–49) there was excellent correlation between cytotoxicity and inhibition of tubulin polymerization. These six strongly cytotoxic agents were the most potent inhibitors of assembly in the series. All had IC$_{50}$ values below 1.0 $\mu$M, as did the three natural products. These six agents were also examined for inhibitory effects on the binding of [$^3$H]colchicine to tubulin (1.0 $\mu$M tubulin), with inhibitor and drug at equimolar concentrations (5.0 $\mu$M). Significant and similar inhibition was observed with all six compounds, although they were substantially less potent than podophyllotoxin or combretastatin A-4 (See Table 1).

Compounds 50, 52, 53, 63, 64, and 67–70 showed reduced inhibitory effects on tubulin polymerization, with IC$_{50}$ values ranging from 1.5 to 9.8 $\mu$M. Slight inhibition was observed with compounds 40, 41, 57, 58, 61, 62, 65, and 66 (C$_{50}$ values ranging from 11 to 32 $\mu$M), while the remaining compounds (39, 42, 43, 51, 54–56, 59, and 60) were inactive, with IC$_{50}$ values greater than 40 $\mu$M. Although it is not dramatic among these less active compounds, those with greater antitubulin activity (IC$_{50}$ values<10 $\mu$M) tend to be more cytotoxic than those with little or no antitubulin activity.

From the tubulin data, the 3'-substitution of a methoxy group was well-tolerated, while the 4'926 - and 2'-methoxy substituents resulted in large, progressive losses of activity or total loss of activity. On the other hand, the series of 4'-substituents indicate that the methyl and chloride groups are better tolerated than the methoxy group and that the fluoride group is equivalent to the methoxy substituent at position 4'. This suggests that a strong electron-withdrawing or a large electron-donating group at the 4'-position may be unfavorable for the drug-tubulin interaction.

The tubulin assay also yielded data of interest regarding A ring substituents. No clear pattern was observed in the potent 3'-methoxy-substituted subseries (compounds 44–50), for a variety of substituents at different position(s) of ring A were well-tolerated. These substituents include both an electron-donating group (CH$_3$) and electron-withdrawing groups (Cl and Br). The size of the substituents (as small as hydrogen, compound 44, and as large as two methyl groups, compound 48) and their positions (no substitution or different positions of both mono- and disubstitution) did not greatly affect relative compound activities.

However, a consistent pattern for A ring substitution emerged in the other five subseries (2'-methoxy, 4'-methoxy, 4'-fluoride, 4'-chloride, 4'-methyl). In all cases C-5 and C-6 substituents (generally methyl groups) enhanced activity relative to the unsubstituted derivative and to those bearing a C-7 substituent or two substituent groups.

EXAMPLE 7

Colchicine Binding Assay of Compounds 39–70

The binding of radiolabeled colchicine to tubulin was measured by the DEAE-cellulose filter technique, as described in S. Kuo, et al. *J. Med. Chem.* 36:1146 (1993). In brief each 0.1-ml reaction mixture contained 0.1 mg (1.0 $\mu$M) of tubulin, 1.0 M commercial monosodium glutamate (pH 6.6 with HCl), 1 mM MgCl$_2$, 0.1 mM GTP, 5.0 $\mu$M [$^3$H]colchicine, 5% (v/v) DMSO, and 5.0 $\mu$M inhibitor. Incubation was for 20 min at 37° C. Each reaction mixture was filtered under reduced vacuum through a stack of two DEAE-cellulose paper filters, washed with water, and radioactivity quantitated in a liquid scintillation counter.

The most active 2-phenyl-1,8-naphthyridin-4-ones approach colchicine in their potency as inhibitors of tubulin polymerization. While these compounds appear to interact at the colchicine binding site of tubulin, they only weakly inhibit the binding of radiolabeled colchicine to tubulin. This apparent discrepancy probably arises from a relatively slow binding and/or rapid dissociation reaction of these agents with tubulin relative to the binding and dissociation reactions of colchicine with the protein. These properties are similar to those of a structurally related class of antimitotic agents, the 2-phenyl-4-quinolones, which were developed in our laboratory. The 2-phenyl-1,8-naphthyridin-4-ones and 2-phenyl-4-quinolones together with other natural products, such as podophyllotoxin and combretastatin, fall into a group of colchicine site compounds that have two aryl ring systems connected by a hydrocarbon bridge of variable length. In both classes of compounds, derivatives with a methoxy at the 3'-position were the most active compounds within their series and were much more active than isomers with the same substituent at the 2'-or 4'-position. However, unlike the 2-phenyl-4-quinolones, in which a 4'-methoxy group reduced activity more than a 2'-methoxy substituent, in the 2-phenyl-1,8-naphthyridin-4-ones, a 2'-methoxy group reduced activity more than did a 4'-substituent. Moreover, in the 2-phenyl-4-quinolone series, A ring substituents were optimal at positions 6 and 7, whereas in the 2-phenyl-1,8-naphthyridin-4-one series, it appears that A ring substituents are optimal at s 5 and 6.

The COMPARE® computer program uses the patterns of cellular responsiveness in the NCI 60 cell line screen to calculate Pearson correlation coefficients between data for seed compounds and those for past agents in the database. The significance of these computations is that the observed correlation coefficients are greatest in pairs of compounds sharing common intracellular targets. COMPARE® computations for the six most potent compounds (44–49) against several known tubulin/microtubule binding agents are shown in Table 3at both the $GI_{50}$ and TGI levels.

TABLE 3

| Compd | Colchicine | | Maytansine | | Vincristine | | Vinblastine | | Rhizoxin | | Paclitaxel | |
|---|---|---|---|---|---|---|---|---|---|---|---|---|
| | $GI_{50}$ | TGI | $GI_{50}$ | TGI | $GI_{50}$ | TGI | $GI_{50}$ | TGI | $GI_{50}$ | TGI | $GI_{50}$ | TGI |
| 44 | 0.66 | 0.55 | 0.65 | 0.64 | 0.58 | 0.45 | 0.47 | 0.67 | 0.60 | 0.60 | 0.36 | 0.63 |
| 45 | 0.69 | 0.47 | 0.73 | 0.37 | 0.61 | 0.41 | 0.60 | 0.53 | 0.58 | 0.40 | 0.30 | 0.47 |
| 46 | 0.73 | 0.53 | 0.69 | 0.62 | 0.58 | 0.44 | 0.56 | 0.62 | 0.54 | 0.58 | 0.40 | 0.53 |
| 47 | 0.79 | 0.47 | 0.74 | 0.45 | 0.71 | 0.43 | 0.64 | 0.56 | 0.61 | 0.45 | 0.41 | 0.55 |
| 48 | 0.71 | 0.55 | 0.71 | 0.51 | 0.62 | 0.48 | 0.65 | 0.64 | 0.65 | 0.51 | 0.46 | 0.61 |
| 49 | 0.70 | 0.58 | 0.63 | 0.69 | 0.62 | 0.55 | 0.51 | 0.77 | 0.55 | 0.62 | 0.31 | 0.65 |

Correlation coefficients >0.6 at either level can be considered significant. These compounds display higher correlations with colchicine and maytansine than with the vinca alkaloids or rhizoxin, while correlations with paclitaxel (Taxol) are comparatively weak.

EXAMPLE 8

Data Regarding Specific 2-Aryl-pyrido[1,2, a] pyrimidin-4-ones (Compounds 5'–28')

2-(3'-Fluorophenyl)-7-methyl-pyrido[1,2-a]pyrimidin-4-one (5') is obtained from ethyl 3'-fluorobenzoylacetate and 2-amino-5-picoline.
Characteristics: amorphous; mp 163–165° C.; $^1$H NMR (CDCl$_3$) δ 8.90 (s, 1 H, H-6), 7.85 (d, J=8.5 Hz, 1 H, H-6'), 7.83 (s, 1 H, H-2'), 7.71 (d, J=9.0 Hz, 1 H, H-9), 7.65 (dd, J=9.0, 1.5 Hz, 1 H, H-8), 7.48 (m, 1 H, H-5'), 7.19 (dt, J=2.0, 8.5 Hz, 1 H, H-4'), 6.88 (s, 1 H, H-3), 2.46 (s, 3 H, CH$_3$-7). MS m/z 254 (M$^+$).
2-(3'-Fluorophenyl)-6-methyl-pyrido[1,2-a]pyrimidin-4-one (6') is obtained from ethyl 3'-fluorobenzoylacetate and 2-amino-6-picoline.
Characteristics: amorphous; mp 145–146° C.; $^1$H NMR (CDCl$_3$) δ 7.82 (d, J=7.5, Hz, 1 H, H-6'), 7.80 (d, J=1.5, Hz, 1 H, H-2'), 7.51 (d, J=7.5 Hz, 1 H, H-9), 7.48 (m, 1 H, H-5'), 7.45 (dd, J=7.5, 6.0 Hz, 1 H, H-8), 7.18 (dt, J=2.5, 8.0 Hz, 1 H, H-4'), 6.72 (s, 1 H, H-3), 6.69 (d, J=6.0 Hz, 1 H, H-7), 3.10 (s, 3 H, CH$_3$-6) m/z 254 (M$^+$).
2-(3'-Fluorophenyl)-6,8-dimethyl-pyrido[1,2-a]pyrimidin-4-one (7') is obtained from ethyl 3'-fluorobenzoylacetate and 2-amino-4,6-dimethylpyridine. Characteristics: amorphous; mp 162–164° C.; $^1$H NMR (CDCl$_3$) δ 7.80 (d, J=8.0 Hz, 1 H, H-6'), 7.79 (d, J=1.0 Hz, 1 H, H-2'), 7.45 (m, 1 H, H-5'), 7.30 (br. s, 1 H, H-9), 7.17 (dt, J=2.5, 8.0 Hz, 1 H, H-4'), 6.64 (s, 1 H, H-3), 6.53 (br. s, 1 H, H-7), 3.07 (s, 3 H, CH$_3$-6), 2.37 (s, 3 H, CH$_3$-8). MS n/z 268 (M$^+$).
2-(3'-Chlorophenyl)-pyrido[1,2-a]pyrimidin-4-one (8') is obtained from ethyl 3'-chlorobenzoylacetate and 2-aminopyridine. Characteristics: amorphous; mp 160–161° C.; $^1$H NMR (CDCl$_3$) δ 9.08 (d, J=7.2 Hz, 1 H, H-6), 8.15 (t, J=1.5 Hz, 1 H, H-2'), 7.94 (td, J=7.0, 1.5 Hz, 1 H, H-6'), 7.79 (m, 2 H, H$_2$-8, 9), 7.46 (m, 2 H, H$_2$-4', 5'), 7.17 (dt, J=6.5, 1.5 Hz, 1 H, H-7), 6.90 (s, 1 H, H-3). MS m/z 256 (M$^+$).
2-(3'-Chlorophenyl)-8-methyl-pyrido[1,2-a]pyrimidin-4-one (9') isobtained from ethyl 3'-chlorobenzoylacetate and 2-amino-4-picoline; prisms, mp 142–144° C.; $^1$H NMR (CDCl$_3$) δ 8.97 (d, J=7.2 Hz, 1 H, H-6), 8.13 (t, J=2.0, 1 H, H-2'), 7.92 (td, J=7.5, 2.0 Hz, 1 H, H-6'), 7.54 (br. s, 1 H, H-9), 7.45 (m, 2 H, H$_2$-4', 5'), 7.00 (dd, J=7.2, 2.0 Hz, 1 H, H-7), 2.52 (s, 3 H, CH$_3$-8). MS m/z 270 (M$^+$).
2-(3'-Chlorophenyl)-7-methyl-pyrido[1,2-a]pyrimidin-4-one (10') is obtained from ethyl 3'-chlorobenzoylacetate and 2-amino-5-picoline.
Characteristics: prisms; mp 175–176° C.; $^1$H NMR (CDCl$_3$) δ 8.89 (s, 1 H, H-6), 8.13 (s, 1 H, H-2'), 7.92 (td, J=7.0, 1.0 Hz, 1 H, H-6'), 7.69 (d, J=9.0 Hz, 1 H, H-9), 7.64 (dd, J=9.0, 1.5 Hz, 1 H, H-8), 7.45 (m, 2 H, H$_2$-4', 5') 6.86 (s, 1 H, H-3), 2.46 (s, 3 H, CH$_3$-7). MS m/z 270 (M$^+$).
2-(3'-Chlorophenyl)-6-methyl-pyrido[1,2-a]pyrimidin-4-one (11') is obtained from ethyl 3'-chlorobenzoylacetate and 2-amino-6-picoline.
Characteristics: needles; mp 150–152° C.; $^1$H NMR (CDCl$_3$) δ 8.10 (t, J=1.5 Hz, 1 H, H-2'), 7.91 (td, J=8.0, 1.5 Hz, 1 H, H-6'), 7.52 (d, J=7.0 Hz, 1 H, H-9), 7.48 (dd, J=8.0, 7.0 Hz, 1 H, H-8), 7.45 (m, 2 H, H$_2$-4', 5'), 6.70 (s, 1 H, H-3), 6.68 (d, J=8.0 Hz, 1 H, H-7), 3.10 (s, 3 H, CH$_3$-6). MS m/z 270 (M$^+$).
2-(3'-Chlorophenyl)-6,8-dimethyl-pyrido[1,2-a]pyrimidin-4-one (12') is obtained from ethyl 3'-chlorobenzoylacetate and 2-amino-4,6-dimethylpyridine. Characteristics: prisms; mp 125–126° C.; $^1$H NMR (CDCl$_3$) δ 8.09 (t, J=2.0 Hz, 1 H, H-2'), 7.89 (dd, J=6.7, 2.0 Hz, 1 H, H-6'), 7.43(m, 2 H, H$_2$-4', 5'), 7.31 (br. s, 1 H, H-9), 6.63 (s, 1 H, H-3), 6.53 (br. s, 1 H, H-7), 3.07 (s, 3 H, CH$_3$-6), 2.37 (s, 3H, CH$_{3-8}$). MS m/z 284 (M$^+$).
2-(3'-Methylphenyl)-pyrido[1,2-a]pyrimidin-4-one (13') is obtained from ethyl 3'-methylbenzoylacetate and 2-aminopyridine.
Characteristics: needles; mp 118–120° C.; $^1$H NMR (CDCl$_3$) δ 9.09 (d, J=7.0 Hz, 1 H, H-6), 7.94 (s, 1 H, H-2'), 7.87 (d, J=7.5, Hz, 1 H, H-6'), 7.76 (d, J=3.5 Hz, 2 H, H$_2$-8, 9), 7.41 (t, J=7.5 Hz, 1 H, H-5'), 7.32 (d, J=7.5 Hz, 1 H, H-4'), 7.15 (ddd, J=7.0, 3.5, 1.5 Hz, 1 H, H-7), 6.92 (s, 1 H, H-3), 2.47 (s, 3 H, CH$_3$-3'). MS m/z 236 (M$^+$).
2-(3'-Methylphenyl)-8-methyl-pyrido[1,2-a]pyrimidin-4-one (14') is obtained from ethyl 3'-methylbenzoylacetate and 2-arnino-4-picoline.

Characteristics: amorphous; mp 146–148° C.; $^1$H NMR (CDCl$_3$) δ 8.97 (d, J=7.2 Hz, 1 H, H-6), 7.92 (s, 1 H, H-2'), 7.86 (d, J=7.5, 1 H, H-6'), 7.54 (s, 1 H, H-9), 7.40 (t, J=7.5 Hz, 1 H, H-5'), 7.31 (d, J=7.5, Hz, 1 H, H-4'), 6.98 (d, J=7.2 Hz, 1 H, H-7), 6.85 (s, 1 H, H-3), 2.51 (s, 3H, CH$_3$-8), 2.45 (s, 3 H, CH$_3$-3'). 250 (M$^+$).

2-(3'-Methylphenyl)-7-methyl-pyrido[1,2-a]pyrimidin-4-one (15') is obtained from ethyl 3'-methylbenzoylacetate and 2-amino-5-picoline.

Characteristics: prisms; mp 158–160° C.; $^1$H NMR (CDCl$_3$) δ 8.90 (s, 1 H, H-6), 7.92 (s, 1 H, H-2'), 7.86 (d, J=7.7, 1 H, H-6'), 7.69 (d, J=9.0 Hz, 1 H, H-9), 7.62 (dd, J=9.0, 2.0 Hz, 1 H, H-8), 7.40 (t, J=7.7, Hz, 1 H, H-5'), 7.31 (d, J=7.7, Hz, 1 H, H-4'), 6.90 (s, 1 H, H-3), 2.47 (s, 3 H, CH$_3$-7), 2.46 (s, 3 H, CH$_3$-3') m/z 250 (M$^+$).

2-(3'-Methylphenyl)-6-methyl-pyrido[1,2-a]pyrimidin-4-one (16') is obtained from ethyl 3'-methylbenzoylacetate and 2-amino-6-picoline.

Characteristics: prisms; mp 152–154° C.; $^1$H NMR (CDCl$_3$) δ 7.90 (s, 1 H, H-2'), 7.84 (d, J=7.7, 1 H, H-6'), 7.51 (d, J=8.5, Hz, 1 H, H-9), 7.46 (dd, J=8.5, 6.4Hz, 1 H, H-8), 7.39 (t, J=7.5 Hz, 1 H, H-5'), 7.30 (d, J=7.7, Hz, 1 H, H-4'), 6.73 (s, 1 H, H-3), 6.66 (d, J=6.4 Hz, 1 H, H-7), 3.09 (s, 3 H, CH$_3$-6), 2.46 (s, 3 H, CH$_3$-3'). MS m/z 250 (M$^+$).

2-(3'-Methylphenyl)-6,8-dimethyl-pyrido[1,2-a]pyrimidin-4-one (17') is obtained from ethyl 3'-methylbenzoylacetate and 2-amino-4,6-dimethylpyridine. Characteristics: prisms; mp 145–147° C.; $^1$H NMR (CDCl$_3$) δ 7.88 (br. s, 1 H, H-2'), 7.82 (d, J=7.5, Hz, 1 H, H-6'), 7.38 (t, J=7.5 Hz, 1 H, H-5'), 7.35 (br. s, 1 H, H-9), 7.28 (d, J=7.5, Hz, 1 H, H-4'), 6.66 (s, 1 H, H-3), 6.50 (br. s, 1 H, H-7), 3.07 (s, 3 H, CH$_3$-6), 2.45 (s, 3 H, CH$_3$-3'), 2.36 (s, 3 H, CH$_3$-8). MS m/z 264 (M$^+$).

2-(α-Naphthyl)-pyrido[1,2-a]pyrimidin-4-one (18') is obtained from ethyl α-naphthylbenzoylacetate and 2-aminopyridine. Characteristics: amorphous; mp 169–170° C.; $^1$H NMR (CDCl$_3$) δ 9.19 (d, J=7.0 Hz, 1 H, H-6), 8.24 (dd, J=6.5, 2.5 Hz, 1 H, H-8'), 7.97 (d, J=8.5 Hz, 1 H, H-2'), 7.95 (m, 1 H, H-5'), 7.81 (d, J=2.5 Hz, 2 H, H$_2$-8, 9), 7.72 (d, J=6.5 Hz, 1 H, H-4'), 7.58 (dd, J=8.5, 6.5 Hz, 1 H, H-3'), 7.52 (m, 2 H, H$_2$-6', 7'), 7.24 (m, 1 H, H-7), 6.80 (s, 1 H, H-3). MS m/z 272 (M$^+$).

2-(α-Naphthyl)-8-methyl-pyrido[1,2-a]pyrimidin-4-one (19') is obtained from ethyl α-naphthylbenzoylacetate and 2-amino-4-picoline.

Characteristics: needles; mp 146–148° C.; $^1$H NMR (CDCl$_3$) δ 9.08 (d, J=7.2 Hz, 1 H, H-6), 8.24 (dd, J=6.5, 2.5 Hz, 1 H, H-8'), 7.96 (d, J=8.7 Hz, 1 H, H-2'), 7.93 (m, 1 H, H-5'), 7.71 (d, J=6.8 Hz, 1 H, H-4'), 7.62 (br. s, 1 H, H-9), 7.58 (dd, J=8.7, 6.8 Hz, 1 H, H-3'), 7.53 (m, 2 H, H$_2$-6', 7'), 7.08 (dd, J=7.2, 1.5 Hz, 1 H, H-7), 6.72 (s, 1 H, H-3), 2.54 (s, 3 H, CH$_3$-8). MS m/z 286 (M$^+$).

2-(α-Naphthyl)-7-methyl-pyrido[1,2-a]pyrimidin-4-one (20') is obtained from ethyl α-naphthylbenzoylacetate and 2-amino-5-picoline.

Characteristics: amorphous; mp 138–140° C.; $^1$H NMR (CDCl$_3$) δ 8.99 (s, 1 H, H-6), 8.24 (dd, J=6.5, 2.5 Hz, 1 H, H-8'), 7.96 (d, J=8.7 Hz, 1 H, H-2'), 7.93 (m, 1 H, H-5'), 7.72 (d, J=7.0 Hz, 1 H, H-4'), 7.70 (d, J=9.0 Hz, 1 H, H-9), 7.66 (dd, J=9.0, 1.5 Hz, 1 H, H-8), 7.56 (dd, J=8.7, 6.8 Hz, 1 H, H-3'), 7.50 (m, 2 H, H$_2$-6', 7'), 6.77 (s, 1 H, H-3), 2.49 (s, 3 H, CH$_3$-7). MS m/z 286 (M$^+$).

2-(α-Naphthyl)-6-methyl-pyrido[1,2-a]pyrimidin4-one (21') is obtained from ethyl α-naphthylbenzoylacetate and 2-amino-6-picoline.

Characteristics: prisms; mp 149–150° C.; $^1$H NMR (CDCl$_3$) δ 8.28 (dd, J=5.0, 2.5Hz, 1 H, H-8'), 7.95 (d, J=8.3 Hz, 1 H, H-2'), 7.92 (m, 1 H, H-5'), 7.71 (d, J=6.5 Hz, 1 H, H-4'), 7.56 (dd, J=8.7, 6.8 Hz, 1 H, H-3'), 7.52 (m, 2 H, H$_2$-8, 9), 7.50 (m, 2 H, H$_2$-6', 7'), 6.74 (d, J=5.5 Hz, 1 H, H-7), 6.61 (s, 1 H, H-3), 3.16 (CH$_3$-6). MS m/z 286 (M$^+$).

2-(α-Naphthyl)-6,8-dimethyl-pyrido[1,2-a]pyrimidin-4-one (22') is obtained from ethyl α-naphthylbenzoylacetate and 2-amino-4,6-dimethylpyridine.

Characteristics: prisms; mp 160–162° C.; $^1$H NMR (CDCl$_3$) δ 8.27 (dd, J=5.0, 2.5Hz, 1 H, H-8'), 7.94 (d, J=7.5 Hz, 1 H, H-2'), 7.92 (m, 1 H, H-5'), 7.70 (d, J=7.5 Hz, 1 H, H-4'), 7.54 (t, J=7.5 Hz, 1 H, H-3'), 7.51 (m, 2 H, H$_2$-6', 7'), 7.35 (br. s, 1 H, H-9), 6.60 (br. s, 1 H, H-7), 6.53 (s, 1 H, H-3), 3.13 (s, 3 H, CH$_3$-6), 2.39 (s, 3 H, CH$_3$-8). MS m/z 300 (M$^+$).

2-(α-Naphthyl)-pyrido[1,2-a]pyrimidin-4-one (23') is obtained from ethyl β-naphthylbenzoylacetate and 2-aminopyridine. Characteristics: amorphous; mp 201–202° C.; $^1$H NMR (CDCl$_3$) δ 9.11 (d, J=7.0 Hz, 1 H, H-6), 8.68 (s, 1 H, H-1'), 8.18 (dd, J=8.5, 1.0 Hz, 1 H, H-3'), 7.99 (m, 1 H, H-8'), 7.98 (d, J=8.5 Hz, 1 H, H-4'), 7.91 (m, 1 H, H-5'), 7.81 (m, 2 H, H$_2$-8, 9), 7.57 (m, 2 H, H$_2$-6', 7'), 7.17 (dt, J=7.0, 2.0 Hz, 1 H, H-7), 7.08 (s, 1 H, H-3). MS m/z 272 (M$^+$).

2-(β-Naphthyl)-8-methyl-pyrido[1,2-a]pyrinidin-4-one (24') is obtained from ethyl β-naphthylbenzoylacetate and 2-amino-4-picoline.

Characteristics: amorphous; mp 168–169° C.; $^1$H NMR (CDCl$_3$) δ 9.00 (d, J=7.2 Hz, 1 H, H-6), 8.66 (s, 1 H, H-1'), 8.16 (d, J=8.5 Hz, 1 H, H-3'), 7.99 (s, 1 H, H-9), 7.98 (m, 1 H, H-8'), 7.97 (d, J=8.5 Hz, 1 H, H-4'), 7.90 (br. d, J=7.0 Hz, 1 H, H-5'), 7.57 (m, 2 H, H$_2$-6', 7'), 7.01 (s, 1 H, H-3), 6.99 (d, J=7.2 Hz, 1 H, H-7), 2.54 (s, 3 H, CH$_3$-8). MS m/z 286 (M$^+$).

2-(β-Naphthyl)-7-methyl-pyrido[1,2-a]pyrimidin-4-one (25') is obtained from ethyl β-naphthylbenzoylacetate and 2-amino-5-picoline.

Characteristics: needles; mp 228–229° C.; $^1$H NMR (CDCl$_3$) δ 8.93 (s, 1 H, H-6), 8.66 (s, 1 H, H-1'), 8.17 (dd, J=8.7, 1.0 Hz, 1 H, H-3'), 7.99 (m, 1 H, H-8'), 7.97 (d, J=8.7 Hz, 1 H, H-4'), 7.90 (m, 1 H, H-5'), 7.75 (d, J=9.0 Hz, 1 H, H-9), 7.65 (dd, J=9.0, 1.2 Hz, 1 H, H-8), 7.56 (m, 2 H, H$_2$-6', 7'), 7.06 (s, 1 H, H-3), 2.47 (s, 3 H, CH$_3$-7). MS m/z 286 (M$^+$).

2-(β-Naphthyl)-6-methyl-pyrido[1,2-a]pyrimidin-4-one (26') is obtained from ethyl β-naphthylbenzoylacetate and 2-amino-6-picoline.

Characteristics: prisms; mp 160–162° C.; $^1$H NMR (CDCl$_3$) δ 8.64 (s, 1 H, H-1'), 8.14 (d, J=8.6 Hz, 1 H, H-3'), 7.99 (m, 1 H, H-8'), 7.96 (d, J=8.6 Hz, 1 H, H-4'), 7.90 (m, 1 H, H-5'), 7.55 (m, 2 H, H$_2$-6', 7'), 7.53 (d, J=8.8 Hz, 1 H, H-9), 7.49 (dd, J=8.8, 6.5 Hz, 1 H, H-8), 6.88 (s, 1 H, H-3), 6.68 (d, J=6.5 Hz, 1 H, H-7), 3.12 (s, 3H, CH$_3$-6). MS m/z 286 (M$^+$).

2-(β-Naphthyl)-6,8-dimethyl-pyrido[1,2-a]pyrimidin-4-one (27') is obtained from ethyl β-naphthylbenzoylacetate and 2-amino-4,6-dimethylpyridine.

Characteristics: needles; mp 189–190° C.; $^1$H NMR (CDCl$_3$) δ 8.62 (s, 1 H, H-1'), 8.12 (d, J=8.9 Hz, 1 H, H-3'), 7.98 (m, 1 H, H-8'), 7.94 (d, J=8.9 Hz, 1 H, H-4'), 7.89 (m, 1 H, H-5'), 7.55 (m, 2 H, H$_2$-6', 7'), 7.36 (br. s, 1 H, H-9), 6.81 (s, 1 H, H-3), 6.53 (br. s, 1 H, H-7), 3.09 (s, 3 H, CH$_3$-6), 2.38 (s, 3 H, CH$_3$-8). MS m/z 300 (M$^+$).

2-(β-Naphthyl)-7-chloro-pyrido[1,2-a]pyrimidin-4-one (28') is obtained from ethyl β-naphthylbenzoylacetate and 2-amnino-5-chloro-pyridine.

Characteristics: amorphous; mp 227–229° C.; $^1$H NMR (CDCl$_3$) δ 9.12 (d, J=2.0 Hz, 1 H, H-6), 8.66(s, 1 H, H-1'), 8.15 (dd, J=8.7, 1.5 Hz, 1 H, H-3'), 8.00 (m, 1 H, H-8'), 7.97 (d, J=8.7 Hz, 1 H, H-4'), 7.90 (m, 1 H, H-5'), 7.75 (d, J=9.3 Hz, 1 H, H-9), 7.70 (dd, J=9.3, 2.0 Hz, 1 H, H-8), 7.57 (m, 2 H, H2-6', 7'), 7.09 (s, 1 H, H-3). MS m/z 306 (M$^+$).

EXAMPLE 9

Data Regarding Specific 2-phenyl-1,8-naphthyridin-4-ones (Compounds 29'–51')

2-(3'-Fluorophenyl)-6-methyl-1,8-naphthyridin-4-one (29') is obtained from compound (5'). Characterisitics: needles; $^1$H NMR (CDCl$_3$+CD$_3$OD) δ 8.48 (d, J=2.0 Hz, 1 H, H-5), 8.47 (d, J=2.0 Hz, 1 H, H-7), 7.52 (m, 2 H, H$_2$-2', 5'), 7.45 (dd, J=8.0, 2.0 Hz, 1 H, H-6'), 7.25 (m, 1 H, H-4'), 6.57 (s, 1 H, H-3), 2.47 (s, 3 H, CH$_3$-6). MS m/z 254 (M$^+$). Elemental Analysis: calculated C 70.86, H 4.36, N 11.02; found C 70.69, H 4.48, N 10.91.

2-(3'-Fluorophenyl)-7-methyl-1,8-naphthyridin-4-one (30') is obtained from compound (6'). Characteristics: amorphous; $^1$H NMR (CDCl$_3$) δ 8.90, (br. s, 1 H, NH-1), 8.56 (d, J=8.0 Hz, 1 H, H-5), 7.52 (m, 2 H, H$_2$-2', 5'), 7.41 (d, J=9.5 Hz, 1 H, H-6'), 7.29 (m, 1 H, H-4'), 7.23 (d, J=8.0 Hz, 1 H, H-6) 6.57 (s, 1 H, H-3), 2.64(s, 3 H, CH$_3$-7). MS m/z 254 (M$^+$). Elemental Analysis: calculated C 70.86, H 4.36, N 11.02; found C 70.99, H 4.62, N 10.97.

2-(3'-Fluorophenyl)-5,7-dimethyl-1,8-naphthyridin-4-one (31') is obtained from compound (7'). Characteristics: amorphous; $^1$H NMR (CDCl$_3$) δ 8.86, (br. s, 1 H, NH-1), 7.50 (m, 2 H, H$_2$-2', 5'), 7.39 (dd, J=9.3, 1.8 Hz, 1 H, 6'), 7.24 (m, 1 H, H-4'), 6.92 (s, 1 H, H-6), 6.49 (s, 1 H, H-3), 2.93 (s, 3 H, CH$_3$-5), 2.51 (s, 3 H, CH$_3$-7). MS m/z 268 (M$^+$). Elemental Analysis: calculated C 71.63, H 4.88, N 10.44; found C 71.82, H 5.01, N 10.21.

2-(3'-Chlorophenyl)-1,8-naphthyridin-4-one (32') is obtained from compound (8'). Characteristics: needles; $^1$H NMR (CDCl$_3$) δ 8.66 (dd, J=4.5, 2.0 Hz, 1 H, H-5), 8.63 (dd, J=8.0, 2.0 Hz, 1 H, H-7), 7.72 (t, J=1.5 Hz, 1 H, H-2'), 7.61 (td, J=7.0, 1.5 Hz, 1 H, H-6'), 7.48 (m, 2 H, H$_2$-4', 5'), 7.36 (dd, J=8.0, 4.5 Hz, 1 H, H-6), 6.58 (s, 1 H, H-3). MS m/z 256 (M$^+$). Elemental Analysis: calculated C 65.51, H 3.53, N 10.91; found C 65.28, H 3.65, N 10.67.

2-(3'-Chlorophenyl)-5-methyl-1,8-naphthyridin-4-one (33') is obtained from compound (9'). Characteristics: needles; $^1$H NMR (CDCl$_3$+CD$_3$OD) δ 8.37 (d, J=5.0 Hz, 1 H, H-7), 7.70 (t, J=2.0 Hz, 1 H, H-2'), 7.59 (td, J=7.2, 2.0 Hz, 1 H, H-6'), 7.46 (m, 2 H, H$_2$-4', 5'), 7.02 (d, J=5.0 Hz, 1 H, H-6), 6.49 (s, 1 H, H-3), 2.91 (s, 3 H, CH$_3$-5). MS m/z 270 (M$^+$). Elemental Analysis: calculated C 66.55, H 4.10, N 10.35; found C 66.82, H 4.45, N 10.43.

2-(3'-Chlorophenyl)-6-methyl-1,8-naphthyridin-4-one (34') is obtained from compound (10'). Characteristics: amorphous; $^1$H NMR (CDCl$_3$+CD$_3$OD) δ 8.49 (d, J=2.0 Hz, 1 H, H-5), 8.42 (d, J=2.0 Hz, 1 H, H-7), 7.72 (t, J=1.5 Hz, 1 H, H-2'), 7.61(td, J=7.2, 1.5 Hz, 1 H, H-6'), 7.48 (m, 2 H, H$_2$-4', 5'), 6.57 (s, 1 H, H-3), 2.46 (s, 3 H, CH$_3$-6). MS m/z 270 (M$^+$). Elemental Analysis: calculated C 66.55, H 4.10, N 10.35; found C 66.26, H 4.41, N 10.22.

2-(3'-Chlorophenyl)-7-methyl-1,8-naphthyridin-4-one (35') is obtained from compound (11'). Characteristics: amorphous; $^1$H NMR (CDCl$_3$+CD$_3$OD) δ 8.54 (d, J=8.0 Hz, 1 H, H-5), 7.72 (t, J=2.0 Hz, 1 H, H-2'), 7.61 (td, =6.8, 2.0 Hz, 1 H, H-6'), 7.50 (m, 2 H, H$_2$-4', 5'), 7.23 (d, J=8.0 Hz, 1 H, H-6), 2.64 (s, 3 H, CH$_3$-7). MS m/z 270 (M$^+$). Elemental Analysis: calculated C 66.55, H 4.10, N 10.35; found C 66.38, H 4.37, N 10.11.

2-(3'-Chlorophenyl)-5,7-dimethyl-1,8-naphthyridin-4-one (36') is obtained from compound (12'). Characteristics: needles; $^1$H NMR (CDCl$_3$) δ 7.67 (t, J=1.5 Hz, 1 H, H-2'), 7.58 (td, J=7.0, 1.5 Hz, 1 H, H-6'), 7.50 (m, 2 H, H$_2$-4', 5'), 6.93 (s, 1 H, H-6), 6.49 (s, 1 H, H-3), 2.94 (s, 3 H, CH$_3$-5), 2.53 (s, 3 H, CH$_3$-7). MS m/z 284 (M$^+$). Elemental Analysis: calculated C 67.49, H 4.60, N 9.84; found C 67.31, H 4.72, N 9.66.

2-(3'-Methylphenyl)-1,8-naphthyridin-4-one (37') is obtained from compound (13'). Characteristics: prisms; $^1$H NMR (CDCl$_3$) δ 10.57, (br. s, 1 H, NH-1), 8.70 (dd, J=8.0, 2.0 Hz, 1 H, H-5), 8.18 (dd, J=4.5, 2.0 Hz, 1 H, H-7), 7.54 (d, J=1.5 Hz, 1 H, H-2'), 7.53 (d, J=7.5 Hz, 1 H, H-6'), 7.45 (t, J=7.5, Hz, 1 H, H-5'), 7.40 (d, J=7.5 Hz, 1 H, H-4'), 7.27 (dd, J=8.0, 4.5 Hz, 1 H, H-6), 6.60 (s, 1 H, H-3), 2.44 (s, 3 H, CH$_3$-3'). MS m/z 236 (M$^+$). Elemental Analysis: calculated C 76.25, H 5.12, N 11.86; found C 76.35, H 5.41, N 11.93.

2-(3'-Methylphenyl)-5-methyl-1,8-naphthyridin-4-one (38') is obtained from compound (14'). Characteristics: needles; $^1$H NMR (CDCl$_3$) δ 9.77, (br. s, 1 H, NH-1), 8.10 (d, J=4.8 Hz, 1 H, H-7), 7.52 (s, 1 H, H-2'), 7.50 (br. d, J=6.0 Hz, 1 H, H-6'), 7.43 (t, J=7.5 Hz, 1 H, H-5'), 7.37(d, J=7.5 Hz, 1 H, H-4'), 6.98 (d, J=4.8 Hz, 1 H, H-6), 6.52 (s, 1 H, H-3), 2.98 (s, 3 H, CH$_3$-5), 2.45 (s, 3 H, CH$_3$-3'). MS m/z 250 (M$^+$). Elemental Analysis: calculated C 76.78, H 5.64, N 11.19; found C 76.52, H 5.75, N 11.01.

2-(3'-Methylphenyl)-6-methyl-1,8-naphthyridin-4-one (39') is obtained from compound (15'). Characteristics: prisms; $^1$H NMR (CDCl$_3$) δ 10.78, (s, 1 H, NH-1), 8.50 (d, J=2.0 Hz, 1 H, H-5), 7.92 (d, J=2.0 Hz, 1 H, H-7), 7.52 (br. s, 2 H, H$_2$-2', 6'), 7.45 (t, J=7.5 Hz, 1 H, H-5'), 7.40 (d, J=7.5 Hz, 1 H, H-4'), 6.57 (s, 1 H, H-3), 2.43 (s, 3 H, CH$_3$-3'), 2.38 (s, 3 H, CH$_3$-6). MS m/z 250 (M$^+$). Elemental Analysis: calculated C 75.42, H 5.74, N 10.99; found C 75.31, H 5.63, N 10.84.

2-(3'-Methylphenyl)-7-methyl-1,8-naphthyridin-4-one (40') is obtained from compound (16'). Characteristics: amorphous; $^1$H NMR (CDCl$_3$) δ 9.23, (br. s, 1 H, NH-1), 8.57 (d, J=8.0 Hz, 1 H, H-5), 7.49 (br. s, 2 H, H$_2$-2', 6'), 7.42 (t, J=7.2, Hz, 1 H, H-5'), 7.36(d, J=7.2 Hz, 1 H, H-4'), 7.20 (d, J=8.0 Hz, 1 H, H-6), 6.60 (s, 1 H, H-3), 2.58 (s, 3 H, CH$_3$-7), 2.43 (s, 3 H, CH$_3$-3'). MS m/z 250 (M$^+$). Elemental Analysis: calculated C 76.78, H 5.64, N 11.19; found C 76.61, H 5.78, N 11.11.

2-(3'-Methylphenyl)-5,7-dimethyl-1,8-naphthyridin-4-one (41') is obtained from compound (17'). Characteristics: amorphous; $^1$H NMR (CDCl$_3$) δ 9.14, (br. s, 1 H, NH-1), 7.47 (br. s, 2 H, H$_2$-2', 6'), 7.40 (t, J=7.5, Hz, 1 H, H-5'), 7.34 (d, J=7.5 Hz, 1 H, H-4'), 6.89 (s, 1 H, H-6), 6.50 (s, 1 H, H-3), 2.94 (s, 3 H, CH$_3$-5), 2.42 (s, 3 H, CH$_3$-7), 2.47 (s, 3 H, CH$_3$-3'). MS m/z 264 (M$^+$). Elemental Analysis: calculated C 77.25, H 6.10, N 10.60; found C 77.51, H 6.38, N 10.71.

2-(α-Naphthyl)-1,8-naphthyridin-4-one (42') is obtained from compound (18'). Characteristics: plates; $^1$H NMR (CDCl$_3$) δ 8.67 (dd, J=8.0, 1.5 Hz, 1 H, H-5), 8.08 (d, J=8.0 Hz, 1 H, H-2'), 7.99 (d, J=8.0 Hz, 1 H, H-8'), 7.97 (d, J=8.0 Hz, 1 H, H-5'), 7.68 (d, J=8.0 Hz, 1 H, H-4'), 7.62 (t, J=8.0 Hz, 1 H, H-3'), 7.57 (d, J=8.0 Hz, 1 H, H-6'), 7.52 (d, J=8.0 Hz, 1 H, H-7'), 7.49 (d, J=4.5 Hz, 1 H, H-7), 7.11 (dd, J=8.0, 4.5 Hz, 1 H, H-6), 6.56 (s, 1 H, H-3). MS m/z 272 (M$^+$). Elemental Analysis: calculated C 79.40, H 4.44, N 10.29; found C 79.52, H 4.64, N 10.32.

2-(α-Naphthyl)-5-methyl-1,8-naphthyridin-4-one (43') is obtained from compound (19'). Characteristics: amorphous; $^1$H NMR (CDCl$_3$) δ 11.37, (br. s, 1 H, NH-1), 8.06 (d, J=7.8 Hz, 1 H, H-2'), 7.97 (d, J=8.5 Hz, 2 H, H$_2$-5', 8'), 7.65 (br. d, J=6.5 Hz, 1 H, H-4'), 7.62 (t, J=7.8 Hz, 1 H, H-3'), 7.56 (d, J=7.5 Hz, 1 H, H-6'), 7.48 (d, J=7.5 Hz, 1 H, H-7'), 7.00 (d, J=4.8 Hz, 1 H, H-7), 6.71 (d, J=4.8 Hz, 1 H, H-6), 6.46(s, 1 H, H-3), 2.93 (s, 3 H, CH$_3$-5). MS m/z 286 (M$^+$). Elemental Analysis: calculated C 79.70H 4.93, N 9.78; found C 79.55, H 5.12, N 9.51.

2-(α-Naphthyl)-6-methyl-1,8-naphthyridin-4-one (44') is obtained from compound (20'). Characteristics: amorphous;

¹H NMR (CDCl₃) δ 8.39 (d, J=1.0 Hz, 1 H, H-5), 8.10 (dd, J=7.5, 1.5 Hz, 1 H, H-2'), 7.99 (d, J=8.0 Hz, 1 H, H-8'), 7.88 (d, J=8.0 Hz, 1 H, H-5'), 7.66 (br. d, J=7.0 Hz, 1 H, H-4'), 7.65 (d, J=1.0 Hz, 1 H, H-7), 7.63 (t, J=7.5 Hz, 1 H, H-3'), 7.54 (t, J=7.5 Hz, 1 H, H-6'), 7.44 (t, J=7.5 Hz, 1 H, H-7'), 6.50 (s, 1 H, H-3), 2.12 (s, 3 H, CH₃-6). MS m/z 286 (M⁺). Elemental Analysis: calculated C 79.70, H 4.93, N 9.78; found C 79.49, H 5.21, N 9.48.

2-(α-Naphthyl)-7-methyl-1,8-naphthyridin-4-one (45') is obtained from compound (21'). Characteristics: amorphous; ¹H NMR (CDCl₃) δ 10.78, (br. s, 1 H, NH-1), 8.48 (d, J=8.0 Hz, 1 H, H-5), 7.97 (d, J=8.0 Hz, 1 H, H-2'), 7.92 (d, J=8.0 Hz, 1 H, H-8'), 7.85 (d, J=8.0 Hz, 1 H, H-5'), 7.58 (dd, J=7.0, 1.0 Hz, 1 H, H-4'), 7.51 (t, J=8.0 Hz, 1 H, H-3'), 7.43 (dt, J=7.0, 1.0 Hz, 1 H, H-6'), 7.32 (dt, J=7.0, 1.0 Hz, 1 H, H-7'), 6.93 (d, J=8.0 Hz, 1 H, H-6), 6.50 (s, 1 H, H-3), 2.06 (s, 3 H, CH₃-7). MS m/z 286 (M⁺). Elemental Analysis: calculated C 77.27, H 5.12, N 9.49; found C 77.12, H 5.45, N 9.17.

2-(α-Naphthyl)-5,7-dimethyl-1,8-naphthyridin-4-one (46') is obtained from compound (22'). Characteristics: amorphous; ¹H NMR (CDCl₃) δ 7.98 (d, J=7.5 Hz, 1 H, H-2'), 7.95 (d, J=8.0 Hz, 1 H, H-8'), 7.88 (d, J=8.0 Hz, 1 H, H-5'), 7.60 (dd, J=6.5, 1.0 Hz, 1 H, H-4'), 7.53 (t, J=7.5 Hz, 1 H, H-3'), 7.49 (dt, J=6.0, 2.0 Hz, 1 H, H-6'), 7.38 (dt, J=7.0, 1.0 Hz, 1 H, H-7'), 6.69 (s, 1 H, H-6), 6.45 (s, 1 H, H-3), 2.91 (s, 3 H, CH₃-5), 2.10 (s, 3 H, CH₃-7). MS m/z 300 (M⁺). Elemental Analysis: calculated C 79.98, H 5.37, N 9.33; found C 79.74, H 5.56, N 9.18.

2-(β-Naphthyl)-1,8-naphthyridin-4-one (47') is obtained from compound (23'). Characteristics: amorphous; ¹H NMR (CDCl₃) δ 9.98 (br. s, 1 H, NH-1), 8.71 (dd, J=8.0, 1.5 Hz, 1 H, H-5), 8.44 (d, J=4.5 Hz, 1 H, H-7), 8.24 (d, J=1.0 Hz, 1 H, H-1'), 8.04 (d, J=8.5 Hz, 1 H, H-4'), 7.94 (m, 2 H, H₂-5', 8'), 7.80 (dd, J=8.5, 2.0 Hz, 1 H, H-3'), 7.63(m, 2 H, H₂-6', 7'), 7.28 (dd, J=8.0, 4.5 Hz, 1 H, H-6), 6.76 (s, 1 H, H-3). MS m/z 272 (M⁺). Elemental Analysis: calculated C 79.40, H 4.44, N 10.29; found C 79.62, H 4.71, N 10.37.

2-(β-Naphthyl)-5-methyl-1,8-naphthyridin-4-one (48') is obtained from compound (24'). Characteristics: needles; ¹H NMR (CDCl₃) δ 10.09, (br. s, 1 H, NH-1), 8.21 (d, J=1.0 Hz, 1 H, H-1'), 8.08 (d, J=5.0 Hz, 1 H, H-7), 8.01 (d, J=8.5 Hz, 1 H, H-4'), 7.93 (m, 2 H, H₂-5', 8'), 7.79 (dd, J=8.5, 2.0 Hz, 1 H, 3'), 7.61 (m, 2 H, H₂-6', 7'), 6.93 (d, J=5.0 Hz, 1 H, H-6), 6.67 (s, 1 H, H-3), 2.99 (s, 3 H, CH₃-5). MS m/z 286 (M⁺). Elemental Analysis: calculated C 79.70, H 4.93, N 9.78; found C 79.79, H 5.15, N 9.56.

2-(β-Naphthyl)-6-methyl-1,8-naphthyridin-4-one (49') is obtained from compound (25'). Characteristics: amorphous; ¹H NMR (CDCl₃) δ 8.49 (d, J=2.0 Hz, 1 H, H-5), 8.21 (d, J=1.0 Hz, 1 H, H-1'), 8.03 (d, J=8.5 Hz, 1 H, H-4'), 7.97 (m, 2 H, H₂-5', 8'), 7.87 (d, J=1.0 Hz, 1 H, H-7), 7.79 (dd, J=8.5, 2.0 Hz, 1 H, H-3'), 7.62 (m, 2 H, H₂-6', 7'), 6.72 (s, 1 H, H-3), 2.24 (s, 3 H, CH₃-6), MS m/z 286 (M⁺). Elemental Analysis: calculated C 79.70, H 4.93, N 9.78; found C 79.66, H 4.98, N 9.86.

2-(β-Naphthyl)-7-methyl-1,8-naphthyridin-4-one (50') is obtained from compound (26'). Characteristics: needles; ¹H NMR (CDCl₃) δ 9.32, (br. s, 1 H, NH-1), 8.59 (d, J=8.0 Hz, 1 H, H-5), 8.19 (d, J=2.0 Hz, 1 H, H-1'), 8.01 (d, J=8.5 Hz, 1 H, H-4'), 7.92 (m, 2 H, H₂-5', 8'), 7.76 (dd, J=8.5, 2.0 Hz, 1 H, H-3'), 7.61 (m, 2 H, H₂-6', 7'), 7.21 (d, J=8.0 Hz, 1 H, H-6), 6.74 (s, 1 H, H-3), 2.60 (s, 3 H, CH₃-7). MS m/z 286 (M⁺). Elemental Analysis: calculated C 79.70, H 4.93, N 9.78; found C 79.83, H 5.05, N 9.69.

2-(β-Naphthyl)-5,7-dimethyl-1,8-naphthyridin-4-one (51') is obtained from compound (27'). Characteristics: amorphous; ¹H NMR (CDCl₃) δ 9.20, (br. s, 1 H, NH-1), 8.17 (d, J=1.5 Hz, 1 H, H-1'), 7.99 (d, J=8.5 Hz, 1 H, H-4'), 7.92 (m, 2 H, H₂-5', 8'), 7.75 (dd, J=8.5, 1.5 Hz, 1 H, H-3'), 7.60 (m, 2 H, H₂-6', 7'), 6.90 (s, 1 H, H-6), 6.65 (s, 1 H, H-3), 2.96 (s, 3 H, CH₃-5), CH₃-7). MS m/z 300(M⁺). Elemental Analysis: calculated C 70.48, H 3.61, N 9.13; found C 70.61, H 3.93, N 9.25.

EXAMPLE 10

Cytotoxicity assays of Compounds 5'–51'

Compounds 5'–28' were assayed for in vitro cytotoxicity in a panel of human and murine tumor cell lines using the same techniques as in Example 5. The cell lines include human epidermoid carcinoma of the nasopharynx (KB), lung carcinoma (A-549), ileocecal carcinoma (HCT-8), melanoma (PRMI-795 1), and medulloblastoma (TE-671), as well as one murine leukemia cell line (P-388). The results demonstrated that essentially all 2-phenyl-pyrido[1,2-a]pyrimidin-4-ones (5'–28') were inactive ($EC_{50}>4$ μg/ml); only a few compounds showed marginal activity.

Compounds 29'–51' were submitted to NCI and assayed in the NCI's in vitro disease-oriented antitumor screen, using the techniques described in Example 5. This assay involves determinations of a test agent's effect on growth parameters against a panel of approximately 60 human tumor cell lines, derived largely from solid tumors, including non-small cell lung, colon, central nervous system, renal, ovarian, prostate, and breast cancers, plus a few leukemia cell lines. The cytotoxic effects of each compound are obtained as $GI_{50}$ or TGI values, which represent the molar drug concentrations required to cause half growth inhibition and total growth inhibition, respectively. The results are expressed for each cell line as average log $GI_{50}$ values in Table 4, as log $GI_{50}$ values in Table 5, and as log TGI values and average log TGI values in Table 6.

TABLE 4

| Compound | ITP[1] HC₅₀ (μM) ± SD | ICB[2] (% Inhibition) | average[3] log GI₅₀ | mp (° C.) | Yield (%)[4] |
|---|---|---|---|---|---|
| 29' | 0.63 ± 0.2 | 43 ± 1 | −7.30 | >300 | 57 |
| 30' | 0.53 ± 0.08 | 41 ± 2 | −7.37 | 270–272 | 48 |
| 31' | 0.74 ± 0.06 | 29 ± 1 | −7.07 | 236–238 | 57 |
| 32' | 1.5 ± 0.1 | | −6.64 | 295–297 | 26 |
| 33' | 1.0 ± 0.03 | 32 ± 1 | −6.80 | 260–262 | 21 |
| 34' | 0.72 ± 0.08 | 33 ± 2 | −6.57 | 290–292 | 49 |
| 35' | 0.89 ± 0.09 | 38 ± 1 | −6.77 | 255–257 | 17 |
| 36' | 0.77 ± 0.2 | 22 ± 2 | −6.46 | 232–234 | 49 |
| 37' | 3.3 ± 0.6 | | −7.02 | 205–207 | 33 |
| 38' | 1.8 ± 0.5 | | −7.24 | 175–177 | 32 |

TABLE 4-continued

| Compound | ITP[1] HC$_{50}$ ($\mu$M) ± SD | ICB[2] (% Inhibition) | average[3] log GI$_{50}$ | mp (° C.) | Yield (%)[4] |
|---|---|---|---|---|---|
| 39' | 1.5 ± 0.3 | | −6.19 | 223–225 | 36 |
| 40' | 1.9 ± 0.5 | | −7.01 | 193–195 | 52 |
| 41' | 2.3 ± 0.2 | | −4.42 | 197–198 | 55 |
| 42' | 1.1 ± 0.3 | | −7.45 | 282–283 | 27 |
| 43' | 0.93 ± 0.2 | 37 ± 4 | −7.45 | 228–230 | 27 |
| 44' | 0.55 ± 0.05 | 46 ± 3 | −7.72 | 236–238 | 25 |
| 45' | 0.66 ± 0.1 | 40 ± 4 | −7.18 | 240–242 | 34 |
| 46' | 0.78 ± 0.2 | 15 ± 10 | −5.98 | 276–278 | 37 |
| 47' | 14 ± 2 | | −5.09 | 259–261 | 38 |
| 48' | 1.8 ± 0.06 | | −5.92 | 217–219 | 29 |
| 49' | 2.1 ± 0.5 | | −6.13 | 255–257 | 34 |
| 50' | 5.1 ± 0.9 | | −5.34 | 244–246 | 45 |
| 51' | >40 | | −4.87 | 149–151 | 59 |
| 52' | 2.5 ± 0.5 | | −5.24 | >300 | 51 |
| colchicine | 0.08 ± 0.07 | | | | |
| podophyllotoxin | 0.46 ± 0.02 | 76 ± 5 | | | |
| combretstatin A-4 | 0.53 ± 0.05 | 91 ± 2 | | | |

[1]Inhibition of Tubulin Polymerization,
[2]Inhibition of colchicine binding (evaluated only when polymerization IC50 ≦ 1 $\mu$M),
[3]Data obtained from NCI's 60 human tumor cell line in vitro screen and calculated from all cell lines tested,
[4]All yields were calculated form aminopyridines,
[5]Not tested.

TABLE 5

| | Cytotoxicity log GI$_{50}$ (M)[1] | | | | | | | | | | |
|---|---|---|---|---|---|---|---|---|---|---|---|
| Compound | HL-60(TB)[2] | NCI-H460 | HCT-1.16 | SF-295 | U-251 | SK-MEL-5 | OVCAR-3 | 786-0 | PC-3 | MDA-MB-435 | MDA-N |
| 29' | −7.69 | −7.41 | −7.62 | −7.56 | −7.39 | −7.55 | −7.87 | −7.55 | −7.46 | < −8.00 | −7.93 |
| 30' | −7.65 | −7.48 | −7.55 | −7.54 | −7.42 | −7.65 | −7.71 | −7.34 | −7.46 | −7.91 | −7.84 |
| 31' | −7.43 | −7.27 | < −8.00 | −7.48 | −7.19 | −7.43 | −7.74 | −7.45 | −7.21 | < −8.00 | −7.89 |
| 32' | −7.98 | −7.06 | −7.54 | −7.20 | −6.84 | −7.28 | −7.34 | −7.25 | −7.65 | < −8.00 | −7.76 |
| 33' | −8.00 | −7.41 | −7.80 | −7.39 | −7.28 | −7.38 | −7.50 | −7.48 | −7.81 | < −8.00 | −7.93 |
| 34' | −7.51 | −7.30 | −7.52 | −7.60 | −7.16 | −7.15 | −7.65 | −7.37 | > −4.00 | < −8.00 | > −4.00 |
| 35' | −7.54 | −7.38 | −7.59 | −7.64 | −7.19 | −7.50 | < −8.00 | −7.38 | > −4.00 | < −8.00 | > −4.00 |
| 36' | −7.13 | −6.65 | −6.77 | −7.32 | −6.53 | −6.93 | −6.77 | −6.69 | −7.56 | −7.88 | −7.72 |
| 37' | −7.72 | −7.59 | −7.65 | −7.43 | −7.35 | −7.59 | −7.38 | −7.43 | −7.37 | < −8.00 | < −8.0 |
| 38' | −7.74 | −7.44 | −7.33 | −7.52 | −7.27 | −7.47 | −7.65 | −7.27 | −7.48 | < −8.00 | −7.96 |
| 39' | −6.76 | −6.41 | −6.39 | −6.38 | −6.77 | −6.54 | −6.60 | −6.36 | −6.51 | < −8.00 | < −8.0 |
| 40' | −7.57 | −7.75 | −6.92 | −7.22 | −6.70 | −6.90 | −6.31 | −6.37 | −6.86 | −7.49 | −7.50 |
| 41' | −4.89 | −4.35 | −4.75 | −4.19 | −4.27 | −4.46 | −4.52 | −4.25 | −4.50 | −4.70 | −4.68 |
| 42' | < −8.00 | −7.41 | < −8.00 | < −8.00 | −7.99 | < −8.00 | < −8.00 | −7.82 | −7.75 | < −8.00 | < −8.00 |
| 43' | < −8.00 | < −8.00 | < −8.00 | −7.97 | < −8.00 | < −8.00 | < −8.00 | −7.92 | −7.70 | < −8.00 | < −8.00 |
| 44' | < −8.00 | < −8.00 | < −8.00 | < −8.00 | < −8.00 | < −8.00 | < −8.00 | < −8.00 | < −8.00 | < −8.00 | < −8.00 |
| 45' | < −8.00 | −7.76 | < −8.00 | −7.62 | −7.81 | −7.86 | < −8.00 | −5.22 | −7.52 | < −8.00 | < −8.00 |
| 46' | −6.61 | −6.20 | −6.42 | −6.23 | −6.43 | −6.33 | −6.46 | −5.02 | −6.12 | −6.72 | −6.63 |
| 47' | −5.74 | −5.42 | −5.42 | −5.04 | −5.36 | −5.46 | −5.08 | −5.25 | −4.98 | −5.75 | −5.78 |
| 48' | −6.69 | −5.98 | −6.37 | −5.83 | −6.19 | −6.36 | −5.89 | −5.62 | −5.86 | −6.69 | −6.69 |
| 49' | −6.85 | −6.40 | −6.33 | −6.26 | −6.33 | −6.44 | −6.45 | −6.21 | −6.39 | −6.98 | −6.88 |
| 50' | −5.75 | −5.42 | −5.40 | −5.42 | −5.34 | −5.48 | −5.44 | −5.27 | −5.58 | −5.80 | −5.71 |
| 51' | −5.46 | −4.88 | −4.90 | −4.83 | −4.80 | −5.66 | −4.70 | −4.29 | −5.26 | −5.53 | −5.49 |
| 52' | −5.75 | −5.39 | −5.40 | −5.26 | −5.32 | −5.53 | −5.58 | −5.12 | −5.51 | −6.07 | −5.81 |

[1]Log concentrations which reduced cell growth to 50% of level at start of experiment.
[2]HL-60(TB): leukemia cell line; NC-H460: non-small cell lung cancer cell line; HCT-116: colon cancer cell line; SF-295 & U251: CNS cancer cell lines; SK-MEL-5: melanoma cell line; OVCAR-3: ovarian cancer cell line; 786-0: renal cancer cell line; PC-3: prostate cancer cell ine; MDA-MB-435 & MDA-N: breast cancer cell lines.
[3]Not tested.

TABLE 6

| | Cytotoxicity log TGI (M)[1] per compound | | | | | | | |
|---|---|---|---|---|---|---|---|---|
| Cell line | 29' | 30' | 31' | 32' | 33' | 34' | 35' | 36' |
| average | −5.29 | −5.33 | −5.25 | −4.62 | −4.59 | −4.51 | −4.67 | −4.58 |
| leukemia | −5.57 | −5.56 | −5.61 | −4.41 | > −4.00 | −4.14 | > −4.00 | −4.09 |
| non-small cell lung cancer | −4.79 | −5.24 | −5.60 | −4.07 | > −4.00 | −4.35 | −4.61 | > −4.00 |
| colon cancer | −6.49 | −6.26 | −5.93 | −4.79 | −4.92 | −5.02 | −5.51 | −4.54 |
| CNS cancer | −5.51 | −5.65 | −5.01 | −4.78 | −4.74 | −5.72 | −5.71 | −5.30 |

TABLE 6-continued

| | Cytotoxicity log TGI (M)[1] per compound | | | | | | | |
|---|---|---|---|---|---|---|---|---|
| Cell line | 29' | 30' | 31' | 32' | 33' | 34' | 35' | 36' |
| melanoma | −4.49 | −4.62 | −4.86 | −4.01 | −4.15 | −4.32 | −4.16 | −4.14 |
| ovarian cancer | −4.57 | −4.99 | −5.26 | −4.50 | −4.56 | −4.80 | −4.89 | −4.52 |
| renal cancer | −4.26 | −4.19 | −4.31 | −4.31 | −4.16 | −4.06 | >−4.00 | −4.23 |
| prostate cancer | −6.16 | −5.80 | −4.31 | −5.58 | −5.63 | >4.00 | >−4.00 | −5.51 |
| breast cancer | −6.27 | −6.24 | −6.00 | −5.93 | −6.09 | −4.89 | −5.42 | −5.91 |

[1]log molar concentrations required to cause total growth inhibition.

All compounds had cytotoxic activity (log $GI_{50}$<−4.00) against all cell lines tested. Among the three subseries of 2-phenyl-1,8-naphthyridin-4-ones, only compound 41' had limited activity, for compounds 29'–40' were inhibitory toward most cell lines in the submicromolar (log $GI_{50}$'s of −7 to −6) to nanomolar (log $GI_{50}$'s of −8 to −7) range. Ignoring compound 41', and considering only the average log GI50 values, which takes into account all the cell lines tested (not just those shown in Table 5), the agents with 3'-fluoride and methyl groups were slightly more cytotoxic than those with a 3'-chloride group. The 3'-fluoride compounds, in particular, have cytotoxicity comparable to that reported earlier for agents bearing a 3'-methoxy substituent.

A fairly dramatic difference was observed between the 2-(α-naphthyl) compounds (42'–46') and the 2-(β-naphthyl) compounds (47'–52') derivatives. In the former group, except for compound 46', low nanomolar $GI_{50}$ values (log<−8) were observed with many cell lines. In the latter group, in contrast, submicromolar $GI_{50}$ values were rarely obtained with any agent except compound 49'. Note, moreover, that 2-(β-naphthyl) compound 49' was at least 50-fold less active than its 2-(α-naphthyl) congener compound 44'.

As in Example 5above substituents in the C ring altered substituent effects in the A ring. With a 3'-halogen, cytotoxicity was apparently unaffected by A ring substituents, within the limited range of available compounds. With a 3'-methyl group and with both 2-naphthyl series, cytotoxicity was unfavorably affected by methyl groups at both position 5 and position 7. With a 3'-methyl group, a methyl group at position 6was less favorable than either no substituent or a methyl group at positions 5 or 7. In the α-naphthyl series, a methyl substituent at position 5, 6, or 7 was equivalent, and cytotoxicity differed little from that of the unsubstituted compound. In the β-naphthyl series, greater activity was observed in the compounds with methyl groups at positions 5 or 6 than in the unsubstituted agent or that bearing a methyl group at position 7.

Interestingly, all 3'-halogenated compounds showed different selectivity in the tested tumor panels at the total growth inhibition (TGI) levels. Growth of cells from more sensitive panels was arrested at a concentration approximately 1–2 log concentrations lower than was growth of less sensitive panels. As summarized in Table 6, all 3'-halogenated compounds, except for compound 34', exhibited a highly selective effect at the TGI level on the breast cancer panel. In the 3'-fluoro analogs, the compound with a methyl group at position 6 (29') showed high selectivity for the colon, prostate, and breast panels; the analog with a methyl group at position 7 (30') demonstrated high selectivity for the colon and breast panels and moderate selectivity for the prostate panel; and the compound with methyl groups at positions 5 and 7 (31') exhibited highly selective effects on the colon and breast panels. In the 3'-chloro compounds, substitution of a methyl group at position 5 (32') or no substitution (33') in ring A produced high selectivity for the prostate and breast panels; a methyl at position 6 (34') conferred high selectivity for the CNS panel and moderate selectivity for the colon, ovarian, and breast panels; a methyl substituent at position 7 (35') gave highly selective effects on the colon, CNS, and breast panels; and methyl groups at positions 5 and 7 (36') produced high selectivity for the CNS, prostate, and breast panels.

EXAMPLE 11

Antimicrotubule Assay of Compounds 29'–51'

Electrophoretically homogeneous bovine brain tubulin was purified as described in Example 6. Combretastatin A-4 was a generous gift of Dr. G. R. Pettit, Arizona State University.

The tubulin polymerization assay was performed as described in Example 6. Data presented in Table 4 demonstrate that the new agents described here, both the new 2-phenyl-1,8-naphthyridin-4-ones and the 2-naphthyl derivatives, also interact with tubulin, with good correlation between their cytotoxic properties and their relative activity as inhibitors of tubulin assembly.

Among the compounds examined here, only one compound was inactive (51'; $IC_{50}$ value>40 μM), one weakly active (47'; $IC_{50}$ value, 14 μM), and one moderately active (50'; $IC_{50}$ value, 5.1 μM). These three compounds were among the least cytotoxic agents, in terms of the average log $GI_{50}$ values. At the opposite extreme, eleven compounds (29'–31', 33'–36', and 43'–46') were highly potent inhibitors of tubulin polymerization, with $IC_{50}$ values of 1.0 μM or less. This is the group that has activity comparable to that observed with the natural products colchicine, podophyllotoxin, and combretastatin A-4. Six of these agents had average log GI50 values below −7, and the remainder fell between −7 and −6. The remaining ten compounds (32', 37'–42', 48', 49', and 52') inhibited tubulin assembly with $IC_{50}$ values of 1.1 to 3.3 μM. Four of these compounds (37', 38', 40', and 42') were among the most cytotoxic agents (log $GI_{50}$ values of −7 or less), three (32', 39', and 49') were moderately cytotoxic with log $GI_{50}$ values between −7 and −6, and three (41', 48', and 52') had little cytotoxicity (log $GI_{50}$ values>6).

Considering structure-activity aspects solely from the point of view of inhibition of tubulin polymerization, the 3'-fluoride and 3'-chloride substituents appeared to be equivalent, differed little in their activity from the previously described 3'-methoxy series, and were more active than the analogous derivatives with the 3'-methyl substituent. With the 3'-halogen series and the 3'-methyl series, derivatives with different methyl substituents in the A ring all had nearly equivalent activity. In the chloride and methyl series the data suggest that the derivatives that are unsubstituted in the A ring (compounds 32' and 37') were less active than those bearing methyl substituent(s).

The 2-(α-naphthyl) compounds (42'–46') were comparable in activity to the 3'-halogen derivatives. In this series, too, substituents in the A ring had little effect on inhibitory activity. It was only in the less active 2-(β-naphthyl) compounds (47'–52') that A ring substitution affected the apparent interaction with tubulin. A methyl substituent at either position 5 (48') or 6 (49') decreased the $IC_{50}$ value 7-fold relative to the value obtained with the unsubstituted compound 47', while a methyl substituent at position 7 decreased the $IC_{50}$ value 3-fold. In contrast, two methyl groups at positions 5 and 7 abolished activity. In the 2-(β-naphthyl) compounds, we found no significant difference between methyl and chloride substituents at position 6.

EXAMPLE 12

Colchicine Binding Assay of Compounds 29'–51'

The binding of radiolabeled colchicine to tubulin was measured by the DEAE-cellulose filter technique, as described in Example 7.

All compounds that inhibited tubulin assembly with $IC_{50}$ values of 1.0 μM or less were compared with podophyllotoxin and combretastatin A-4 for inhibitory effects on the binding of [$^3$H]colchicine to tubulin (data summarized in Table 4). In these experiments inhibitor and colchicine were equimolar and in 5-fold molar excess over tubulin. All agents, except possibly compound 46', significantly inhibited colchicine binding to tubulin, but none was as potent as either podophyllotoxin or combretastatin A-4. Without wishing to be bound by any particular theory, we suspect that the quantitative differences between the assembly assay and the [$^3$H]colchicine assay result from differences in relative rates of drug binding and dissociation from tubulin and from the stoichiometric character of the [$^3$H]colchicine assay versus the cooperative character of the assembly assay. However, the [$^3$H]colchicine binding assay does detect reduced activity in the 5,7-dimethyl derivatives that was not apparent in either the cytotoxicity or polymerization assays (cf. results with 31' vs. 29' and 30'; with 36' vs. 33'–35'; and with 46' vs. 43'–45').

That which is claimed is:
1. A compound of Formula I:

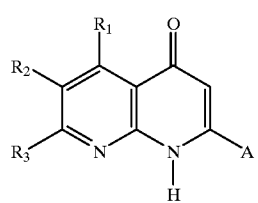

wherein A is an aromatic moeity selected from the the group consisting of:

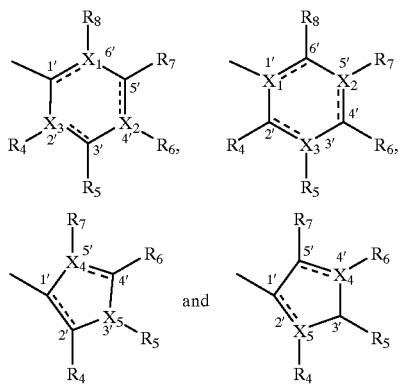

wherein:

$X_1$, $X_2$, and $X_3$ are each individually selected from the group consisting of C, or N;

$X_4$ and $X_5$ are each individually selected from the group consisting of C, N, O, and S wherein at least one of $X_4$ and $X_5$ is N, O, or S;

$R_1$, $R_2$, $R_3$, $R_4$, $R_5$, $R_6$, $R_7$, and $R_8$ are each independently selected from the group consisting of H, alkyl, hydroxyl, alkoxyl, aryloxyl, halo, amino, alkylamino, dialkylamino, or nitro, or alterantively, two adjacent R groups together may form a bridging group selected from the group consisting of alkydienyl, alkyleneoxy, alkylenedioxy, alkyleneimine, and alkylenediimine; and the dashed line indicates that the bond may be a double bond or a single bond, with the provisos that:

when any of $X_1$, $X_2$, $X_3$, $X_4$ or $X_5$ is C, the dashed lines connected thereto are double bonds;

when any of $X_1$, $X_2$, or $X_3$ is N, the dashed lines connected thereto are double bonds and the R group attached at that position is absent;

when either $X_4$ or $X_5$, is N, the dashed lines connected thereto may be single bonds or double bonds, and when the dashed line is a double bond, the R group attached at that position is absent; and when either $X_4$ or $X_5$ is O or S, the dashed lines connected thereto are single bonds and the R group attached at that position is absent; subject to the proviso that when $R_1$ is H, $R_2$ is H, and $R_3$ is methyl, then A is not phenyl or 2-furyl.

2. The compound according to claim 1, wherein A is

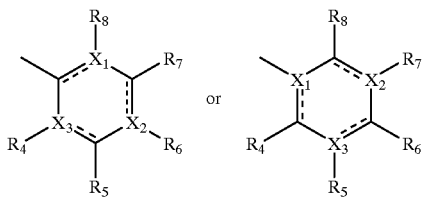

$X_1$, $X_2$, and $X_3$ are each C, all dashed lines are double bonds, and $R_4$ is alkoxy.

3. The compound according to claim 1, wherein A is

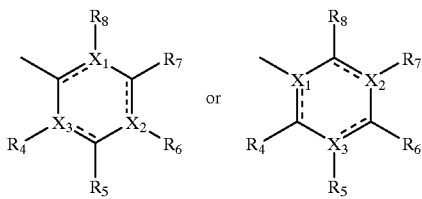 or 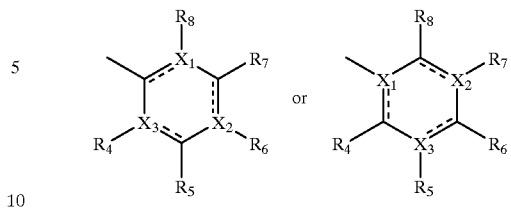

$X_1$, $X_2$, and $X_3$ are each C, all dashed lines are double bonds, and $R_4$ is alkoxy.

4. The compound according to claim 1, wherein A is

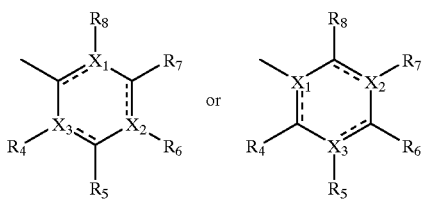 or 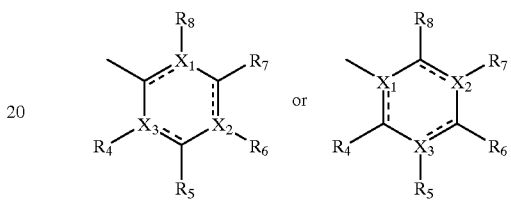

$X_1$, $X_2$, and $X_3$ are each C, all dashed lines are double bonds, and $R_6$ is alkoxy.

5. The compound according to claim 1, wherein A is

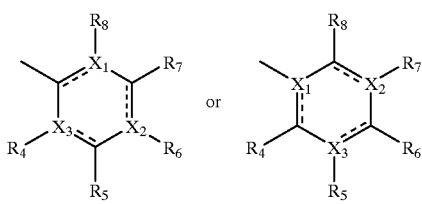 or 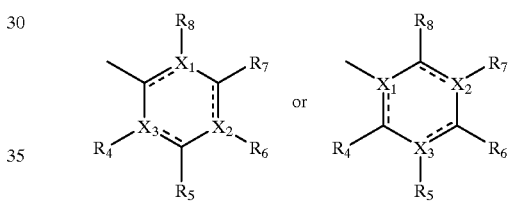

$X_1$, $X_2$, and $X_3$ are each C, all dashed lines are double bonds, and $R_6$ is halo.

6. The compound according to claim 1, wherein A is

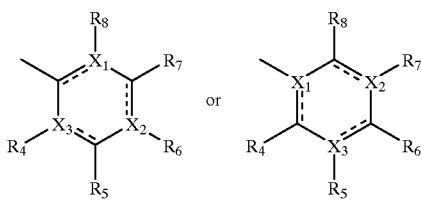 or $X_1$, $X_2$, and $X_3$ are each C, all dashed lines are double bonds, and $R_5$ is halo.

7. The compound according to claim 1, wherein A is

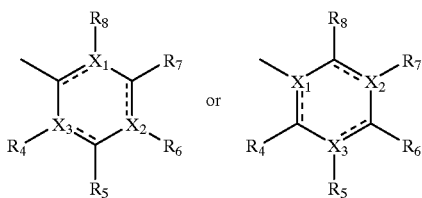 or $X_1$, $X_2$, and $X_3$ are each C, all dashed lines are double bonds, and $R_5$ is alkyl.

8. The compound according to claim 1, wherein A is or $X_1$, $X_2$, and $X_3$ are each C, all dashed lines are double bonds, and at least one of $R_1$, $R_2$, $R_3$, and $R_4$ is alkyl.

9. The compound according to claim 1, wherein A is or $X_1$, $X_2$, and $X_3$ are each C, all dashed lines are double bonds, and $R_4$ and $R_5$ together form an alkydienyl bridging group.

10. The compound according to claim 1, wherein A is or $X_1$, $X_2$, and $X_3$ are each C, all dashed lines are double bonds, and $R_5$ and $R_6$ together form an alkydienyl bridging group.

11. The compound according to claim 1, wherein A is

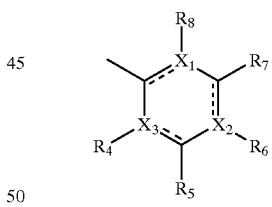

$X_1$, and $X_2$ are each C, $X_3$ is N, all dashed lines are double bonds, $R_2$ and $R_5$ are each alkyl, and $R_4$ is absent.

12. The compound according to claim 1, wherein A is

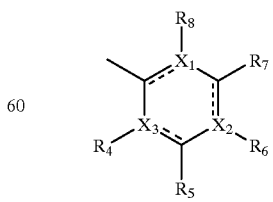

$X_1$ and $X_3$ are each C, $X_2$ is N, all dashed lines are double bonds, $R_3$ is alkyl, and $R_6$ is absent.

13. The compound according to claim 1, wherein A is

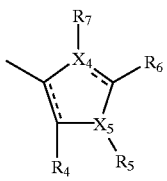

$X_4$ is C, $X_5$ is selected from the group consisting of O, S, and N, all dashed lines are double bonds, and $R_2$ is alkyl and $R_5$ is absent.

14. The compound according to claim 1, wherein A is

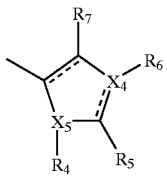

$X_4$ is C, $X_5$ is selected from the group consisting of O, S, and N, all dashed lines are double bonds, $R_2$ is alkyl, and $R_4$ is absent.

15. A method of inhibiting cellular mitosis, said method comprising contacting a cell with a compound of Formula I:

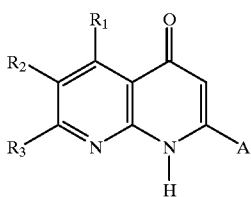

wherein A is an aromatic moeity selected from the group consisting of:

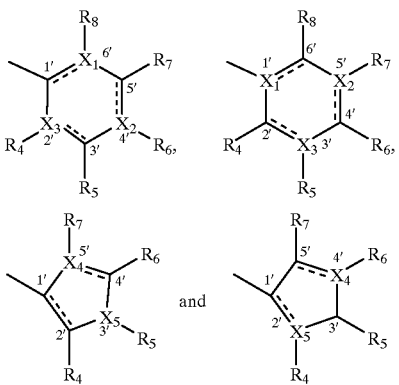

wherein:
$X_1$, $X_2$, and $X_3$ are each individually selected from the group consisting of C, or N;
$X_4$ and $X_5$ are each individually selected from the group consisting of C, N, O, and S wherein at least one of $X_4$ and $X_5$ is N, O, or S;
$R_1$, $R_2$, $R_3$, $R_4$, $R_5$, $R_6$, $R_7$, and $R_8$ are each independently selected from the group consisting of H, alkyl, hydroxyl, alkoxyl, aryloxyl, halo, amino, alkylamino, dialkylamino, or nitro, or alterantively, two adjacent R groups together may form a bridging group selected from the group consisting of alkydienyl, alkyleneoxy, alkylenedioxy, alkyleneimine, and alkylenediimine; and the dashed line indicates that the bond may be a double bond or a single bond, with the provisos that:
when any of $X_1$, $X_2$, $X_3$, $X_4$ or $X_5$ is C, the dashed lines connected thereto are double bonds;
when any of $X_1$, $X_2$, or $X_3$ is N, the dashed lines connected thereto are double bonds and the R group attached at that position is absent;
when either $X_4$ or $X_5$ is N, the dashed lines connected thereto may be single bonds or double bonds, and when the dashed line is a double bond, the R group attached at that position is absent; and
when either $X_4$ or $X_5$ is O or S, the dashed lines connected thereto are single bonds and the R group attached at that position is absent; in an amount effective to inhibit cellular mitosis.

16. The method according to claim 15, wherein A is

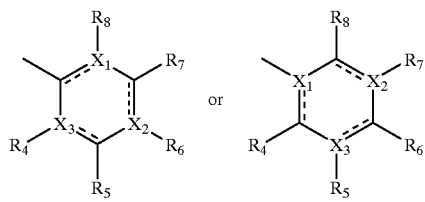

$X_1$, $X_2$, and $X_3$ are each C, all dashed lines are double bonds, and $R_4$ is alkoxy.

17. The method according to claim 15, wherein A is

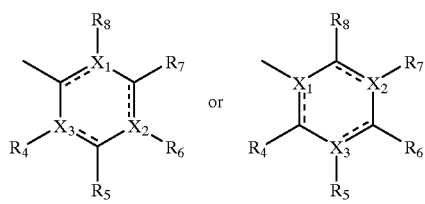

$X_1$, $X_2$, and $X_3$ are each C, all dashed lines are double bonds, and $R_5$ is alkoxy.

18. The method according to claim 15, wherein A is

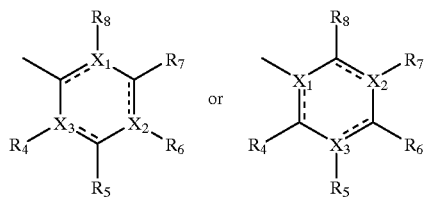

$X_1$, $X_2$, and $X_3$ are each C, all dashed lines are double bonds, and $R_6$ is alkoxy.

19. The method according to claim 15, wherein A is

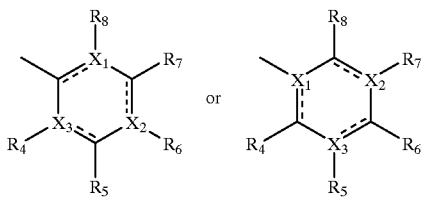 or $X_1$, $X_2$, and $X_3$ are each C, all dashed lines are double bonds, and $R_6$ is halo.

20. The method according to claim 15, wherein A is

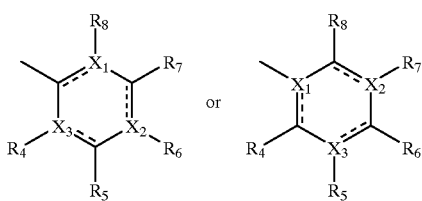 or $X_1$, $X_2$, and $X_3$ are each C, all dashed lines are double bonds, and $R_5$ is halo.

21. The method according to claim 15, wherein A is

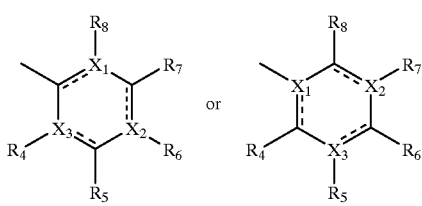 or $X_1$, $X_2$, and $X_3$ are each C, all dashed lines are double bonds, and $R_5$ is alkyl.

22. The method according to claim 15, wherein A is

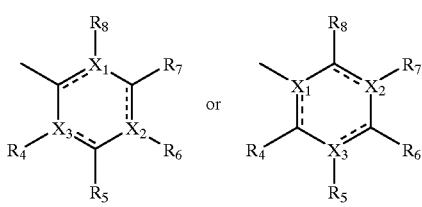 or $X_1$, $X_2$, and $X_3$ are each C, all dashed lines are double bonds, and at least one of $R_1$, $R_2$, $R_3$, and $R_4$ is alkyl.

23. The method accordint to claim 15, wherein A is

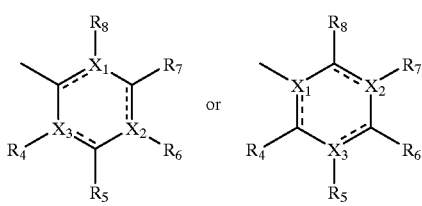 or $X_1$, $X_2$, and $X_3$ are each C, all dashed lines are double bonds, and $R_4$ and $R_5$ together form an alkydienyl bridging group.

24. The method according to claims 15, wherein A is

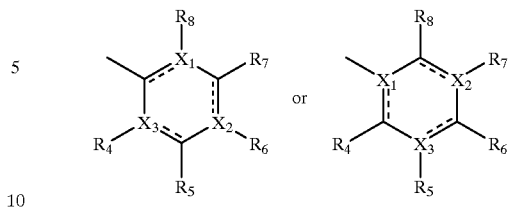 or $X_1$, $X_2$, and $X_3$ are each C, all dashed lines are double bonds, and $R_5$ and $R_6$ together form an alkydienyl bridging group.

25. The method according to claim 15, wherein A is

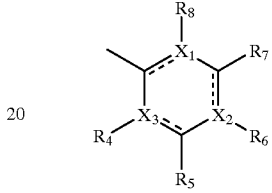

$X_1$ and $X_2$ are each C, $X_3$ is N, all dashed lines are double bonds, and $R_2$ and $R_5$ are each alky, and $R_4$ is absent.

26. The method according to claim 15, wherein A is

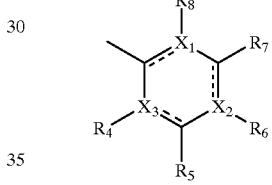

$X_1$ and $X_3$ are each C, $X_2$ is N, all dashed lines are double bonds, $R_3$ is alkyl, and $R_6$ is absent.

27. The method according to claim 15, wherein A is

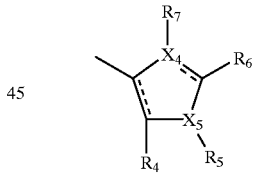

$X_4$ is C, $X_5$ is selected from the group consisting of O, S, and N, all dashed lines are double bonds, $R_2$ is alkyl, and $R_5$ is absent.

28. The method according to claim 15, wherein A is

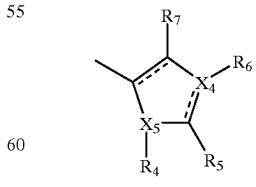

$X_4$ is C, $X_5$ is selected from the group consisting of O, S, and N, all dashed lines are double bonds, $R_2$ is alkyl, and $R_4$ is absent.

* * * * *

UNITED STATES PATENT AND TRADEMARK OFFICE
CERTIFICATE OF CORRECTION

PATENT NO. : 5,994,367
DATED : November 30, 1999
INVENTOR(S) : Lee et al.

It is certified that error appears in the above-identified patent and that said Letters Patent is hereby corrected as shown below:

On the title page

Under "Other Publications" in line 2 of the Kelly reference (page 2), please delete "Polophyllin" and insert -- Podophyllin --.

Column 19, line 20, after "Method" please add -- 1. --.

Claim 3, column 47, line 12, please delete "$R_4$" and insert -- $R_5$ --.
Claim 23, column 51, line 54, please delete "accordint" and insert -- according --.

Signed and Sealed this

First Day of May, 2001

NICHOLAS P. GODICI

*Attest:*

*Attesting Officer*     *Acting Director of the United States Patent and Trademark Office*